United States Patent
Zhang et al.

(10) Patent No.: US 9,522,881 B2
(45) Date of Patent: Dec. 20, 2016

(54) HYDROXYINDOLE CARBOXYLIC ACID BASED INHIBITORS FOR ONCOGENIC SRC HOMOLOGY-2 DOMAIN CONTAINING PROTEIN TYROSINE PHOSPHATASE-2 (SHP2)

(71) Applicant: Indiana University Research and Technology Corporation, Indianapolis, IN (US)

(72) Inventors: Zhong-Yin Zhang, Carmel, IN (US); Li-Fan Zeng, Indianapolis, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 14/786,621

(22) PCT Filed: Apr. 25, 2014

(86) PCT No.: PCT/US2014/035435
§ 371 (c)(1),
(2) Date: Oct. 23, 2015

(87) PCT Pub. No.: WO2014/176488
PCT Pub. Date: Oct. 30, 2014

(65) Prior Publication Data
US 2016/0102054 A1    Apr. 14, 2016

Related U.S. Application Data

(60) Provisional application No. 61/816,404, filed on Apr. 26, 2013.

(51) Int. Cl.
| | | |
|---|---|---|
| C07D 209/24 | (2006.01) | |
| C07D 403/12 | (2006.01) | |
| C07D 405/12 | (2006.01) | |
| C07D 409/12 | (2006.01) | |
| C07D 417/12 | (2006.01) | |
| A61K 31/404 | (2006.01) | |
| A61K 31/405 | (2006.01) | |
| A61K 31/4178 | (2006.01) | |
| A61K 31/4184 | (2006.01) | |
| A61K 31/426 | (2006.01) | |
| A61K 31/433 | (2006.01) | |

(52) U.S. Cl.
CPC .......... *C07D 209/24* (2013.01); *A61K 31/404* (2013.01); *A61K 31/405* (2013.01); *A61K 31/4178* (2013.01); *A61K 31/4184* (2013.01); *A61K 31/426* (2013.01); *A61K 31/433* (2013.01); *C07D 403/12* (2013.01); *C07D 405/12* (2013.01); *C07D 409/12* (2013.01); *C07D 417/12* (2013.01)

(58) Field of Classification Search
CPC ... C07D 209/24; C07D 403/12; C07D 405/12; C07D 409/12; C07D 417/12
See application file for complete search history.

(56) References Cited

U.S. PATENT DOCUMENTS

| | | |
|---|---|---|
| 7,005,445 B2 | 2/2006 | Hangauer, Jr. et al. |
| 7,772,216 B2 | 8/2010 | Hangauer, Jr. et al. |
| 8,088,768 B2 | 1/2012 | Hangauer, Jr. et al. |
| 2003/0166615 A1 | 9/2003 | Hangauer, Jr. et al. |
| 2006/0030544 A1 | 2/2006 | Hangauer, Jr. et al. |
| 2011/0028474 A1 | 2/2011 | Hangauer, Jr. et al. |
| 2014/0179735 A1 | 6/2014 | Zhang et al. |

FOREIGN PATENT DOCUMENTS

| | | |
|---|---|---|
| CA | 2464214 A1 | 1/2003 |
| CA | 2464214 C | 2/2011 |
| CN | 1035615732464214 A | 2/2014 |
| EP | 1444204 A1 | 8/2004 |
| JP | 2005514339 A | 5/2005 |
| WO | 03035621 A1 | 5/2003 |
| WO | 2012149048 A1 | 1/2012 |
| WO | 2012149049 A1 | 1/2012 |

OTHER PUBLICATIONS

Li-Fan et al. Antioxidants & Redox Signaling. 2014, 20, 2130-2140.*
He, Rongjun et al., Small molecule tools for functional interrogation of protein tyrosine phosphatases, FIBS Journal, Jan. 2013, (Epub. Aug. 16, 2012), vol. 280, No. 2, pp. 731-750.
Zeng, Li-Fan et al., A Facile Hydroxyindole Carboxylic Acid Based Focused Library Approach for Potent and Selective Inhibitors of Mycobacterium Protein Tyrosine Phosphatase B, ChemMedChem., Jun. 2013 (Epub. Apr. 8, 2013 ), vol. 8, No. 6, pp. 904-908.
Zhang, Xian et al., Salicylic Acid Based Small Molecule Inhibitor for the Oncogenic Src Homology-2 Domain Containing Protein Tyrosine Phosphatase-2 (SHP2), Journal of Medicinal Chemistry, 2010 (Epub. Feb. 19, 2010), vol. 53, No. 6, pp. 2482-2493.

* cited by examiner

*Primary Examiner* — Matthew Coughlin
(74) *Attorney, Agent, or Firm* — Stinson Leonard Street LLP

(57) ABSTRACT

Inhibitors of protein tyrosine phosphatases are disclosed. The inhibitors include hydroxyindole carboxylic acids having a linker and an amine scaffold that are potent inhibitors of Src homology 2-domain containing protein tyrosine phosphatase-2.

20 Claims, 21 Drawing Sheets

IIB08: Shp2 (IC$_{50}$=5.5 μM)
3 Fold Selectivity to
Shp1 and PTP1B a, L = (CH$_2$)$_3$
b, L = m-Phenyl
c, L = p-Phenyl
7'a-c Conditions: (a) Pd(PPh$_3$)$_2$Cl$_2$, CuI, Et$_3$N, DMF, 80-90%; (b) I$_2$, NaHCO$_3$, CH$_2$Cl$_2$ or AcCN, rt, 80-90%; (c) 5% LiOH, MeOH/THF/H$_2$O, 80 deg., 2 h, 80-90%; (d) 192 amines, HOBT, HBTU, DIPEA, DMF, rt, overnight. 60-80%.

HYDROXYINDOLE CARBOXYLIC ACID BASED INHIBITORS FOR ONCOGENIC SRC HOMOLOGY-2 DOMAIN CONTAINING PROTEIN TYROSINE PHOSPHATASE-2 (SHP2)

CROSS-REFERENCE TO RELATED APPLICATIONS

This application claims priority to International Publication Number WO 2014/176488, filed on Apr. 25, 2014, which claims priority to U.S. Provisional Patent Application No. 61/816,404 filed on Apr. 26, 2013 the disclosures of which are incorporated by reference in their entireties.

STATEMENT OF GOVERNMENT SUPPORT

This invention was made with government support under CA152194 awarded by the National Institutes of Health. The government has certain rights in the invention.

BACKGROUND OF THE DISCLOSURE

The present disclosure relates generally to inhibitors of protein tyrosine phosphatases (PTPs). More particularly, the present disclosure relates to hydroxyindole carboxylic acid based inhibitors of oncogenic Src homology-2 domain containing protein tyrosine phosphatase-2 (SHP2).

Protein tyrosine phosphatases (PTPs) play important roles in the regulation of numerous kinds of cellular processes, such as cell growth, proliferation, cellular differentiation and oncogenic transformation. The balance between dephosphorylation by protein tyrosine phosphatase (PTP) and phosphorylation by its counter-part, tyrosine kinase, is crucial for normal physiological function. PTPs are increasingly viewed as valuable drug targets. For example, the Src homology 2 (SH2)-domain containing protein tyrosine phosphatase-2 (SHP2), encoded by tyrosine-protein phosphatase non-receptor type 11 (PTPN11), is a non-receptor protein tyrosine phosphatase (PTP) containing two tandem Src homology-2 (SH2) domains. SHP2 is widely expressed in most tissues and plays a positive role in various signaling transduction pathways downstream of growth factor and cytokine receptors to regulate a diversity of cell functions. The catalytic activity of SHP2 is required for full activation of the Ras-ERK1/2 cascade that is mediated through SHP2-catalyzed dephosphorylation of substrates that are negatively regulated by tyrosine phosphorylation. SHP2 is recognized as a bona fide oncogene; gain-of-function SHP2 mutations leading to increased phosphatase activity-caused Noonan syndrome, as well as multiple forms of leukemia (e.g., juvenile myelomonocytic leukemia, acute myeloid leukemia, myelodysplastic syndrome, acute lymphoid leukemia) and various kinds of solid tumors (e.g., lung adenocarcinoma, colon cancer, neuroblastoma, glioblastoma, melanoma, hepatocellular carcinoma, and prostate cancer). Accordingly, SHP2 represents a promising target for multiple cancers (e.g., triple-negative and HER2+ breast cancer, cancers caused by abnormal activation of receptor protein tyrosine kinases (PTKs), some of which respond poorly to kinase inhibitor monotherapy) and draws increasing interest in the development of SHP2 inhibitors.

The highly positive and conserved charged PTP active site presents a tremendous challenge for the development of potent and selective PTP inhibitors bearing an optimal pharmacological property. Notably, it has been recognized that the binding affinity between pTyr and PTP active site is modest. Furthermore, with regard to PTP substrate recognition, both the pTyr and its flanking residues together make significant contributions. Therefore, a highly efficient strategy for PTP inhibitor discovery was proposed to bind both the active site and nearby non-conserved pocket with a linker to increase activity and selectivity. Large numbers of potent and selective PTP inhibitors have been reported using this strategy. Most of the PTP inhibitors reported are pTyr mimetics, which usually bear two or more acid groups. The poly negative charge properties of these previously produced inhibitors, however, result in these inhibitors lacking cell membrane permeability and are thus not drug-like.

Previously, hydroxyindole carboxylic acid was identified as a pTyr mimic. Moreover, the cellular effective inhibitor IIB08, the structure shown in FIG. 1 and having an $IC_{50}$ of 5.5 µM for SHP2, was identified and determined to have 3-fold selectivity for SHP1 and PTP1B. Furthermore, IIB08 blocked growth factor stimulated ERK1/2 activation and hematopoietic progenitor proliferation. Encouragingly, treatment of leukemic mice with IIB08 and PI3Kinase inhibitor, LY294002, significantly prolonged the survival of mice compared to mice treated with either inhibitor alone in vivo. Despite the efficacious cellular activity and favorable in vivo anti-leukemia ability, the potency of IIB08 is still at greater than 1.0 µM level. Accordingly, there exists a need to develop improved hydroxyindole carboxylic acid compounds for inhibiting PTPs.

BRIEF DESCRIPTION OF THE DISCLOSURE

The present disclosure is generally related to inhibitors of protein tyrosine phosphatases (PTPs). More particularly, the present disclosure relates to hydroxyindole carboxylic acid based inhibitors for oncogenic Src homology-2 domain containing protein tyrosine phosphatase-2 (SHP2). In some embodiments, the inhibitors have an $IC_{50}$ value of less than 1 µM, and in some embodiments, have an $IC_{50}$ value of 0.20 µM for SHP2, which is over 5-fold more selective than any of the over 20 previously tested PTPs.

In one aspect, the present disclosure is directed to a hydroxyindole carboxylic acid for inhibiting a protein tyrosine phosphatase. The hydroxyindole carboxylic acid comprises formula (I):

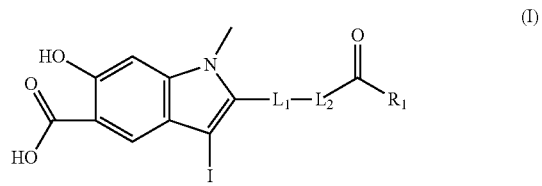

wherein $L_1$ is selected from the group consisting of a single bond, —($C_{1-6}$ alkyl)-, —($C_{2-6}$ alkenyl)-, —($C_{0-6}$ alkyl)-($C_{3-6}$ cycloalkyl)-($C_{0-6}$ alkyl)-, o-phenyl, m-phenyl, p-phenyl, a 3-7 member single aromatic or aliphatic ring, an unsubstituted or substituted fused 5-12 member aromatic or aliphatic ring system, wherein the substitution is selected from the group consisting of nitrogen, oxygen and sulfur;

$L_2$ is selected from the group consisting of a bond,

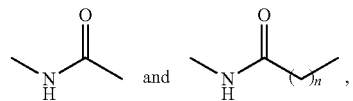

wherein n is 0-3; and R₁=NRaRb, wherein Ra or Rb can each independently be selected from the group consisting of hydrogen, unsubstituted or substituted alkyl, unsubstituted or substituted cycloalkyl, unsubstituted or substituted heterocyclyl, unsubstituted or substituted aryl, unsubstituted or substituted heteroaryl, and unsubstituted or substituted fused 5-12 member aromatic or aliphatic ring system, wherein the substitution on the fused 5-12 member aromatic or aliphatic ring system is selected from the group consisting of nitrogen, oxygen and sulfur.

In another aspect, the present disclosure is directed to a hydroxyindole carboxylic acid for inhibiting a protein tyrosine phosphatase, the hydroxyindole carboxylic acid comprising formula (II):

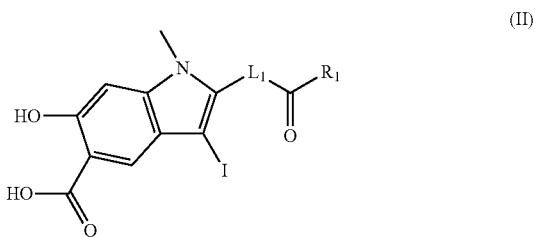

(II)

wherein L₁ is selected from the group consisting of a single bond, —($C_{1-6}$ alkyl)-, —($C_{2-6}$ alkenyl)-, —($C_{0-6}$ alkyl)-($C_{3-6}$ cycloalkyl)-($C_{0-6}$ alkyl)-, o-phenyl, m-phenyl, p-phenyl, a 3-7 member single aromatic or aliphatic ring, an unsubstituted or substituted fused 5-12 member aromatic or aliphatic ring system, wherein the substitution is selected from the group consisting of nitrogen, oxygen and sulfur; and R₁=NRaRb, wherein Ra or Rb can each independently be selected from the group consisting of hydrogen, unsubstituted or substituted alkyl, unsubstituted or substituted cycloalkyl, unsubstituted or substituted heterocyclyl, unsubstituted or substituted aryl, unsubstituted or substituted heteroaryl, and unsubstituted or substituted fused 5-12 member aromatic or aliphatic ring system, wherein the substitution on the fused 5-12 member aromatic or aliphatic ring system is selected from the group consisting of nitrogen, oxygen and sulfur.

In yet another aspect, the present disclosure is directed to a hydroxyindole carboxylic acid for inhibiting a protein tyrosine phosphatase, the hydroxyindole carboxylic acid comprising formula (III):

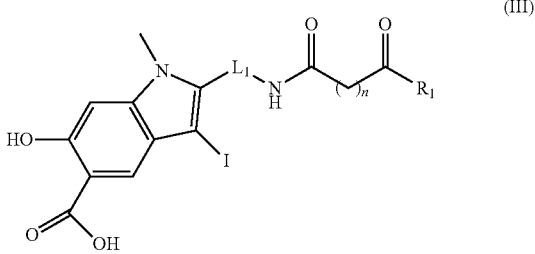

(III)

wherein L₁ is selected from the group consisting of a single bond, —($C_{1-6}$ alkyl)-, —($C_{2-6}$ alkenyl)-, —($C_{0-6}$ alkyl)-($C_{3-6}$ cycloalkyl)-($C_{0-6}$ alkyl)-, o-phenyl, m-phenyl, p-phenyl, a 3-7 member single aromatic or aliphatic ring, an unsubstituted or substituted fused 5-12 member aromatic or aliphatic ring system, wherein the substitution is selected from the group consisting of nitrogen, oxygen and sulfur; n is 0-3; and R₁=NRaRb, wherein Ra or Rb can each independently be selected from the group consisting of hydrogen, unsubstituted or substituted alkyl, unsubstituted or substituted cycloalkyl, unsubstituted or substituted heterocyclyl, unsubstituted or substituted aryl, unsubstituted or substituted heteroaryl, and unsubstituted or substituted fused 5-12 member aromatic or aliphatic ring system, wherein the substitution on the fused 5-12 member aromatic or aliphatic ring system is selected from the group consisting of nitrogen, oxygen and sulfur.

In another aspect, the present disclosure is directed to a hydroxyindole carboxylic acid for inhibiting a protein tyrosine phosphatase, the hydroxyindole carboxylic acid comprising formula (IV):

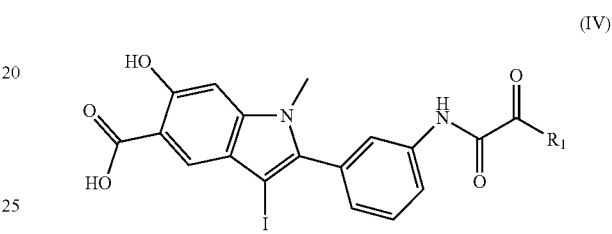

(IV)

wherein R₁=NRaRb, wherein Ra or Rb can each independently be selected from the group consisting of hydrogen, unsubstituted or substituted alkyl, unsubstituted or substituted cycloalkyl, unsubstituted or substituted heterocyclyl, unsubstituted or substituted aryl, unsubstituted or substituted heteroaryl, and unsubstituted or substituted fused 5-12 member aromatic or aliphatic ring system, wherein the substitution on the fused 5-12 member aromatic or aliphatic ring system is selected from the group consisting of nitrogen, oxygen and sulfur.

In another aspect, the present disclosure is directed to a hydroxyindole carboxylic acid for inhibiting a protein tyrosine phosphatase, the hydroxyindole carboxylic acid comprising formula (V):

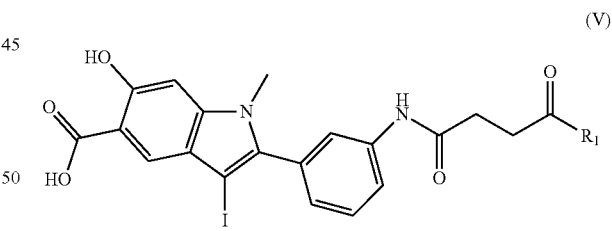

(V)

wherein R₁=NRaRb, wherein Ra or Rb can each independently be selected from the group consisting of hydrogen, unsubstituted or substituted alkyl, unsubstituted or substituted cycloalkyl, unsubstituted or substituted heterocyclyl, unsubstituted or substituted aryl, unsubstituted or substituted heteroaryl, and unsubstituted or substituted fused 5-12 member aromatic or aliphatic ring system, wherein the substitution on the fused 5-12 member aromatic or aliphatic ring system is selected from the group consisting of nitrogen, oxygen and sulfur.

In yet another aspect, the present disclosure is directed to a hydroxyindole carboxylic acid for inhibiting a protein tyrosine phosphatase, the hydroxyindole carboxylic acid comprising formula (VI):

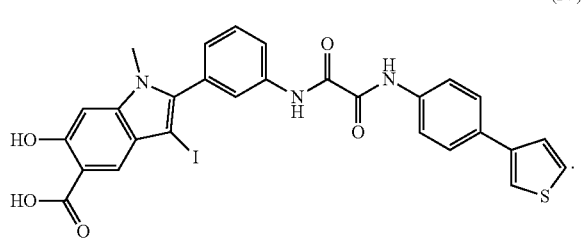
(IV)

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIG. 4A depicts the overall structure of SHP2 in complex with 11c-9. Compound 11c-9 is shown in stick model with unbiased Fo-Fc map contoured at 2.5σ calculated before the ligand and water molecules were added to the model. FIG. 4B depicts the detailed interactions between compound 11c-9 and SHP2. Polar interactions or H-bonds are shown by dashed lines.

FIG. 5A depicts the overall binding mode of 11a-1 with SHP2. The binding modes of II-B08 and 11c-9 from the complex structures were shown for comparison. FIG. 5B depicts the hydroxyindole carboxylic acid motif (spheres) penetrating deeply into the SHP2 active site along the pY recognition cleft. FIG. 5C depicts the β-phenyl ring (spheres) forming strong π-π stack interaction with Y279. FIG. 5D depicts the rigid oxalamide linker orienting the phenylthiophene (spheres) to be well sandwiched by R362 and K364. FIG. 5E depicts the interaction details between 11a-1 with SHP2. Residues within 5 Å distance to 11a-1 are shown in stick.

FIG. 6A shows that 11a-1 dose dependently inhibited H1975 proliferation with an IC$_{50}$ of 0.17±0.02 μM. FIG. 6B shows that 11a-1 decreased EGF induced Erk phosphorylation and increased EGF induced paxillin (Y118) phosphorylation in a dose dependent manner. FIG. 6C shows that the structurally related negative control compound 10a failed to block SHP2 dependent signaling at 2 μM. FIG. 6D shows that 11a-1 had no effect on PMA-stimulated Erk1/2 phosphorylation. FIG. 6E shows the ability of 11a-1 to inhibit Erk1/2 activation was blunted in SHP2 knocked down cells.

FIG. 7A depicts SKBR3 cells that were seeded into Matrigel. Their growth was then monitored over 4 days in the presence of vehicle or the indicated concentrations of 11a-1. FIG. 7B depicts recovered cells after 4 days of growth in Matrigel, and the levels of the total and phospho forms of Erk1/2 and Akt measured by immunoblot. The numbers above each panel represent the ratio of phosphor over total protein.

Figure 1:
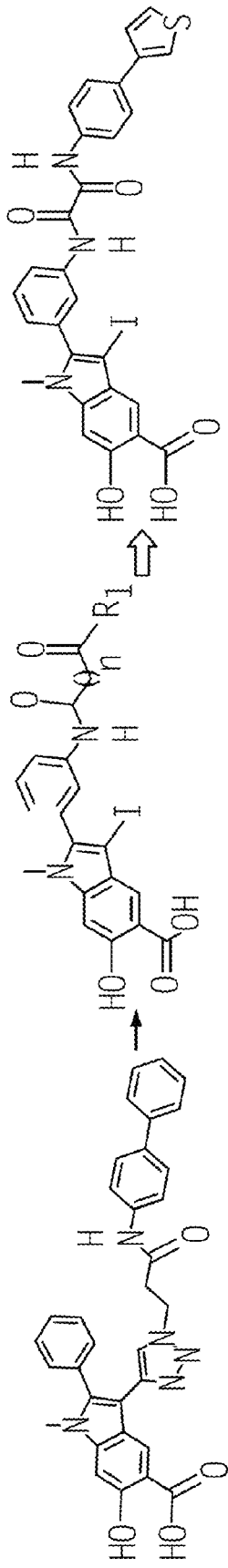
FIG. 1 is a schematic illustrating the strategy and design of the hydroxyindole carboxylic acid based SHP2 inhibitor 11a-1 used in the present disclosure and described in Example 1.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

Targeting protein tyrosine phosphatases (PTPs) for therapeutic development has historically been shrouded with two major challenges. First, the similarities between their active sites (i.e., the pTyr-binding pockets) make it nearly impossible to develop small molecules capable of inhibiting just one of the 100 plus PTPs encoded by the human genome, without inhibiting other closely related family members. Second, finding compounds with high affinity for the positively charged PTP-active site, while at the same time possessing favorable cell permeability, also seems an insurmountable mountain to climb. To enhance both inhibitor potency and selectivity, the present disclosure sought to acquire inhibitor compounds that interact not only with the pTyr-binding pocket but also nearby peripheral sites that are unique to particular PTPs. To further address the bioavailability issue, the present disclosure sought to identify non-hydrolyzable pTyr mimetics that have sufficient polarity to bind the PTP active site, yet are still capable of penetrating cell membranes. It was discovered that bicyclic salicylic acids could serve as non-phosphorus-containing pTyr mimetics, and PTP inhibitors carrying a bicyclic salicylic acid scaffold possessed excellent cellular efficacies.

In accordance with the present disclosure, hydroxyindole carboxylic acids have been discovered that surprisingly selectively inhibit PTPs. Suitable PTPs that are selectively inhibited by the hydroxyindole carboxylic acids of the present disclosure include, for example, Src homology-2 domain containing protein tyrosine phosphatase 2 (SHP2), protein tyrosine phosphatase μ (PTPμ), protein tyrosine phosphatase ε (PTPε), protein tyrosine phosphatase α (PTPα), protein tyrosine phosphatase σ (PTPσ), protein tyrosine phosphatase γ (PTPγ), cytosolic protein tyrosine phosphatases, protein tyrosine phosphatase 1B (PTP1B), lymphoid protein tyrosine phosphatase (Lyp), Src homology-2 domain containing protein tyrosine phosphatase 1 (SHP1), protein tyrosine phosphatase H1 (PTPH1), hematopoietic tyrosine phosphatase (HePTP), Striatal-enriched protein tyrosine phosphatase (STEP), and protein tyrosine phosphatase PEZ, the dual specificity phosphatase, vaccinia H1-related phosphatase (VHR), VH1-like phosphatase Z (VHZ), MAP kinase phosphatase 5 (MKP5), protein phosphatase CDC14A, ubiquitin-like domain-containing CTD phosphatase 1 (UBLCP1) and laforin, low molecular weight PTP (LMWPTP) and protein phosphatase SSu72.

More particularly, the hydroxyindole carboxylic acids of the present disclosure have been found to specifically inhibit protein tyrosine phosphatases with an $IC_{50}$ of from about 0.2 µM to about 100 µM, including from about 2 µM to about 56 µM, including from about 4.5 µM to about 20 µM, and also including from about 0.2 µM to about 16 µM, and from about 2 µM to about 10 µM. In particularly suitable embodiments, the hydroxyindole carboxylic acids have been found to specifically inhibit protein tyrosine phosphatases with an $IC_{50}$ of less than 1 µM, including from about 0.2 µM to less than 1 µM, including from about 0.2 µM to about 0.7 µM, including from about 0.2 µM to about 0.5 µM, and including about 0.25 µM.

Generally, the present disclosure is directed to hydroxyindole carboxylic acids including a linker at position 2 and an amine scaffold.

Suitable linkers include aliphatic and aromatic linkers, such as is shown in formula I below. In one particular embodiment, the linker is an aromatic oxalic linker.

Figure 3A:
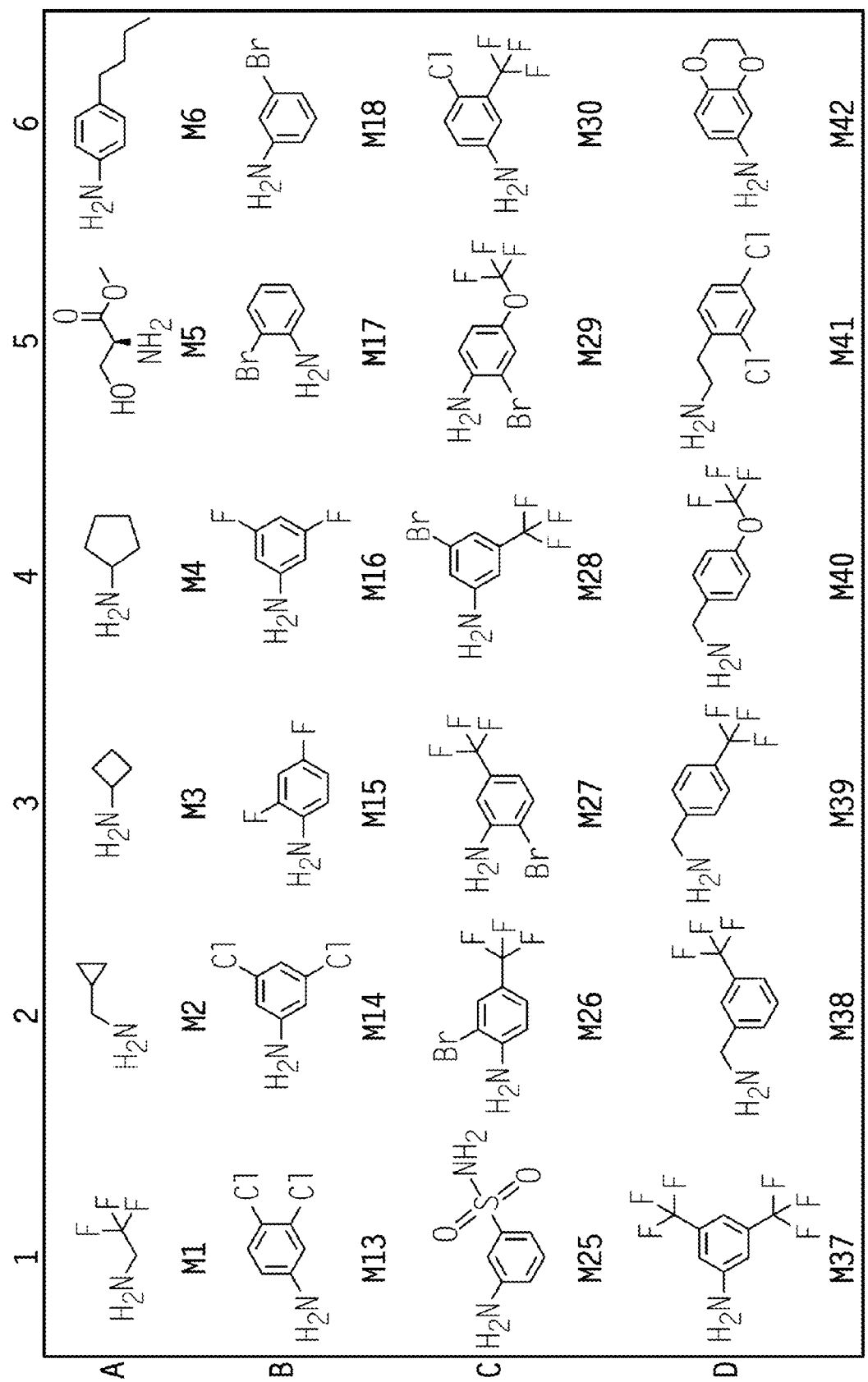
FIGS. 3A and 3B depict exemplary amine scaffolds for use with the hydroxyindole carboxylic acids of the present disclosure.
Figure 3A:
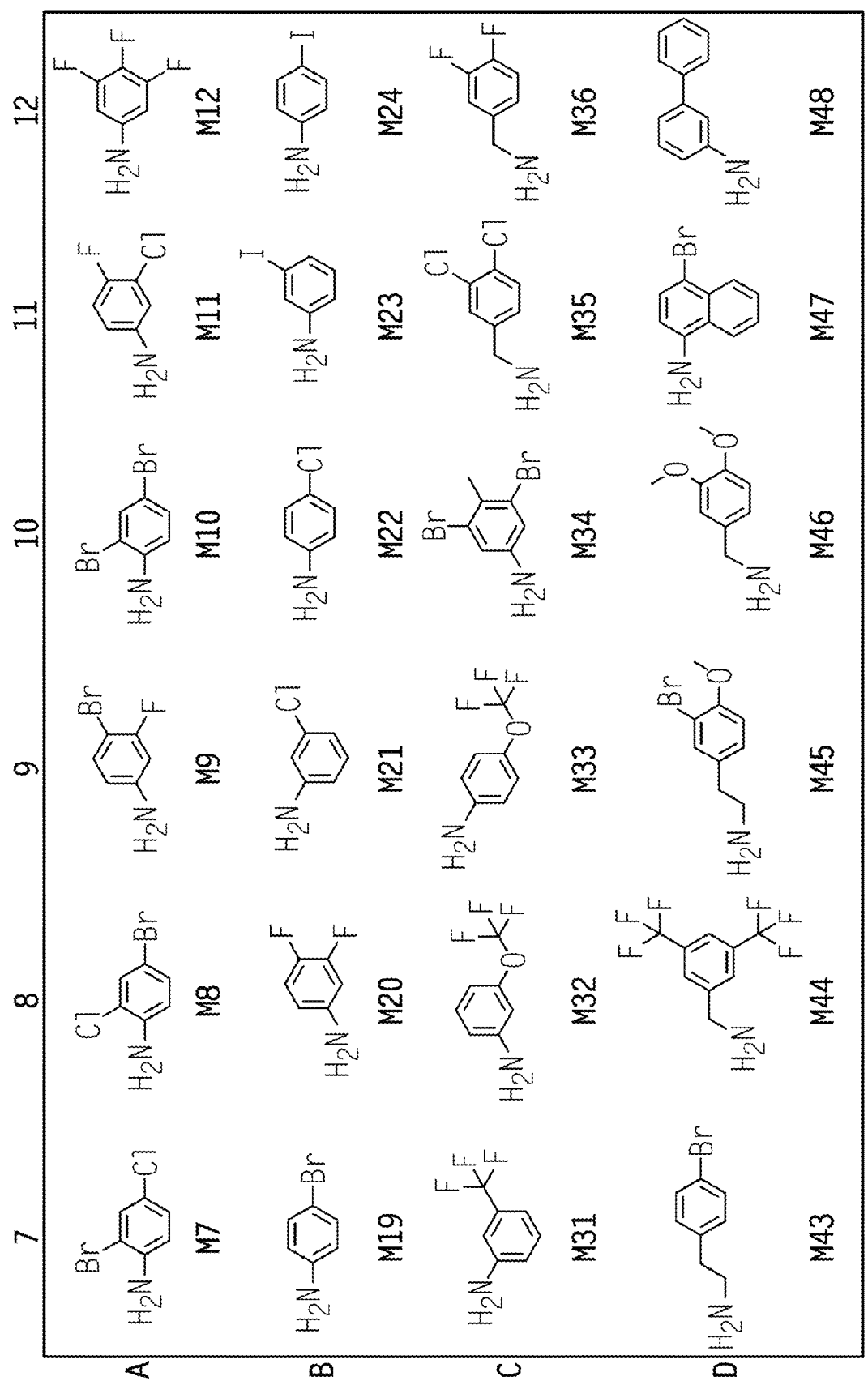
Figure 3A:
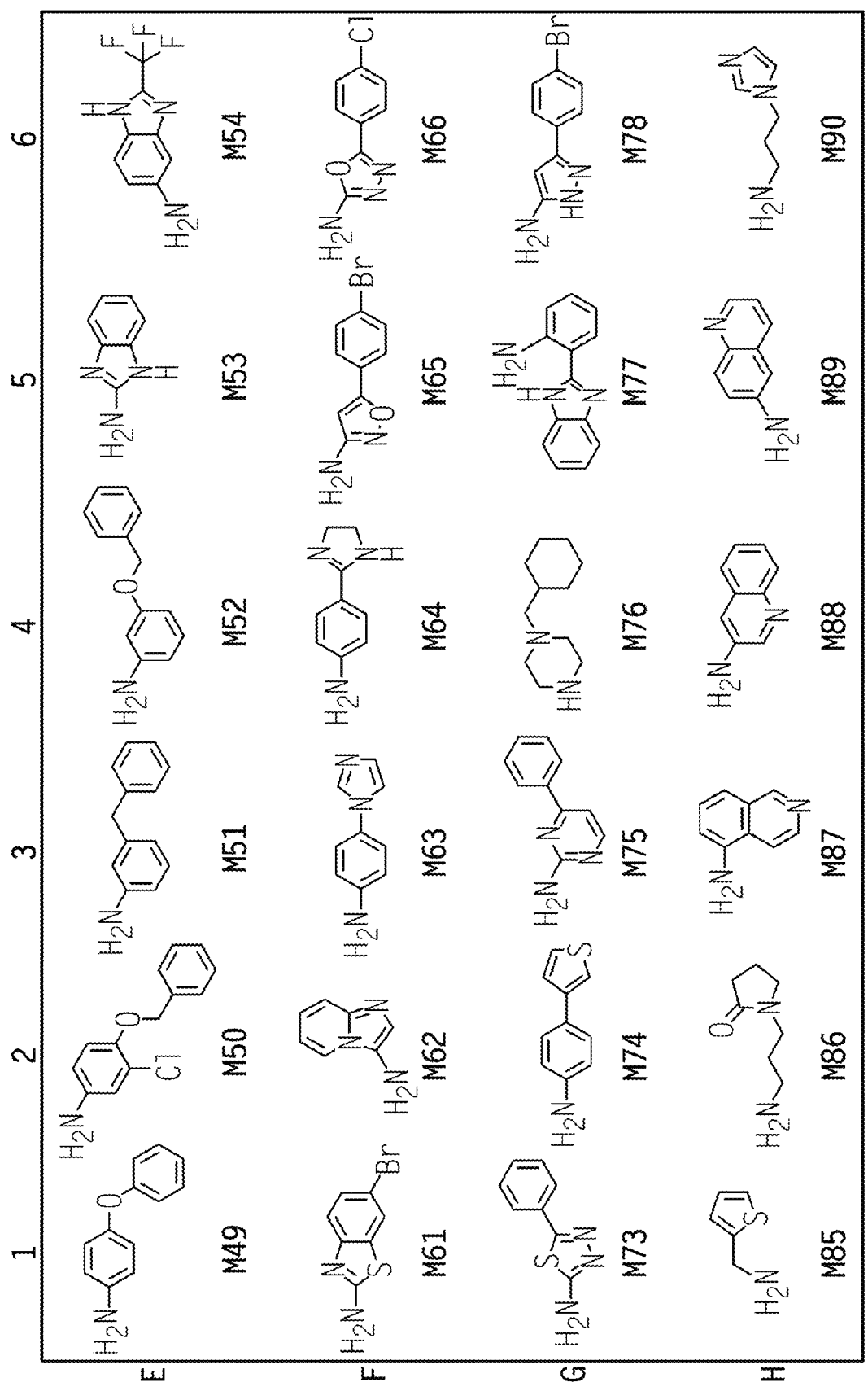
Figure 3A:
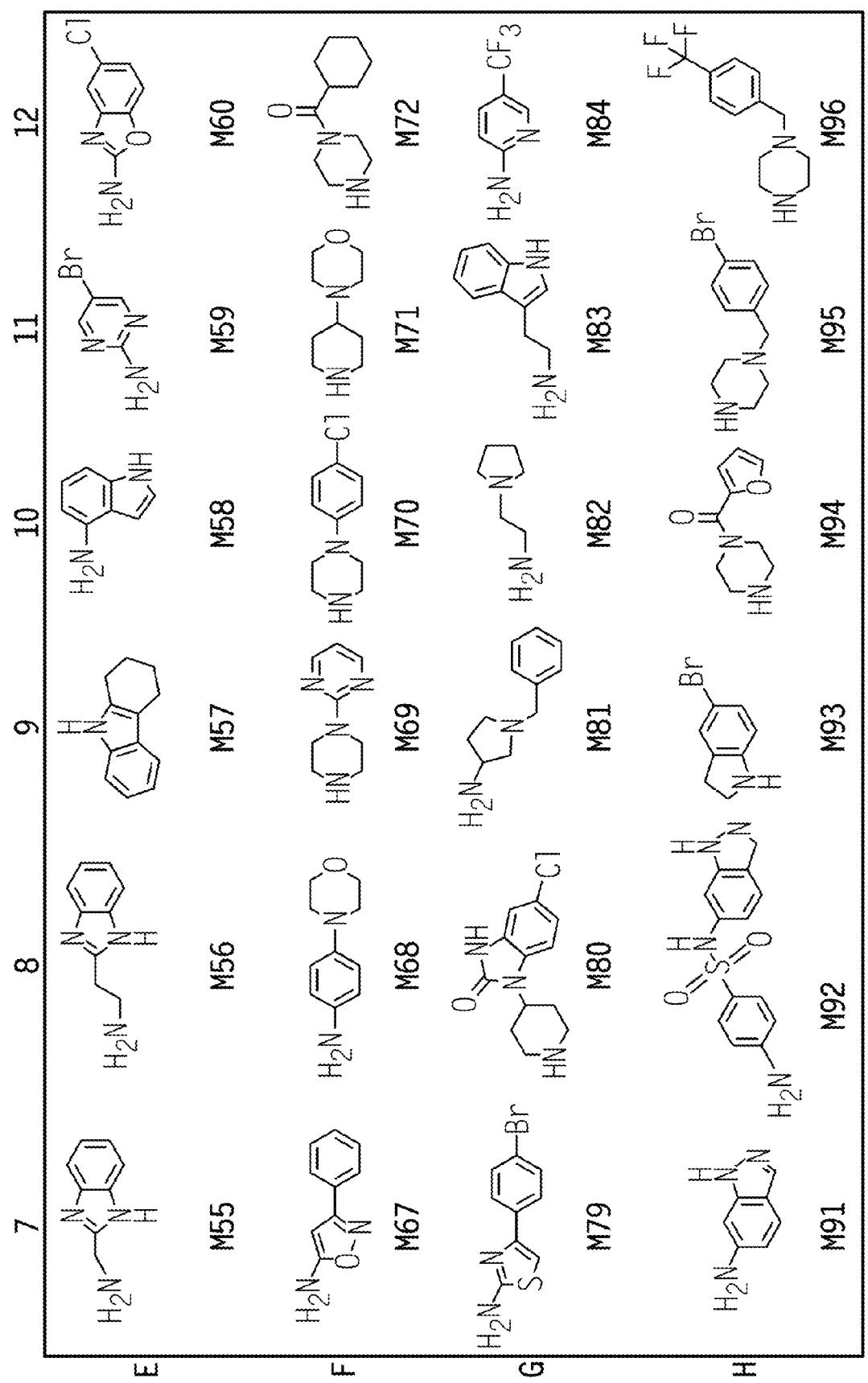
Figure 3B:
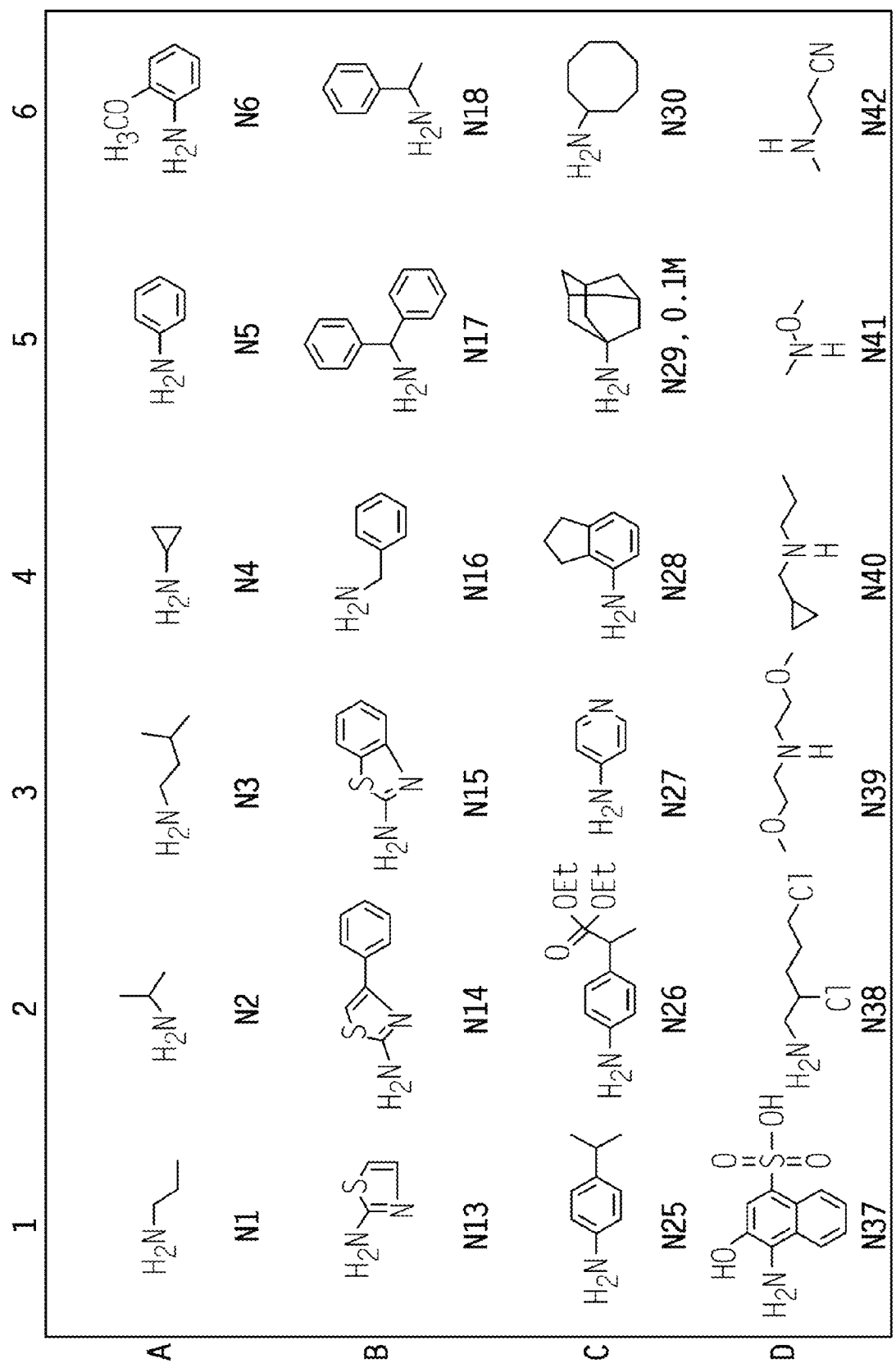
Figure 3B:
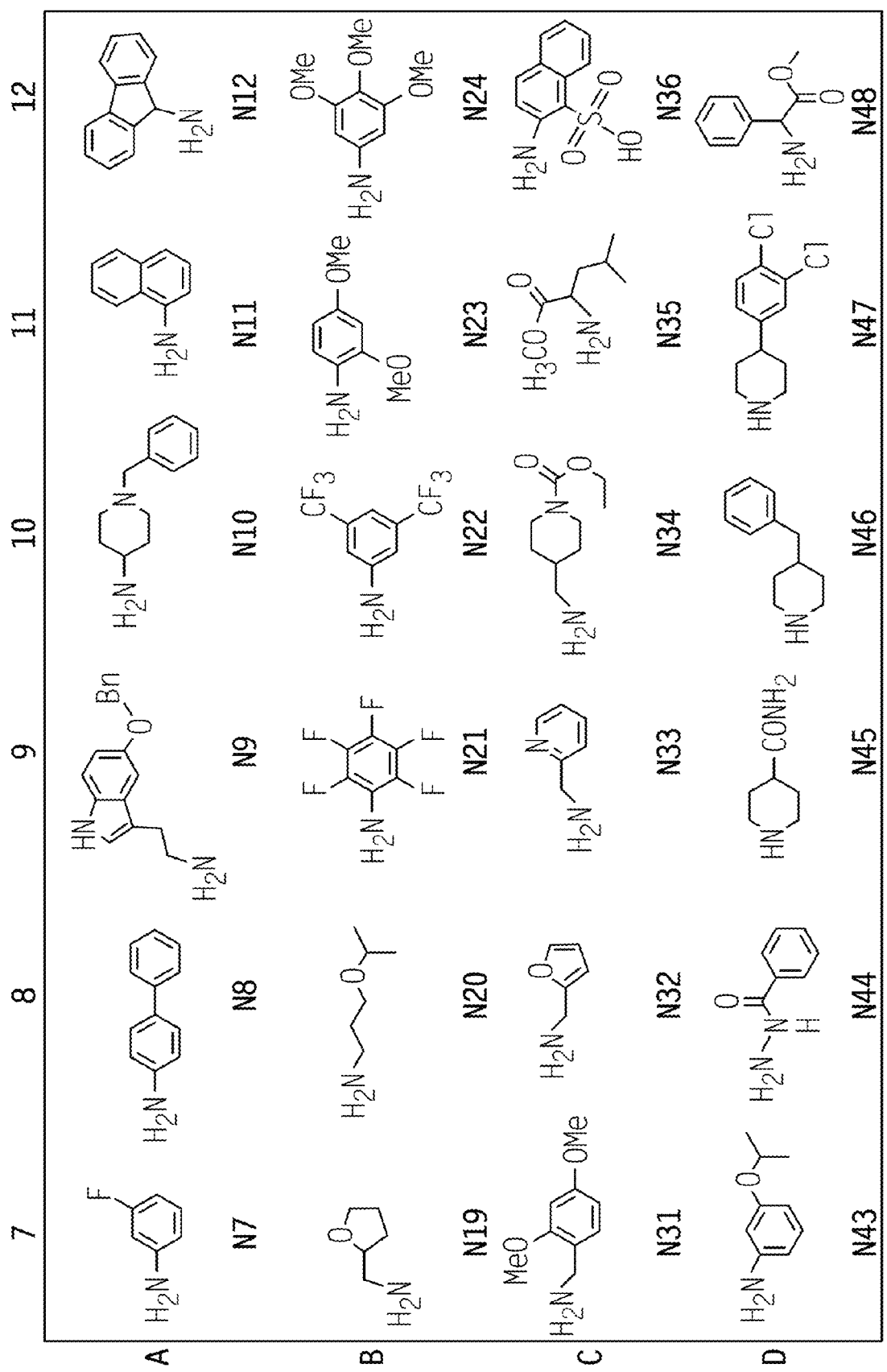
Figure 3B:
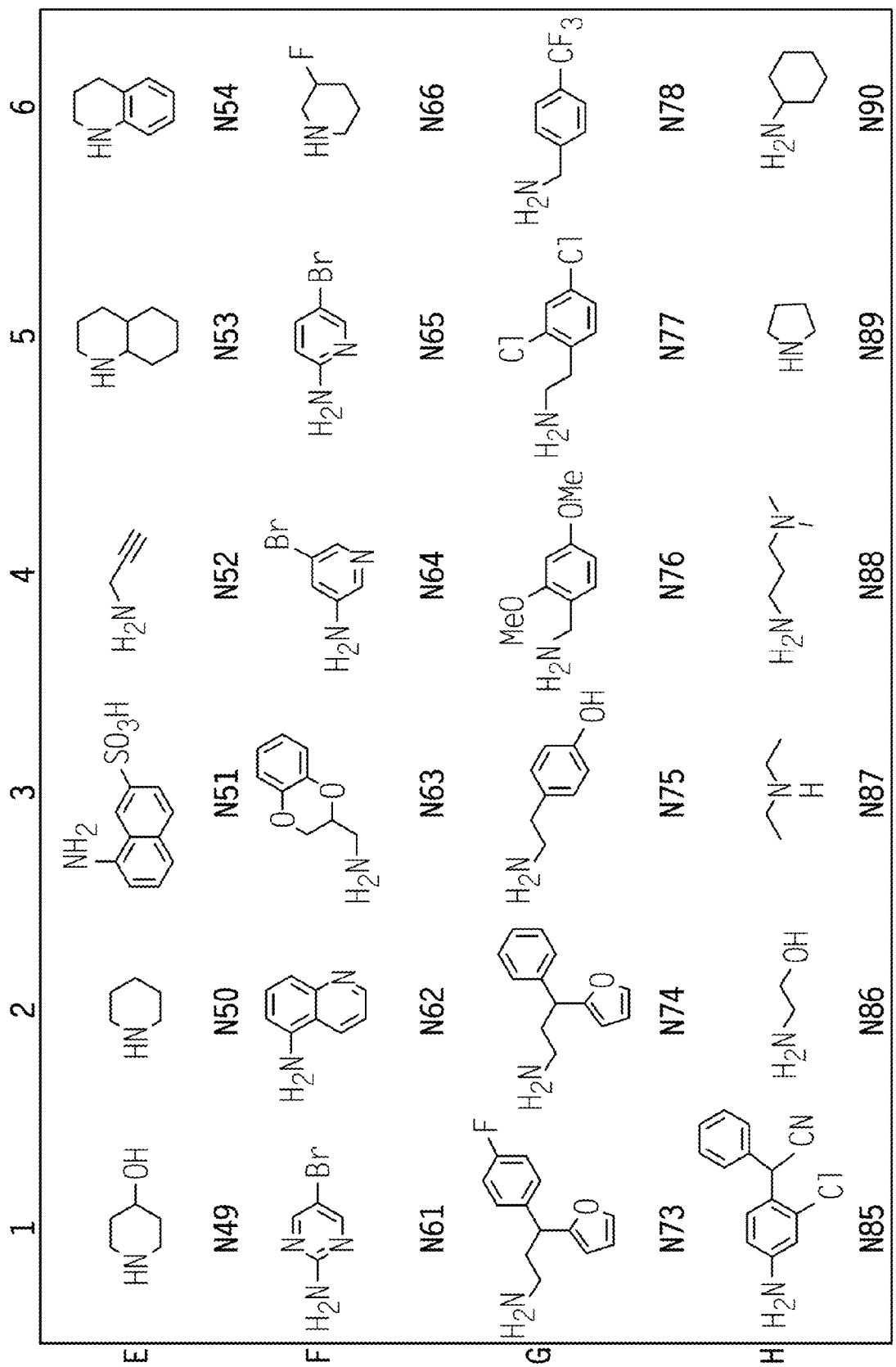
Figure 3B:
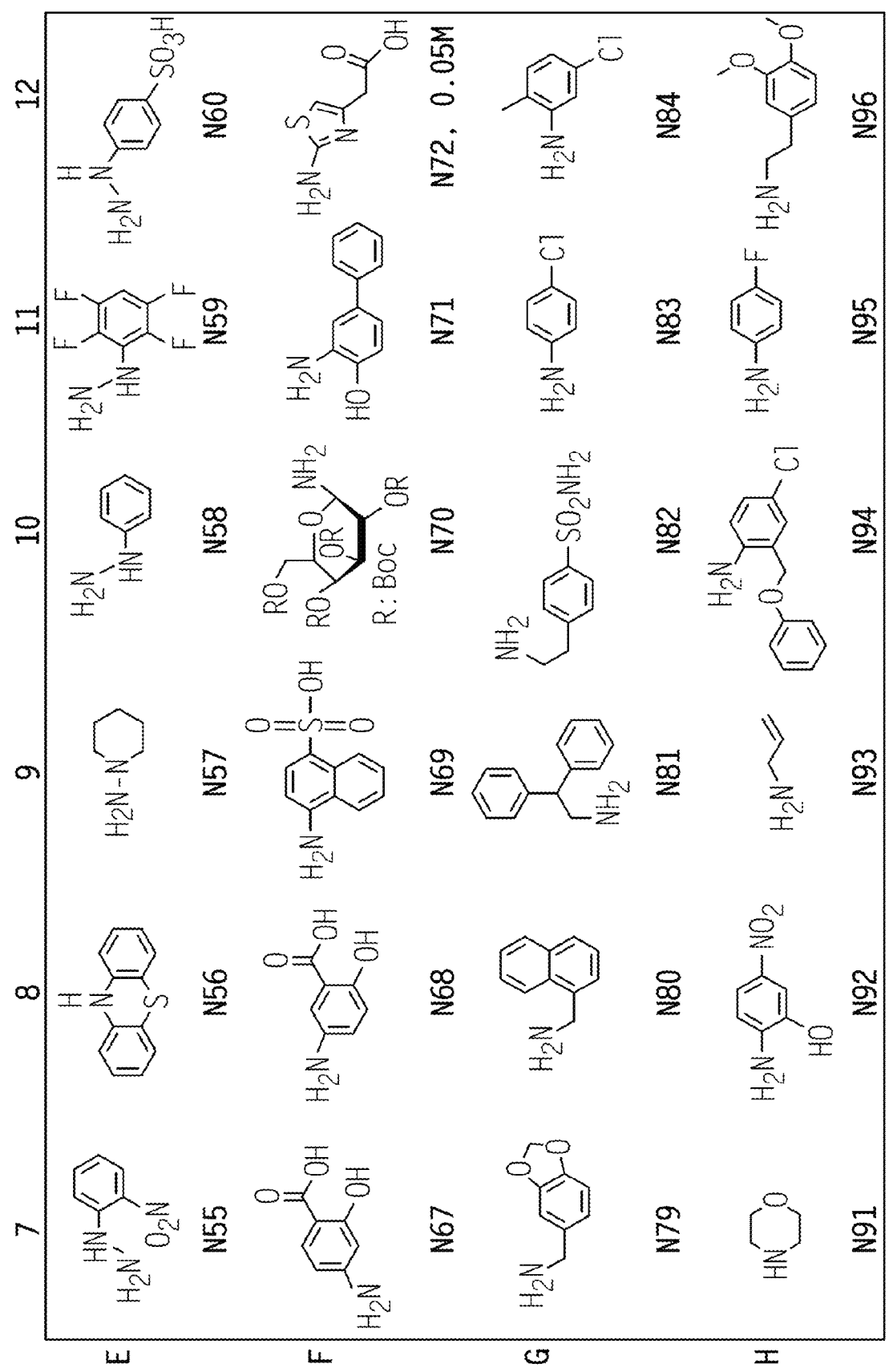

Suitable amine scaffolds include those shown in FIGS. 3A and 3B.

In one aspect, the present disclosure is directed to a hydroxyindole carboxylic acid of formula (I):

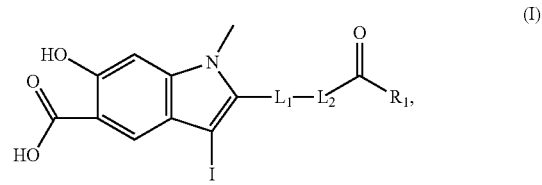

wherein the linker includes L1 and L2. $L_1$ can be a single bond, —($C_{1-6}$ alkyl)-, —($C_{2-6}$ alkenyl)-, —($C_{0-6}$ alkyl)-($C_{3-6}$ cycloalkyl)-($C_{0-6}$ alkyl)-, o-phenyl, m-phenyl, p-phenyl, a 3-7 member single aromatic or aliphatic ring, an unsubstituted or substituted fused 5-12 member aromatic or aliphatic ring system, wherein the substitution is selected from the group consisting of nitrogen, oxygen and sulfur. $L_2$ can be selected from a bond,

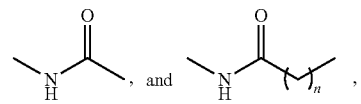

wherein n can range from 0 to 3. $R_1$=NRaRb, wherein Ra or Rb can each independently be selected from the group consisting of hydrogen, unsubstituted or substituted alkyl, unsubstituted or substituted cycloalkyl, unsubstituted or substituted heterocyclyl, unsubstituted or substituted aryl, unsubstituted or substituted heteroaryl, and unsubstituted or substituted fused 5-12 member aromatic or aliphatic ring system, wherein the substitution on the fused 5-12 member aromatic or aliphatic ring system is selected from the group consisting of nitrogen, oxygen and sulfur.

In another aspect, the present disclosure is directed to a hydroxyindole carboxylic acid of formula (II):

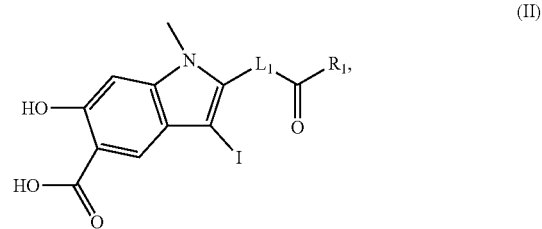

wherein $L_1$ can be a single bond, —($C_{1-6}$ alkyl)-, —($C_{2-6}$ alkenyl)-, —($C_{0-6}$ alkyl)-($C_{3-6}$ cycloalkyl)-($C_{0-6}$ alkyl)-, o-phenyl, m-phenyl, p-phenyl, a 3-7 member single aromatic or aliphatic ring, an unsubstituted or substituted fused 5-12 member aromatic or aliphatic ring system, wherein the substitution is selected from the group consisting of nitrogen, oxygen and sulfur, and $R_1$=NRaRb, wherein Ra or Rb can each independently be selected from the group consisting of hydrogen, unsubstituted or substituted alkyl, unsubstituted or substituted cycloalkyl, unsubstituted or substituted heterocyclyl, unsubstituted or substituted aryl, unsubstituted or substituted heteroaryl, and unsubstituted or substituted fused 5-12 member aromatic or aliphatic ring system, wherein the substitution on the fused 5-12 member aromatic or aliphatic ring system is selected from the group consisting of nitrogen, oxygen and sulfur.

Exemplary hydroxyindole carboxylic acids of formula (II) selectively inhibit protein tyrosine phosphatases as shown in Table 1.

TABLE 1

IC$_{50}$ values (μm) of hydroxyindole carboxylic acid of formula (II) (7'a (L89) and 7'c (L95)) for SHP2.

| ID | R$_1$ | IC$_{50}$ (μM) |
|---|---|---|
| 7'a (Core 89) | OH | >20 |
| 7'a-1 (L89M52) | 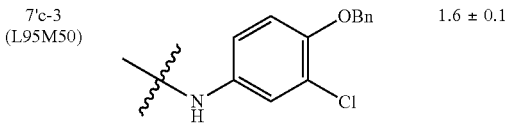 | 5.0 ± 0.3 |
| 7'a-2 (L89N79) | | 12.6 ± 2.8 |
| 7'a-3 (L89M50) | | >20 |

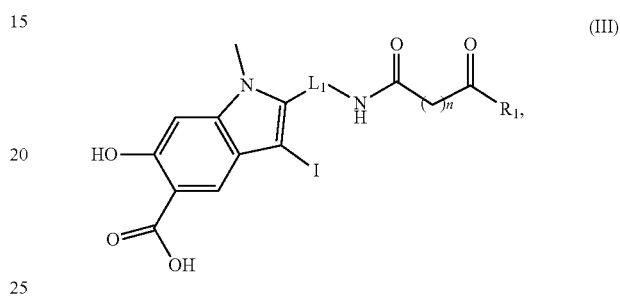

| ID | R$_1$ | IC$_{50}$ (μM) |
|---|---|---|
| 7'c (Core 95) | OH | 9.2 ± 0.5 |
| 7'c-1 (L95M52) | | 2.4 ± 0.1 |
| 7'c-2 (L95N79) | | 4.2 ± 0.2 |

TABLE 1-continued

IC$_{50}$ values (μm) of hydroxyindole carboxylic acid of formula (II) (7'a (L89) and 7'c (L95)) for SHP2.

| 7'c-3 (L95M50) | 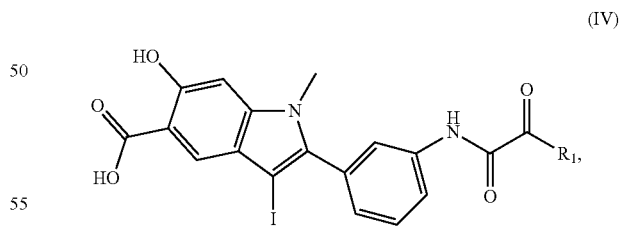 | 1.6 ± 0.1 |
|---|---|---|

In another aspect, the present disclosure is directed to a hydroxyindole carboxylic acid of formula (III):

(III)

wherein, the L$_1$ a single bond, —(C$_{1-6}$ alkyl)-, —(C$_{2-6}$ alkenyl)-, —(C$_{0-6}$ alkyl)-(C$_{3-6}$ cycloalkyl)-(C$_{0-6}$ alkyl)-, o-phenyl, m-phenyl, p-phenyl, a 3-7 member single aromatic or aliphatic ring, an unsubstituted or substituted fused 5-12 member aromatic or aliphatic ring system, wherein the substitution is selected from the group consisting of nitrogen, oxygen and sulfur; n can range from 0 to 3; and R$_1$=NRaRb, wherein Ra or Rb can each independently be selected from the group consisting of hydrogen, unsubstituted or substituted alkyl, unsubstituted or substituted cycloalkyl, unsubstituted or substituted heterocyclyl, unsubstituted or substituted aryl, unsubstituted or substituted heteroaryl, and unsubstituted or substituted fused 5-12 member aromatic or aliphatic ring system, wherein the substitution on the fused 5-12 member aromatic or aliphatic ring system is selected from the group consisting of nitrogen, oxygen and sulfur.

In another aspect, the present disclosure is directed to a hydroxyindole carboxylic acid of formula (IV):

(IV)

wherein R$_1$=NRaRb, wherein Ra or Rb can each independently be selected from the group consisting of hydrogen, unsubstituted or substituted alkyl, unsubstituted or substituted cycloalkyl, unsubstituted or substituted heterocyclyl, unsubstituted or substituted aryl, unsubstituted or substituted heteroaryl, and unsubstituted or substituted fused 5-12 member aromatic or aliphatic ring system, wherein the substitution on the fused 5-12 member aromatic or aliphatic ring system is selected from the group consisting of nitrogen, oxygen and sulfur.

Exemplary hydroxyindole carboxylic acids of formula (IV) selectively inhibit protein tyrosine phosphatases with $IC_{50}$ values as shown in Tables 2 and 3.

TABLE 2

$IC_{50}$ values (µM) of a hydroxyindole carboxylic acid formula (IV) library (11a (L97)) series for SHP2.

[Core structure: 6-hydroxy-5-carboxy-1-methyl-3-iodo-2-(3-aminophenyl)indole with R1 substituent on amide]

| ID | R₁ | IC₅₀ (µM) |
|---|---|---|
| 10a (Core 97) | OH | 14.4 ± 1.8 |
| 11a-1 (L97M74) | NH-(4-(3-thienyl)phenyl) | 0.20 ± 0.02 |
| 11a-2 (L97N08) | NH-(4-biphenyl) | 0.62 ± 0.05 |
| 11a-3 (L97M50) | NH-(3-chloro-4-benzyloxyphenyl) | 0.66 ± 0.03 |
| 11a-4 (L97M61) | NH-(6-bromobenzothiazol-2-yl) | 0.76 ± 0.11 |
| 11a-5 (L97M48) | NH-(3-phenylphenyl) | 0.77 ± 0.15 |
| 11a-6 (L97M52) | NH-(3-benzyloxyphenyl) | 0.86 ± 0.14 |
| 11a-7 (L97M93) | 5-bromoindolin-1-yl | 1.05 ± 0.09 |
| 11a-8 (L97M24) | NH-(4-iodophenyl) | 1.2 ± 0.21 |
| 11a-9 (L97M77) | NH-(2-(1H-benzimidazol-2-yl)phenyl) | 1.25 ± 0.06 |
| 11a-10 (L97N15) | NH-(benzothiazol-2-yl) | 1.35 ± 0.31 |
| 11a-11 (L97M21) | NH-(3-chlorophenyl) | 1.46 ± 0.45 |
| 11a-12 (L97M63) | NH-(4-(1H-imidazol-1-yl)phenyl) | 1.49 ± 0.15 |
| 11a-13 (L97M30) | NH-(4-chloro-3-trifluoromethylphenyl) | 1.76 ± 0.08 |
| 11a-14 (L97M73) | NH-(5-phenyl-1,3,4-thiadiazol-2-yl) | 1.79 ± 0.15 |
| 11a-15 (L97N95) | NH-(4-fluorophenyl) | 1.84 ± 0.09 |
| 11a-16 (L97N13) | NH-(thiazol-2-yl) | 2.31 ± 0.28 |
| 11a-17 (L97M32) | NH-(3-trifluoromethoxyphenyl) | 2.39 ± 0.15 |

TABLE 2-continued

IC$_{50}$ values (μM) of a hydroxyindole carboxylic acid formula (IV) library (11a (L97)) series for SHP2.

| ID | R$_1$ | IC$_{50}$ (μM) |
|---|---|---|
| 11a-18 (L97M18) | 3-Br-phenyl-NH- | 2.73 ± 0.55 |
| 11a-19 (L97N07) | 3-F-phenyl-NH- | 4.66 ± 0.5 |
| 11a-20 (L97M23) | 3-I-phenyl-NH- | 5.42 ± 1.01 |

TABLE 3

IC$_{50}$ values (μM) of 11a-21 to 11a-26 (L97L02-08) series for SHP2.

| ID | R | IC$_{50}$ (μM) |
|---|---|---|
| 11a-1 L97M74 | 4-(3-thienyl)phenyl-NH- | 0.20 ± 0.02 |
| 11a-21 L97L08 | 4'-CN-biphenyl-4-yl-NH- | 0.22 ± 0.01 |
| 11a-22 L97L07 | 3'-CN-biphenyl-4-yl-NH- | 0.31 ± 0.02 |

TABLE 3-continued

IC$_{50}$ values (μM) of 11a-21 to 11a-26 (L97L02-08) series for SHP2.

| ID | R | IC$_{50}$ (μM) |
|---|---|---|
| 11a-23 L97L03 | 2-(5-hydroxymethyl-furan-2-yl)phenyl-NH- | 0.37 ± 0.01 |
| 11a-24 L97L05 | 3-(furan-2-yl)phenyl-NH- | 0.38 ± 0.01 |
| 11a-25 L97L06 | 4'-CN-biphenyl-3-yl-NH- | 0.42 ± 0.02 |
| 11a-26 L97L02 | 3-(thiophen-3-yl)phenyl-NH- | 0.63 ± 0.04 |

In another aspect, the present disclosure is directed to a hydroxyindole carboxylic acid of formula (V):

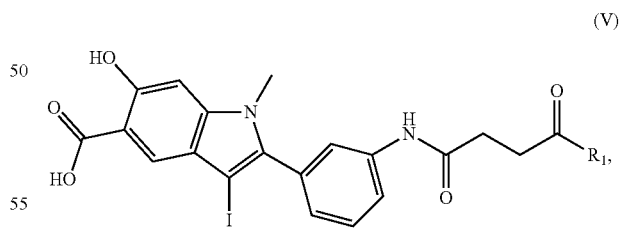

(V)

wherein R$_1$=NRaRb, wherein Ra or Rb can each independently be selected from the group consisting of hydrogen, unsubstituted or substituted alkyl, unsubstituted or substituted cycloalkyl, unsubstituted or substituted heterocyclyl, unsubstituted or substituted aryl, unsubstituted or substituted heteroaryl, and unsubstituted or substituted fused 5-12 member aromatic or aliphatic ring system, wherein the substitution on the fused 5-12 member aromatic or aliphatic ring system is selected from the group consisting of nitrogen, oxygen and sulfur.

Exemplary hydroxyindole carboxylic acids of formula (V) can have an $IC_{50}$ value for SHP2 as shown in Table 4.

TABLE 4

$IC_{50}$ values (μM) of hydroxyindole carboxylic acid of formula (V) library 11c (L88) series for SHP2.

| ID | $R_1$ | $IC_{50}$ (μM) |
|---|---|---|
| 10c (Core 88) | OH | 56 |
| 11c-1 (L88M74) | HN–C6H4–(3-thienyl) | 2.3 ± 0.3 |
| 11c-2 (L88M49) | HN–C6H4–OPh | 3.6 ± 0.3 |
| 11c-3 (L88M50) | NH–C6H3(Cl)–OBn | 5.0 ± 0.9 |
| 11c-4 (L88M52) | NH–C6H4–OBn (meta) | 4.5 ± 1.4 |
| 11c-5 (L88M48) | NH–C6H4–Ph (meta) | 5.3 ± 0.9 |
| 11c-6 (L88M93) | N-(5-bromoindolinyl) | 7.2 ± 0.9 |
| 11c-7 (L88M33) | HN–C6H4–OCF3 | 8.6 ± 2.3 |
| 11c-8 (L88N25) | HN–C6H4–iPr | 10.7 ± 2.4 |
| 11c-9 (L88N79) | NH–CH2–(benzo[1,3]dioxol-5-yl) | 14.0 ± 1.0 |
| 11c-10 (L88N40) | N(propyl)(cyclopropylmethyl) | >20 |
| 11c-11 (L88N13) | HN–(thiazol-2-yl) | 26.0 ± 5.0 |

In another aspect, the present disclosure is directed to a hydroxyindole carboxylic acid of formula (VI):

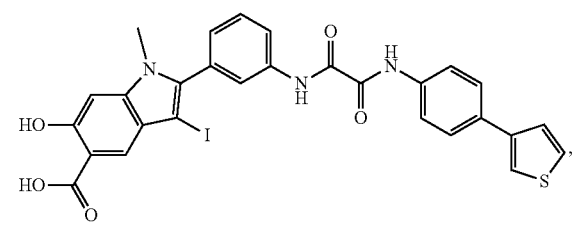

(VI)

As shown in Table 5, the hydroxyindole carboxylic acid of formula (VI) is selective for inhibiting protein tyrosine phosphatases including, for example, SHP2, LYP, mPTPA, SHP1, PTP1B, LMWPTP, VHR and laforin. More particularly, the hydroxyindole carboxylic acid of formula (VI) can have an $IC_{50}$ value for PTPs of from about 0.2 μM to greater than 100 μM, including from about 0.2 μM to less than 1 μM, including from about 0.2 μM to about 0.7 μM, including from about 0.2 μM to about 0.5 μM, and including about 0.25 μM.

TABLE 5

Selectivity of hydroxyindole carboxylic acid of formula (VI) against PTPs.

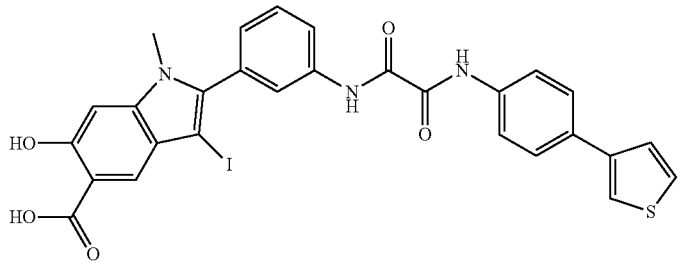 [SMILES: Cn1c(-c2cccc(NC(=O)C(=O)Nc3ccc(-c4ccsc4)cc3)c2)c(I)c2cc(C(=O)O)c(O)cc21]

| PTP | IC$_{50}$ (μM) | PTP | IC$_{50}$ (μM) |
| --- | --- | --- | --- |
| SHP2 | 0.20 ± 0.02 | VHR | 3.19 ± 0.09 |
| LYP | 1.05 ± 0.02 | PTPμ | 3.3 ± 0.2 |
| HePTP | 1.03 ± 0.08 | STEP | 4.0 ± 0.2 |
| PTPH1 | 1.07 ± 0.07 | PEZ | 5.3 ± 0.2 |
| SHP1 | 1.44 ± 0.04 | PTPσ | 8.6 ± 0.4 |
| Ssu72 | 1.3 ± 0.2 | UBLCP1 | 9.7 ± 0.5 |
| PTP1B | 2.29 ± 0.03 | Laforin | 12.16 ± 2 |
| LMWPTP | 2.34 ± 0.02 | CDC14A | 16 ± 4 |
| VHZ | 2.3 ± 0.2 | PTPε | >20 |
| PTPγ | 2.4 ± 0.4 | PTPα | >100 |
| MKP5 | 2.9 ± 0.1 | mPTPA | 1.09 ± 0.04 |

The disclosure will be more fully understood upon consideration of the following non-limiting Examples.

EXAMPLES

The below compounds and methods were used in Examples 1-6.

Materials and General Procedures. para-Nitrophenyl phosphate (pNPP) was purchased from ThermoFisher Scientific (Rockford, Ill.). For organic synthesis, reagents were used as purchased (Aldrich, Acros, Alfa Aesar, TCI), except where noted. Rabbit anti-phospho-Akt, anti-total Akt, anti-phospho-Erk1/2, anti-total Erk1/2, anti-Phospho-Paxillin (Tyr118), and anti-phospho-SHP2 antibodies were purchased from Cell Signaling Technology (Beverly, Mass.). Anti-Paxilin antibodies were from BD Transduction Laboratories. Recombinant murine interleukin-3 (IL-3), murine stem cell factor (SCF), murine thrombopoietin (TPO), murine FLT3 ligand (FLT3-L) were purchased from Peprotech (Rocky Hill, N.J.). Iscove's modified Dulbecco's medium (IMDM) was purchased from Invitrogen (Carlsbad, Calif.). [$^3$H] Thymidine was purchased from PerkinElmer (Boston, Mass.).

General procedures. $^1$H and $^{13}$C NMR spectra were obtained on Brucker 500 spectrometers with TMS or residual solvent as standard. All column chromatography was performed using Dynamic Adsorbents 230-400 mesh silica gel (SiO$_2$) with the indicated solvent system unless otherwise noted. TLC analysis was performed using 254 nm glass-backed plates and visualized using UV light (254 nm), low-resolution mass spectra and purity data were obtained using an Agilent Technologies 6130 Quadrupole LC/MS (Santa Clara, Calif.). The analytical HPLC gradient started at 0% methanol in water and ended at 100% methanol after 8 minutes with 0.1% of TFA. The purity of all final tested compounds was established to be >95% (UV, λ=254 nm). High resolution Mass spectrum data were collected on Agilent 6520 Accurate-Mass Q-TOF LC/MS. HPLC purification was carried out on a Waters Delta 600 (Waters, Milford, Mass.) equipped with a Sunfire Prep C18 OBD column (30 mm*150 mm, 5 μm) with methanol-water (both containing 0.1% TFA) as mobile phase. The preparative HPLC gradient started at 50% methanol in water and ended at 100% methanol after 40 minutes with 0.1% of TFA.

(9H-fluoren-9-yl)methyl (3-ethynylphenyl)carbamate (2). Mixtures of compound 1 (0.75 mL, 7.18 mmol), Fmoc-OSu (2.664 g, 7.89 mmol) in 200 mL of THF were refluxed overnight. The solution was partitioned between EtOAc and water. The residue was purified by flash silica chromatography (Hex/EtOAc=8:1) to afford titled compound as white solid (1.98 g, 81.4%). MP: 137-138° C.; $^1$H NMR (500 MHz, CDCl$_3$): δ 7.83 (m, 2H), 7.61 (m, 2H), 7.54 (brs, 1H), 7.36 (m, 3H), 7.28 (m, 2H), 7.23 (m, 1H), 7.21 (m, 1H), 6.66 (brs, 1H), 4.57 (d, J=6.6 Hz, 2H), 4.30 (t, J=6.6 Hz, 1H), 3.08 (s, 1H); $^{13}$C NMR (125 MHz, DMSO): δ 153.8, 144.1, 141.2, 139.8, 129.6, 128.1, 127.5, 126.2, 125.5, 122.5, 121.5, 120.6, 119.3, 83.5, 80.9, 66.1, 47.0; HRMS (ESI): (M+H)$^+$ calcd for C$_{23}$H$_{18}$NO$_2$: 340.1332. found: 340.1341; LC-MS (ESI): 362.0 (M+Na)$^+$; Purity: >95% (UV, λ=254 nm).

Methyl 5-((3-((((9H-fluoren-9-yl)methoxy)carbonyl)amino)phenyl)ethynyl)-4-(dimethylamino)-2-hydroxybenzoate (4). A mixture of Methyl 4-(dimethylamino)-2-hydroxy-5-iodobenzoate 3 (5.13 g, 16 mmol), compound 2 (6.5 g, 19 mmol), Na$_2$CO$_3$ (2.03 g, 19.2 mmol), bis(triphenylphosphine)palladium(II) chloride (0.576 g, 0.8 mmol) and CuI (304 mg, 1.6 mmol) were loaded in a flask, which was degassed and back-filled with nitrogen. 15 mL DMF were added. The resulting mixture was stirred under a nitrogen atmosphere at room temperature for 4 hours. The reaction was monitored by TLC to establish completion. The solution was partitioned between EtOAc (200 mL) and brine (200 mL). The organic layers were washed with brine (3*200 mL), dried over sodium sulfate and concentrated in vacuum. The residue was purified by flash silica chromatography (Hex/EtOAc=4:1) to afford titled compound as viscous oil (3.74 g, 44%). $^1$H NMR (500 MHz, CDCl$_3$): δ 10.96 (s, 1H), 7.97 (s, 1H), 7.80 (m, 2H), 7.64 (m, 2H), 7.58 (brs, 1H), 7.45 (m, 2H), 7.20-7.31 (m, 6H), 6.72 (brs, 1H), 6.33 (s, 1H), 4.57 (d, J=6.6 Hz, 2H), 4.30 (t, J=6.6 Hz, 1H), 3.93 (s, 3H), 3.15

(s, 6H); $^{13}$C NMR (125 MHz, CDCl$_3$): δ 169.8, 162.6, 159.2, 153.2, 153.2, 143.6, 141.3, 137.8, 137.4, 129.0, 127.8, 127.6, 127.1, 126.1, 124.9, 124.7, 120.7, 120.0, 104.1, 103.9, 102.8, 92.1, 89.0, 66.9, 51.9, 47.1, 42.5; HRMS (ESI): (M+H)$^+$ calcd for C$_{33}$H$_{29}$N$_2$O$_5$: 533.2071, found: 533.2072; LC-MS (ESI): 533.2 (M+H)$^+$, 530.8 (M–H)$^-$; Purity: >95% (UV, λ=254 nm).

Methyl 2-(3-(((((9H-fluoren-9-yl)methoxy)carbonyl)amino)phenyl)-6-hydroxy-3-iodo-1-methyl-1H-indole-5-carboxylate (5). To a solution of 4 (1.72 g, 3.23 mmol), NaHCO$_3$ (0.408 g, 4.85 mmol) in CH$_2$Cl$_2$ (500 mL) was added iodine (1.23 g, 4.85 mmol). The resulting mixture was stirred at room temperature for 4 hours, then added 100 mL CH$_2$Cl$_2$ and washed with saturated aqueous Na$_2$SO$_3$ solution (2×500 mL), brine (500 mL), dried over Na$_2$SO$_4$ and concentrated in vacuum. The residue was purified by flash chromatography (Hexane/THF=1:1) to afford titled compound as colorless solid (1.79 g, 86%). MP: 131-132° C.; $^1$H NMR (500 MHz, CDCl$_3$): δ 10.92 (s, 1H), 8.03 (s, 1H), 7.79 (m, 2H), 7.65 (m, 2H), 7.48 (m, 5H), 7.36 (m, 2H), 7.18 (m, 1H), 6.85 (s, 1H), 6.80 (s, 1H), 4.61 (m, 2H), 4.30 (m, 1H), 4.03 (s, 3H), 3.60 (s, 3H); $^{13}$C NMR (125 MHz, CDCl$_3$): δ 171.2, 158.2, 153.4, 143.6, 142.5, 142.2, 141.3, 137.9, 131.9, 129.2, 127.8, 127.1, 127.0, 125.8, 124.8, 124.3, 124.1, 120.0, 107.6, 96.2, 66.9, 60.0, 52.3, 47.1, 32.1; HRMS (ESI): (M+H)$^+$ calcd for C$_{32}$H$_{26}$IN$_2$O$_5$: 645.0881, found: 645.0851; LC-MS (ESI): 667.0 (M+Na)$^+$; Purity: >95% (UV, λ=254 nm).

Methyl 2-(3-aminophenyl)-6-hydroxy-3-iodo-1-methyl-1H-indole-5-carboxylate (6). Compound 5 (1.79 g, 2.77 mmol) was dissolved in 10 mL of CH$_2$Cl$_2$ and then 10 mL of diethylamine was added to the solution under room temperature for 3 hours. The solution was concentrated in vacuum. The residue was partitioned between CH$_2$Cl$_2$ (200 mL) and brine (200 mL). The organic layer was dried over sodium sulfate and concentrated in vacuum. The residue was purified by flash silica chromatography (CH$_2$Cl$_2$ as elution) to afford titled compound as white solid (1 g, 85.5%). MP: 83-85° C.; $^1$H NMR (500 MHz, CDCl$_3$): δ 10.90 (s, 1H), 8.02 (s, 1H), 7.31 (m, 1H), 6.84 (s, 1H), 6.80 (m, 2H), 6.76 (m, 1H), 4.03 (s, 3H), 3.83 (brs, 2H), 3.60 (s, 3H); $^{13}$C NMR (125 MHz, CDCl$_3$): δ 171.2, 158.1, 146.4, 143.1, 142.4, 132.1, 129.4, 124.2, 124.1, 120.8, 117.1, 115.6, 107.4, 96.1, 59.4, 52.1, 32.1; HRMS (ESI): (M+H)$^+$ calcd for C$_{17}$H$_{16}$IN$_2$O$_3$: 423.0200, found: 423.0190; LC-MS (ESI): 423.0 (M+H)$^+$, 420.8 (M–H)$^-$; Purity: >95% (UV, λ=254 nm).

2-(3-aminophenyl)-6-hydroxy-3-iodo-1-methyl-1H-indole-5-carboxylic acid (7). Compound 6 (1 g, 2.37 mmol) was dissolved in 8 mL of THF. Then, 5% LiOH (4 mL) solution was added. The mixture was heated to 80° C. for 2 hours, cooled to room temperature, diluted by brine (200 mL), acidified by 2 N HCl to pH 5 and extracted with EtOAc (2×200 mL). The organic layers were combined, washed with brine, dried over sodium sulfate and concentrated in vacuum to give titled compound as pale solid (940 mg, 97.2%). Decomposed at 148° C.; $^1$H NMR (500 MHz, DMSO): δ 7.85 (s, 1H), 7.46 (m, 1H), 7.11 (m, 3H), 7.04 (s, 1H), 4.11 (m, 2H), 3.59 (s, 3H); $^{13}$C NMR (125 MHz, DMSO): δ 173.0, 158.3, 142.6, 142.5, 140.9, 132.1, 130.0, 124.5, 124.0, 123.8, 120.9, 119.5, 108.1, 97.0, 60.6, 32.5; HRMS (ESI): (M–H)$^-$ calcd for C$_{16}$H$_{12}$IN$_2$O$_3$: 406.9898, found: 406.9894. LC-MS (ESI): 409.0 (M+H)$^+$, 407.0 (M–H)$^-$; Purity: >95% (UV, λ=254 nm).

General method for the synthesis of 9a-d. Compound 7 (30 mg, 0.074 mmol) was dissolved in 1 mL of DMF under 0° C. and then 1.5 equivalent of corresponding acyl chloride 8a-d was added to the solution for overnight. The solution was partitioned between EtOAc (200 mL) and brine (200 mL). The organic layers were washed with brine (3×200 mL), dried over sodium sulfate and concentrated in vacuum to afford titled compounds as pale solid without purification for further use.

General method for the synthesis of 10a-d. Compound 9a-d (0.074 mmol) was dissolved in 2 mL of THF. Then, 5% LiOH (2 mL) solution was added. The mixture was stirred under room temperature for overnight, acidified by 2 N HCl to pH 5, and extracted with EtOAc (2×200 mL). The organic layers were combined, washed with brine, dried over sodium sulfate and concentrated in vacuum. This crude product was purified by Prep-HPLC to give titled compounds.

2-(3-(carboxyformamido)phenyl)-6-hydroxy-3-iodo-1-methyl-1H-indole-5-carboxylic acid (10a, Core 97). Pale solid (26 mg, 71%, two steps); 1H NMR (500 MHz, DMSO): δ 11.38 (brs, 1H), 10.95 (s, 1H), 7.94 (m, 2H), 7.86 (s, 1H), 7.54 (m, 1H), 7.30 (m, 1H), 7.05 (s, 1H), 3.61 (s, 3H); 13C NMR (125 MHz, DMSO): δ 173.0, 162.4, 158.3, 157.4, 142.5, 142.4, 138.3, 131.5, 129.4, 127.1, 124.0, 123.8, 122.6, 121.1, 108.1, 97.0, 60.8, 32.5; HRMS (ESI): (M–H)– calcd for C18H12IN2O6: 478.9746, found: 478.9762; LC-MS (ESI): 481.0 (M+H)+, 478.8 (M–H)–; Purity: >95% (UV, λ=254 nm).

2-(3-(2-carboxyacetamido)phenyl)-6-hydroxy-3-iodo-1-methyl-1H-indole-5-carboxylic acid (10b, Core 98). Pale solid (30 mg, 82%, two steps); 1H NMR (500 MHz, DMSO): δ 10.37 (s, 1H), 7.86 (s, 1H), 7.74 (m, 2H), 7.50 (m, 1H), 7.21 (m, 1H), 7.04 (s, 1H), 3.61 (s, 3H), 3.40 (s, 2H); HRMS (ESI): (M–H)– calcd for C19H14IN2O6: 492.9902, found: 492.9933; LC-MS (ESI): 495.0 (M+H)+, 492.8 (M–H)–; Purity: >95% (UV, λ=254 nm).

2-(3-(3-carboxypropanamido)phenyl)-6-hydroxy-3-iodo-1-methyl-1H-indole-5-carboxylic acid (10c, Core 88). Pale solid (31 mg, 82%, two steps); 1H NMR (500 MHz, DMSO): δ 12.16 (brs, 1H), 11.36 (brs, 1H), 10.19 (s, 1H), 7.84 (s, 1H), 7.42 (m, 2H), 7.47 (s, 1H), 7.16 (m, 1H), 7.04 (s, 1H), 3.58 (s, 3H), 2.60 (m, 4H); 13C NMR (125 MHz, DMSO): δ 174.2, 173.0, 170.8, 158.3, 142.8, 142.5, 139.9, 131.5, 129.4, 125.4, 123.9, 123.8, 121.2, 119.7, 108.0, 97.1, 60.6, 32.5, 31.5, 29.1; HRMS (ESI): (M–H)– calcd for C20H16IN2O6: 507.0059, found: 507.0080; LC-MS (ESI): 509.0 (M+H)+, 507.0 (M–H)–; Purity: >95% (UV, λ=254 nm).

2-(3-(4-carboxybutanamido)phenyl)-6-hydroxy-3-iodo-1-methyl-1H-indole-5-carboxylic acid (10d, Core 96). Pale solid (21 mg, 54%, two steps); 1H NMR (500 MHz, DMSO): δ 11.38 (brs, 1H), 10.12 (s, 1H), 7.85 (s, 1H), 7.74 (m, 2H), 7.48 (m, 1H), 7.17 (m, 1H), 7.04 (s, 1H), 3.59 (s, 3H), 2.40 (m, 2H), 2.29 (m, 2H), 1.83 (m, 2H); HRMS (ESI): (M–H)– calcd for C21H18IN2O6: 521.0215, found: 520.9139; LC-MS (ESI): 523.0 (M+H)+, 520.8 (M–H)–; Purity: >95% (UV, λ=254 nm).

Procedure for the assembling of Library 11a-d. Compound 10a-d (65 mM, 3 μL) in DMF reacted with 192 amines (200 mM, 3 μL) in DMF respectively in the presence of hydroxybenzotriazole (HOBt) (14 mM), O-benzotriazole-N,N,N',N'-tetramethyl-uronium-hexafluoro-phosphate (HBTU) (17 mM) and N,N-diisopropylethylamine (DIPEA) (28 mM) in 14 μL of dimethylformamide (DMF) overnight to assemble the combinatorial amide library 11a-d in 96 well plates. Ten of the reactions were picked up randomly and monitored by LC-MS, which showed an average of 70% yield desired products.

General method for the synthesis of (11a-1 to 11a-26 and 11c-1 to 11c-11). Compound 11a or 11c (0.02 mmol) dissolved in 0.5 mL of DMF was added to a solution of corresponding amines (0.04 mmol), HOBt (3.06 mg, 0.02 mmol), HBTU (7.58 mg, 0.02 mmol), and DIPEA (5.16 μL, 0.04 mmol) in 1 mL of DMF. The mixture was stirred under room temperature for 4 hours. This crude product was KJMM purified by Prep-HPLC to give titled compounds.

6-hydroxy-3-iodo-1-methyl-2-(3-(2-oxo-2-((4-(thiophen-3-yl)phenyl)amino)acetamido)phenyl)-1H-indole-5-carboxylic acid (11a-1, L97M74). Pale solid (3.8 mg, 29%); Decomposed at 185° C.; 1H NMR (500 MHz, DMSO): δ 11.08 (s, 1H), 10.95 (s, 1H), 8.06 (s, 1H), 8.01 (m, 1H), 7.92 (m, 2H), 7.85 (m, 2H), 7.75 (m, 2H), 7.63 (m, 1H), 7.57 (m, 2H), 7.33 (m, 1H), 7.06 (s, 1H), 3.63 (s, 3H); 13C NMR (125 MHz, DMSO): δ 173.0, 159.2, 158.8, 158.3, 142.6, 142.5, 141.4, 138.3, 137.1, 132.0, 131.5, 129.5, 127.5, 127.2, 126.8, 126.5, 124.1, 123.9, 122.8, 121.3, 120.9, 108.1, 97.1, 60.9, 32.6; HRMS (ESI): (M−H)− calcd for C28H19IN3O5S: 636.0096, found: 636.0098; LC-MS (ESI): 659.8 (M+Na)+, 635.8 (M−H)−; Purity: >95% (UV, λ=254 nm).

2-(3-(2-([1,1'-biphenyl]-4-ylamino)-2-oxoacetamido)phenyl)-6-hydroxy-3-iodo-1-methyl-1H-indole-5-carboxylic acid (11a-2, L97N08). Pale solid (3.5 mg, 27%); 1H NMR (500 MHz, DMSO): δ 11.11 (s, 1H), 11.02 (s, 1H), 8.08 (s, 1H), 8.03 (m, 1H), 7.99 (m, 2H), 7.87 (s, 1H), 7.70 (m, 4H), 7.59 (m, 1H), 7.37 (m, 2H), 7.33 (m, 2H), 7.06 (s, 1H), 3.64 (s, 3H); HRMS (ESI): (M−H)− calcd for C30H21IN3O5: 630.0531, found: 630.0546; LC-MS (ESI): 653.8 (M+Na)+, 629.8 (M−H)−; Purity: >95% (UV, λ=254 nm).

2-(3-(2-((4-(benzyloxy)-3-chlorophenyl)amino)-2-oxoacetamido)phenyl)-6-hydroxy-3-iodo-1-methyl-1H-indole-5-carboxylic acid (11a-3, L97M50). Pale solid (4.2 mg, 30%); 1H NMR (500 MHz, DMSO): δ 11.37 (s, 1H), 11.07 (s, 1H), 10.97 (s, 1H), 8.04 (m, 2H), 7.93 (m, 1H), 7.86 (s, 1H), 7.80 (m, 1H), 7.59-7.27 (m, 8H), 7.07 (s, 1H), 6.82 (m, 1H), 5.21 (s, 2H), 3.63 (s, 3H); HRMS (ESI): (M−H)− calcd for C31H22ClIN3O6: 694.0247, found: 694.0233; LC-MS (ESI): 718.0 (M+Na)+, 693.8 (M−H)−; Purity: >95% (UV, λ=254 nm).

2-(3-(2-((6-bromobenzo[d]thiazol-2-yl)amino)-2-oxoacetamido)phenyl)-6-hydroxy-3-iodo-1-methyl-1H-indole-5-carboxylic acid (11a-4, L97M61). Pale solid (3.4 mg, 24%); 1H NMR (500 MHz, DMSO): δ 13.16 (s, 1H), 11.37 (s, 1H), 11.27 (s, 1H), 8.37 (s, 1H), 8.02 (m, 2H), 7.87 (s, 1H), 7.78 (m, 1H), 7.63 (m, 2H), 7.34 (m, 1H), 7.07 (s, 1H), 3.63 (s, 3H); HRMS (ESI): (M−H)− calcd for C25H15BrIN4O5S: 688.8997, found: 688.9008; LC-MS (ESI): 690.6 (M−H)−; Purity: >95% (UV, λ=254 nm).

2-(3-(2-([1,1'-biphenyl]-3-ylamino)-2-oxoacetamido)phenyl)-6-hydroxy-3-iodo-1-methyl-1H-indole-5-carboxylic acid (11a-5, L97M48). Pale solid (4.5 mg, 35%); 1H NMR (500 MHz, DMSO): δ 11.37 (s, 1H), 11.12 (s, 1H), 10.99 (s, 1H), 8.23 (s, 1H), 8.05 (m, 2H), 7.90 (m, 1H), 7.87 (s, 1H), 7.80 (m, 1H), 7.65 (m, 3H), 7.52 (m, 6H), 7.08 (s, 1H), 3.63 (s, 3H); HRMS (ESI): (M−H)− calcd for C30H21IN3O5: 630.0531, found: 630.0533; LC-MS (ESI): 629.8 (M−H)−; Purity: >95% (UV, λ=254 nm).

2-(3-(2-((3-(benzyloxy)phenyl)amino)-2-oxoacetamido)phenyl)-6-hydroxy-3-iodo-1-methyl-1H-indole-5-carboxylic acid (11a-6, L97M52).Pale solid (3.6 mg, 27%); 1H NMR (500 MHz, DMSO): δ 11.38 (s, 1H), 11.09 (s, 1H), 10.86 (s, 1H), 8.06 (m, 1H), 8.00 (m, 1H), 7.86 (s, 1H), 7.64 (s, 1H), 7.58-7.27 (m, 9H), 7.07 (s, 1H), 6.82 (m, 1H), 5.10 (s, 2H), 3.63 (s, 3H); HRMS (ESI): (M−H)− calcd for C31H23IN3O6: 660.0637, found: 660.0627; LC-MS (ESI): 684.0 (M+Na)+, 659.8 (M−H)−; Purity: >95% (UV, λ=254 nm).

2-(3-(2-(5-bromoindolin-1-yl)-2-oxoacetamido)phenyl)-6-hydroxy-3-iodo-1-methyl-1H-indole-5-carboxylic acid (11a-7, L97M93). Pale solid (4.6 mg, 34%); 1H NMR (500 MHz, DMSO): δ 11.36 (s, 1H), 11.09 (s, 1H), 8.06 (m, 1H), 7.92 (m, 1H), 7.89 (s, 1H), 7.86 (s, 1H), 7.57 (m, 2H), 7.46 (m, 1H), 7.31 (m, 1H), 7.07 (s, 1H), 4.39 (m, 2H), 3.64 (s, 3H), 3.18 (m, 2H); HRMS (ESI): (M−H)− calcd for C26H18BrIN3O5: 657.9480, found: 657.9501; LC-MS (ESI): 661.8 (M+H)+, 659.8 (M−H)−; Purity: >95% (UV, λ=254 nm).

6-hydroxy-3-iodo-2-(3-(2-((4-iodophenyl)amino)-2-oxoacetamido)phenyl)-1-methyl-1H-indole-5-carboxylic acid (11a-8, L97M24). Pale solid (3.5 mg, 25%); 1H NMR (500 MHz, DMSO): δ 11.36 (s, 1H), 11.08 (s, 1H), 11.01 (s, 1H), 8.05 (s, 1H), 8.01 (m, 1H), 7.86 (s, 1H), 8.01 (m, 1H), 7.73 (m, 4H), 7.58 (m, 1H), 7.33 (m, 1H), 7.07 (s, 1H), 3.63 (s, 3H); HRMS (ESI): (M−H)− calcd for C24H16I2N3O5: 679.9185, found: 679.9183; LC-MS (ESI): 703.8 (M+Na)+, 679.8 (M−H)−; Purity: >95% (UV, λ=254 nm).

2-(3-(2-((2-(1H-benzo[d]imidazol-2-yl)phenyl)amino)-2-oxoacetamido)phenyl)-6-hydroxy-3-iodo-1-methyl-1H-indole-5-carboxylic acid (11a-9, L97M77). Pale solid (4.7 mg, 35%); 1H NMR (500 MHz, DMSO): δ 11.38 (s, 1H), 11.13 (s, 1H), 8.81 (m, 1H), 8.17 (m, 1H), 8.12 (s, 2H), 7.78 (s, 1H), 7.64 (m, 4H), 7.39 (m, 5H), 7.07 (s, 1H), 3.64 (s, 3H); HRMS (ESI): (M−H)− calcd for C31H21IN5O5: 670.0593, found: 670.0594; LC-MS (ESI): 672.0 (M+H)+, 669.8 (M−H)−; Purity: >95% (UV, λ=254 nm).

2-(3-(2-(benzo[d]thiazol-2-ylamino)-2-oxoacetamido)phenyl)-6-hydroxy-3-iodo-1-methyl-1H-indole-5-carboxylic acid (11a-10, L97N15). Pale solid (3.5 mg, 28%); 1H NMR (500 MHz, DMSO): δ 13.02 (s, 1H), 11.37 (s, 1H), 11.28 (s, 1H), 8.12 (m, 1H), 8.06 (s, 2H), 7.85 (m, 2H), 7.60 (m, 1H), 7.52 (m, 1H), 7.38 (m, 2H), 7.06 (s, 1H), 3.63 (s, 3H); HRMS (ESI): (M−H)− calcd for C25H16IN4O5S: 610.9892, found: 610.9884; LC-MS (ESI): 613.0 (M+H)+, 610.8 (M−H)−; Purity: >95% (UV, λ=254 nm).

2-(3-(2-((3-chlorophenyl)amino)-2-oxoacetamido)phenyl)-6-hydroxy-3-iodo-1-methyl-1H-indole-5-carboxylic acid (11a-11, L97M21).Pale solid (4.1 mg, 34%); 1H NMR (500 MHz, DMSO): δ 11.36 (s, 1H), 11.11 (s, 1H), 11.10 (s, 1H), 8.03 (m, 3H), 7.85 (m, 2H), 7.57 (m, 1H), 7.42 (m, 1H), 7.34 (m, 1H), 7.24 (m, 1H), 7.07 (s, 1H), 3.63 (s, 3H); HRMS (ESI): (M−H)− calcd for C24H16ClIN3O5: 587.9829, found: 587.9831; LC-MS (ESI): 587.8 (M−H)−; Purity: >95% (UV, λ=254 nm).

2-(3-(2-((4-(1H-imidazol-1-yl)phenyl)amino)-2-oxoacetamido)phenyl)-6-hydroxy-3-iodo-1-methyl-1H-indole-5-carboxylic acid (11a-12, L97M63). Pale solid (4.8 mg, 38%); 1H NMR (500 MHz, DMSO): δ 11.24 (s, 1H), 11.15 (s, 1H), 9.53 (s, 1H), 8.23 (s, 1H), 8.13 (m, 2H), 8.08 (s, 1H), 8.01 (m, 1H), 7.87 (s, 1H), 7.82 (m, 3H), 7.59 (m, 1H), 7.35 (m, 1H), 7.08 (s, 1H), 3.63 (s, 3H); HRMS (ESI): (M−H)− calcd for C27H19IN5O5: 620.0436, found: 620.0442; LC-MS (ESI): 622.0 (M+H)+, 619.8 (M−H)−; Purity: >95% (UV, λ=254 nm).

2-(3-(2-((4-chloro-3-(trifluoromethyl)phenyl)amino)-2-oxoacetamido)phenyl)-6-hydroxy-3-iodo-1-methyl-1H-indole-5-carboxylic acid (11a-13, L97M30). Pale solid (3.6 mg, 27%); 1H NMR (500 MHz, DMSO): δ 11.38 (s, 2H), 11.14 (s, 1H), 10.99 (s, 1H), 8.52 (s, 1H), 8.19 (m, 1H), 8.06 (s, 1H), 8.01 (m, 1H), 7.86 (s, 1H), 7.77 (m, 1H), 7.59 (m, 1H), 7.34 (m, 1H), 7.07 (s, 1H), 3.63 (s, 3H); HRMS (ESI): (M−H)− calcd for C25H15ClF3IN3O5: 655.9702, found:

655.9720; LC-MS (ESI): 679.8 (M+Na)+, 655.8 (M–H)–; Purity: >95% (UV, λ=254 nm).

6-hydroxy-3-iodo-1-methyl-2-(3-(2-oxo-2-((5-phenyl-1,3,4-thiadiazol-2-yl)amino)acetamido)phenyl)-1H-indole-5-carboxylic acid (11a-14, L97M73). Pale solid (4.5 mg, 35%); 1H NMR (500 MHz, DMSO): δ 13.61 (s, 1H), 11.38 (s, 1H), 11.29 (s, 1H), 8.01 (m, 4H), 7.86 (s, 1H), 7.58 (m, 4H), 7.34 (m, 4H), 7.07 (s, 1H), 3.62 (s, 3H); HRMS (ESI): (M–H)– calcd for C26H17ClIN5O5S: 638.0001, found: 638.0015; LC-MS (ESI): 637.8 (M–H)–; Purity: >95% (UV, λ=254 nm).

2-(3-(2-((4-fluorophenyl)amino)-2-oxoacetamido)phenyl)-6-hydroxy-3-iodo-1-methyl-1H-indole-5-carboxylic acid (11a-15, L97N95). Pale solid (4.7 mg, 41%); 1H NMR (500 MHz, DMSO): δ 11.39 (s, 1H), 11.11 (s, 1H), 11.02 (s, 1H), 8.06 (s, 1H), 8.01 (m, 1H), 7.92 (m, 2H), 7.88 (s, 1H), 7.58 (m, 1H), 7.34 (m, 1H), 7.23 (m, 2H), 7.06 (s, 1H), 3.63 (s, 3H); HRMS (ESI): (M–H)– calcd for C24H16FIN3O5: 572.0124, found: 572.0148; LC-MS (ESI): 571.8 (M–H)–; Purity: >95% (UV, λ=254 nm).

6-hydroxy-3-iodo-1-methyl-2-(3-(2-oxo-2-(thiazol-2-ylamino)acetamido)phenyl)-1H-indole-5-carboxylic acid (11a-16, L97N13). Pale solid (3.9 mg, 34%); 1H NMR (500 MHz, DMSO): δ 12.73 (s, 1H), 11.36 (s, 1H), 11.20 (s, 1H), 8.01 (s, 1H), 7.99 (s, 1H), 7.86 (s, 1H), 7.60 (m, 2H), 7.42 (m, 1H), 7.32 (m, 1H), 7.07 (s, 1H), 3.62 (s, 3H); HRMS (ESI): (M–H)– calcd for C21H14IN4O5S: 560.9735, found: 560.9744; LC-MS (ESI): 563.0 (M+H)+, 560.8 (M–H)–; Purity: >95% (UV, λ=254 nm).

6-hydroxy-3-iodo-1-methyl-2-(3-(2-oxo-2-((3-(trifluoromethoxy)phenyl)amino)acetamido)phenyl)-1H-indole-5-carboxylic acid (11a-17, L97M32). Pale solid (3.3 mg, 25%); 1H NMR (500 MHz, DMSO): δ 11.37 (s, 1H), 11.21 (s, 1H), 11.13 (s, 1H), 8.05 (m, 3H), 7.90 (m, 1H), 7.87 (s, 1H), 7.76-7.51 (m, 2H), 7.33 (m, 1H), 7.17 (m, 1H), 7.07 (s, 1H), 3.63 (s, 3H); HRMS (ESI): (M–H)– calcd for C25H16F3IN3O6: 638.0041, found: 638.0039; LC-MS (ESI): 661.8 (M+Na)+, 637.8 (M–H)–; Purity: >95% (UV, λ=254 nm).

2-(3-(2-((3-bromophenyl)amino)-2-oxoacetamido)phenyl)-6-hydroxy-3-iodo-1-methyl-1H-indole-5-carboxylic acid (11a-18, L97M18). Pale solid (3.8 mg, 30%); 1H NMR (500 MHz, DMSO): δ 11.38 (s, 1H), 11.10 (s, 1H), 11.08 (s, 1H), 8.17 (s, 1H), 8.06 (s, 1H), 8.01 (m, 1H), 7.89 (m, 1H), 7.86 (s, 1H), 7.58 (m, 1H), 7.36 (m, 3H), 7.07 (s, 1H), 3.63 (s, 3H); HRMS (ESI): (M–H)– calcd for C24H16BrIN3O5: 631.9323, found: 631.9326; LC-MS (ESI): 655.8 (M+Na)+, 631.8 (M–H)–; Purity: >95% (UV, λ=254 nm).

2-(3-(2-((3-fluorophenyl)amino)-2-oxoacetamido)phenyl)-6-hydroxy-3-iodo-1-methyl-1H-indole-5-carboxylic acid (11a-19, L97N07). Pale solid (4.7 mg, 41%); 1H NMR (500 MHz, DMSO): δ 11.37 (s, 1H), 11.13 (s, 2H), 8.08 (s, 1H), 8.03 (m, 1H), 7.99 (m, 2H), 7.87 (s, 1H), 7.82 (m, 1H), 7.76 (m, 1H), 7.58 (m, 1H), 7.43 (m, 1H), 7.32 (m, 1H), 7.06 (s, 1H), 7.01 (m, 1H), 3.64 (s, 3H); HRMS (ESI): (M–H)– calcd for C24H16FIN3O5: 572.0124, found: 572.0136; LC-MS (ESI): 573.8 (M+H)+, 571.8 (M–H)–; Purity: >95% (UV, λ=254 nm).

6-hydroxy-3-iodo-2-(3-(2-((3-iodophenyl)amino)-2-oxoacetamido)phenyl)-1-methyl-1H-indole-5-carboxylic acid (11a-20, L97M23). Pale solid (4.5 mg, 33%); 1H NMR (500 MHz, DMSO): δ 11.36 (s, 1H), 11.08 (s, 1H), 11.01 (s, 1H), 8.34 (s, 1H), 8.05 (s, 1H), 8.01 (m, 1H), 8.01 (m, 1H), 7.90 (m, 1H), 7.87 (s, 1H), 7.57 (m, 2H), 7.33 (m, 1H), 7.19 (m, 1H), 7.07 (s, 1H), 3.63 (s, 3H); HRMS (ESI): (M–H)– calcd for C24H16I2N3O5: 679.9185, found: 679.9184; LC-MS (ESI): 679.8 (M–H)–; Purity: >95% (UV, λ=254 nm).

2-(3-(2-((4'-cyano-[1,1'-biphenyl]-4-yl)amino)-2-oxoacetamido)phenyl)-6-hydroxy-3-iodo-1-methyl-1H-indole-5-carboxylic acid (11a-21, L97L08). Pale solid (2.3 mg, 17%); 1H NMR (500 MHz, DMSO): δ 11.37 (s, 1H), 11.12 (s, 1H), 11.10 (s, 1H), 8.14-8.04 (m, 4H), 7.93 (m, 4H), 7.87-7.81 (m, 3H), 7.59 (m, 1H), 7.35 (m, 1H), 7.07 (s, 1H), 3.64 (s, 3H); HRMS (ESI): (M–H)– calcd for C31H20IN4O5: 655.0484, found: 655.0509; LC-MS (ESI): 654.8 (M–H)–; Purity: >95% (UV, λ=254 nm).

2-(3-(2-((3'-cyano-[1,1'-biphenyl]-4-yl)amino)-2-oxoacetamido)phenyl)-6-hydroxy-3-iodo-1-methyl-1H-indole-5-carboxylic acid (11a-22, L97L07). Pale solid (2.9 mg, 21%); 1H NMR (500 MHz, DMSO): δ 11.37 (s, 1H), 11.11 (s, 1H), 11.07 (s, 1H), 8.18 (s, 1H), 8.03 (m, 5H), 7.87 (s, 1H), 7.82 (m, 3H), 7.67 (m, 1H), 7.59 (m, 1H), 7.34 (m, 1H), 7.08 (s, 1H), 3.64 (s, 3H); HRMS (ESI): (M–H)– calcd for C31H20IN4O5: 655.0484, found: 655.0499; LC-MS (ESI): 654.8 (M–H)–; Purity: >95% (UV, λ=254 nm).

6-hydroxy-2-(3-(2-((2-(5-(hydroxymethyl)furan-2-yl)phenyl)amino)-2-oxoacetamido)phenyl)-3-iodo-1-methyl-1H-indole-5-carboxylic acid (11a-23, L97L03). Pale solid (2.4 mg, 18%); 1H NMR (500 MHz, DMSO): δ 11.15 (s, 1H), 10.76 (s, 1H), 8.05 (m, 3H), 7.87 (s, 1H), 7.82 (s, 1H), 7.76 (m, 1H), 7.58 (m, 2H), 7.41 (m, 3H), 7.08 (s, 1H), 4.51 (s, 2H), 3.65 (s, 1H), 3.64 (s, 3H); HRMS (ESI): (M–H)– calcd for C29H21IN3O7: 650.0430, found: 650.0422; LC-MS (ESI): 649.8 (M–H)–; Purity: >95% (UV, λ=254 nm).

2-(3-(2-((3-(furan-2-yl)phenyl)amino)-2-oxoacetamido)phenyl)-6-hydroxy-3-iodo-1-methyl-1H-indole-5-carboxylic acid (11a-24, L97L05). Pale solid (4.6 mg, 37%); 1H NMR (500 MHz, DMSO): δ 11.36 (s, 1H), 11.10 (s, 1H), 10.98 (s, 1H), 8.29 (s, 1H), 8.07 (s, 1H), 8.03 (m, 1H), 7.94 (m, 1H), 7.87 (s, 1H), 7.77 (m, 2H), 7.50 (m, 4H), 7.34 (m, 1H), 7.07 (s, 1H), 6.90 (m, 1H), 3.64 (s, 3H); HRMS (ESI): (M–H)– calcd for C28H19IN3O6: 620.0324, found: 620.0327; LC-MS (ESI): 619.8 (M–H)–; Purity: >95% (UV, λ=254 nm).

2-(3-(2-((4'-cyano-[1,1'-biphenyl]-3-yl)amino)-2-oxoacetamido)phenyl)-6-hydroxy-3-iodo-1-methyl-1H-indole-5-carboxylic acid (11a-25, L97L06). Pale solid (3.4 mg, 26%); 1H NMR (500 MHz, DMSO): δ 11.12 (s, 1H), 11.05 (s, 1H), 8.29 (s, 1H), 8.08 (s, 1H), 8.03 (m, 4H), 7.87 (s, 1H), 7.86 (s, 1H), 7.56 (m, 3H), 7.33 (m, 1H), 7.09 (s, 1H), 3.64 (s, 3H); HRMS (ESI): (M–H)– calcd for C31H20IN4O5: 655.0484, found: 655.0485; LC-MS (ESI): 654.8 (M–H)–; Purity: >95% (UV, λ=254 nm).

6-hydroxy-3-iodo-1-methyl-2-(3-(2-oxo-2-((3-(thiophen-3-yl)phenyl)amino)acetamido)phenyl)-1H-indole-5-carboxylic acid (11a-26, L97L02). Pale solid (3.1 mg, 24%); 1H NMR (500 MHz, DMSO): δ 11.12 (s, 1H), 10.92 (s, 1H), 8.22 (s, 1H), 8.08 (s, 1H), 8.02 (m, 4H), 7.87 (s, 1H), 7.84 (m, 2H), 7.68 (m, 1H), 7.59 (m, 1H), 7.52 (m, 2H), 7.43 (m, 1H), 7.34 (m, 1H), 7.08 (s, 1H), 3.64 (s, 3H); HRMS (ESI): (M–H)– calcd for C28H19IN3O5S: 636.0096, found: 636.0102; LC-MS (ESI): 635.8 (M–H)–; Purity: >95% (UV, λ=254 nm).

6-hydroxy-3-iodo-1-methyl-2-(3-(4-oxo-4-((4-(thiophen-3-yl)phenyl)amino)butanamido)phenyl)-1H-indole-5-carboxylic acid (11c-1, L88M74). Pale solid (3.8 mg, 28%); 1H NMR (500 MHz, DMSO): δ 11.35 (brs, 1H), 10.24 (s, 1H), 10.08 (s, 1H), 7.86 (s, 1H), 7.73 (m, 4H), 7.62 (m, 4H), 7.52 (m, 3H), 7.17 (m, 1H), 7.04 (s, 1H), 3.56 (s, 3H), 2.69 (m, 4H); HRMS (ESI): (M–H)– calcd for C30H23IN3O5S: 664.0409, found: 664.0414; LC-MS (ESI): 663.8 (M–H)–; Purity: >95% (UV, λ=254 nm).

6-hydroxy-3-iodo-1-methyl-2-(3-(4-oxo-4-((4-phenoxyphenyl)amino)butanamido)phenyl)-1H-indole-5-carboxylic acid (11c-2, L88M49). Pale solid (1.6 mg, 11%); 1H NMR (500 MHz, DMSO): δ 10.22 (s, 1H), 10.04 (s, 1H), 7.83 (s, 1H), 7.76 (m, 2H), 7.60 (m, 2H), 7.47 (m, 1H), 7.35 (m, 2H), 7.09 (m, 3H), 6.96 (m, 4H), 3.58 (s, 3H), 2.67 (m, 4H); HRMS (ESI): (M−H)− calcd for C32H25IN3O6: 674.0794, found: 664.0796; LC-MS (ESI): 673.8 (M−H)−; Purity: >95% (UV, λ=254 nm).

2-(3-(4-((4-(benzyloxy)-3-chlorophenyl)amino)-4-oxobutanamido)phenyl)-6-hydroxy-3-iodo-1-methyl-1H-indole-5-carboxylic acid (11c-3, L88M50). Pale solid (5.7 mg, 39%); 1H NMR (500 MHz, DMSO): δ 10.23 (s, 1H), 10.03 (s, 1H), 7.84 (s, 1H), 7.80 (m, 2H), 7.49-7.33 (m, 8H), 7.17 (m, 2H), 7.03 (s, 1H), 5.15 (s, 2H), 3.58 (s, 3H), 2.67 (m, 4H); HRMS (ESI): (M−H)− calcd for C33H26ClIN3O6: 722.0560, found: 722.0563; LC-MS (ESI): 746.0 (M+Na)+, 721.8 (M−H)−; Purity: >95% (UV, λ=254 nm).

2-(3-(4-((3-(benzyloxy)phenyl)amino)-4-oxobutanamido)phenyl)-6-hydroxy-3-iodo-1-methyl-1H-indole-5-carboxylic acid (11c-4, L88M52). Pale solid (2.2 mg, 15%); 1H NMR (500 MHz, DMSO): δ 11.35 (brs, 1H), 10.22 (s, 1H), 9.99 (s, 1H), 7.84 (s, 1H), 7.73 (m, 2H), 7.50-7.32 (m, 7H), 7.15 (m, 3H), 7.04 (s, 1H), 6.68 (m, 1H), 5.05 (s, 2H), 3.58 (s, 3H), 2.67 (m, 4H); HRMS (ESI): (M−H)− calcd for C33H27IN3O6: 688.0950, found: 688.0950; LC-MS (ESI): 687.8 (M−H)−; Purity: >95% (UV, λ=254 nm).

2-(3-(4-([1,1'-biphenyl]-3-ylamino)-4-oxobutanamido)phenyl)-6-hydroxy-3-iodo-1-methyl-1H-indole-5-carboxylic acid (11c-5, L88M48). Pale solid (4.8 mg, 36%); 1H NMR (500 MHz, DMSO): δ 11.35 (brs, 1H), 10.24 (s, 1H), 10.12 (s, 1H), 7.93 (m, 2H), 7.84 (s, 1H), 7.76 (m, 2H), 7.60-7.40 (m, 8H), 7.16 (m, 1H), 7.03 (s, 1H), 3.58 (s, 3H), 2.64 (m, 4H); HRMS (ESI): (M−H)− calcd for C32H25IN3O5: 658.0844, found: 658.0861; LC-MS (ESI): 683.4 (M+H)+, 657.8 (M−H)−; Purity: >95% (UV, λ=254 nm).

2-(3-(4-(5-bromoindolin-1-yl)-4-oxobutanamido)phenyl)-6-hydroxy-3-iodo-1-methyl-1H-indole-5-carboxylic acid (11c-6, L88M93). Pale solid (3.2 mg, 23%); 1H NMR (500 MHz, DMSO): δ 11.35 (brs, 1H), 10.25 (s, 1H), 7.97 (m, 1H), 7.84 (s, 1H), 7.76 (m, 2H), 7.47 (m, 1H), 7.42 (s, 1H), 7.29 (m, 1H), 7.17 (m, 1H), 7.04 (m, 1H), 4.16 (m, 2H), 3.56 (s, 3H), 3.17 (m, 2H), 2.77 (m, 2H), 2.71 (m, 2H); HRMS (ESI): (M−H)− calcd for C28H22BrIN3O5: 685.9793, found: 685.9798; LC-MS (ESI): 687.8 (M−H)−; Purity: >95% (UV, λ=254 nm).

6-hydroxy-3-iodo-1-methyl-2-(3-(4-oxo-4-((4-(trifluoromethoxy)phenyl)amino)butanamido)phenyl)-1H-indole-5-carboxylic acid (11c-7, L88M33). Pale solid (6.1 mg, 45%); 1H NMR (500 MHz, DMSO): δ 11.35 (brs, 1H), 10.23 (s, 1H), 10.22 (s, 1H), 7.84 (s, 1H), 7.71 (m, 5H), 7.48 (m, 1H), 7.30 (m, 2H), 7.16 (m, 1H), 7.03 (s, 1H), 3.58 (s, 3H), 2.70 (m, 4H); HRMS (ESI): (M−H)− calcd for C27H20F3IN3O6: 666.0354, found: 666.0329. LC-MS (ESI): 665.8 (M−H)−; Purity: >95% (UV, λ=254 nm).

6-hydroxy-3-iodo-2-(3-(4-((4-(isopropylphenyl)amino)-4-oxobutanamido)phenyl)-1-methyl-1H-indole-5-carboxylic acid (11c-8, L88N25). Pale solid (2.1 mg, 16%); 1H NMR (500 MHz, DMSO): δ 9.91 (s, 1H), 7.70 (s, 1H), 7.50-7.45 (m, 5H), 7.15 (m, 5H), 6.66 (s, 1H), 3.58 (s, 3H), 2.82 (m, 1H), 2.64 (m, 4H), 1.17 (d, J=6.9 Hz, 1H); HRMS (ESI): (M−H)− calcd for C29H27IN3O5: 624.1001, found: 624.1037; LC-MS (ESI): 648.0 (M+Na)+, 624.0 (M−H)−; Purity: >95% (UV, λ=254 nm).

2-(3-(4-((benzo[d][1,3]dioxol-5-ylmethyl)amino)-4-oxobutanamido)phenyl)-6-hydroxy-3-iodo-1-methyl-1H-indole-5-carboxylic acid (11c-9, L88N79). Pale solid (8.1 mg, 63%); 1H NMR (500 MHz, DMSO): δ 11.35 (brs, 1H), 10.19 (s, 1H), 8.37 (m, 1H), 7.85 (s, 1H), 7.61 (s, 1H), 7.72 (m, 1H), 7.47 (m, 1H), 7.16 (m, 1H), 7.03 (s, 1H), 6.80 (m, 2H), 6.70 (m, 1H), 5.93 (s, 2H), 4.17 (m, 2H), 3.58 (s, 3H), 2.64 (m, 4H); 13C NMR (125 MHz, DMSO): δ 172.8, 171.8, 171.3, 158.2, 147.6, 146.3, 142.9, 142.5, 139.8, 133.9, 131.5, 129.4, 125.5, 123.9, 123.8, 121.2, 120.7, 119.8, 108.3, 108.2, 108.0, 101.1, 97.0, 60.5, 42.2, 32.5, 32.0, 30.6; HRMS (ESI): (M−H)− calcd for C28H23IN3O7: 640.0586, found: 640.0569; LC-MS (ESI): 642.0 (M+H)+, 639.6 (M−H)−; Purity: >95% (UV, λ=254 nm).

2-(3-(4-((cyclopropylmethyl)(propyl)amino)-4-oxobutanamido)phenyl)-6-hydroxy-3-iodo-1-methyl-1H-indole-5-carboxylic acid (11c-10, L88N40). Pale solid (10.6 mg, 87%); 1H NMR (500 MHz, DMSO): δ 11.35 (brs, 1H), 10.16 (s, 1H), 7.85 (s, 1H), 7.73 (m, 2H), 7.48 (m, 1H), 7.16 (m, 1H), 7.04 (s, 1H), 3.58 (s, 3H), 3.33-3.14 (m, 4H), 2.64 (m, 2H), 1.59-1.46 (m, 2H), 0.88 (m, 4H), 0.50-0.10 (m, 4H); HRMS (ESI): (M−H)− calcd for C27H29IN3O5: 602.1157, found: 602.1171; LC-MS (ESI): 604.0 (M+H)+, 602.0 (M−H)−; Purity: >95% (UV, λ=254 nm).

6-hydroxy-3-iodo-1-methyl-2-(3-(4-oxo-4-(thiazol-2-ylamino)butanamido)phenyl)-1H-indole-5-carboxylic acid (11c-11, L88N13). Pale solid (0.9 mg, 7%); 1H NMR (500 MHz, DMSO): δ 12.15 (s, 1H), 10.25 (s, 1H), 7.84 (s, 1H), 7.74 (m, 2H), 7.46 (m, 3H), 7.17 (m, 3H), 6.88 (s, 1H), 3.58 (s, 3H), 2.64 (m, 4H); HRMS (ESI): (M−H)− calcd for C23H18IN4O5S: 589.0048, found: 589.0056; LC-MS (ESI): 591.0 (M+H)+; Purity: >95% (UV, λ=254 nm).

Example 1

In this Example, the co-crystal structure of SHP2 catalytic domain with IIB08 was analyzed.

SHP2 crystallization and X-ray data collection. Recombinant SHP2 expression and purification were previously described in Zhang et al., 2010, Salicylic acid-based small molecule inhibitor for the oncogenic Src homology-2 domain containing protein tyrosine phosphatase-2 (SHP2), J. Med. Chem. 53, pp. 2482-2493. The crystallization experiments were performed at room temperature using the sitting drop vapor diffusion method.

In the crystal structure, the hydroxyindole carboxylic acid core binds to the active site of SHP2 and the distal phenyl ring in the biphenyl moiety is sandwiched between the side chains of R362 and K364 in the $\beta_5$-$\beta_6$ loop (residues 362-365), which is highly divergent among the PTPs, and interactions between the terminal biphenyl group and residues R362 and K364 likely contribute to the observed potency and selectivity of IIB08; however, the 2-phenyl had almost no interaction with the enzyme, which was mostly due to the rigidity of the triazolidine linker formed as a result of the Click reaction. No significant contact was observed between the triazolidine linker and SHP2. Based on this information, diversified commercially available amines were added to position 2 of the hydroxyindole carboxylic acid through proper linkers to increase both potency and specificity of the hydroxyindole carboxylic acid (FIG. 1). Particularly, 192 commercially available amines (FIGS. 3A and 3B) were selected that vary by charge, polarity, hydrophobicity, solubility, and drug-like activity and therefore provide a structural diversity to increase the number and strength of non-covalent interactions between SHP2 and the inhibitor. Further, to ensure that library components could optimally bridge both the active site cavity and the adjacent peripheral site in SHP2, a spacer of 0 to 3 methylene units was introduced between the two carbonyls in the amino-oxo acylamido phenyl linker (FIG. 1).

Figure 2:
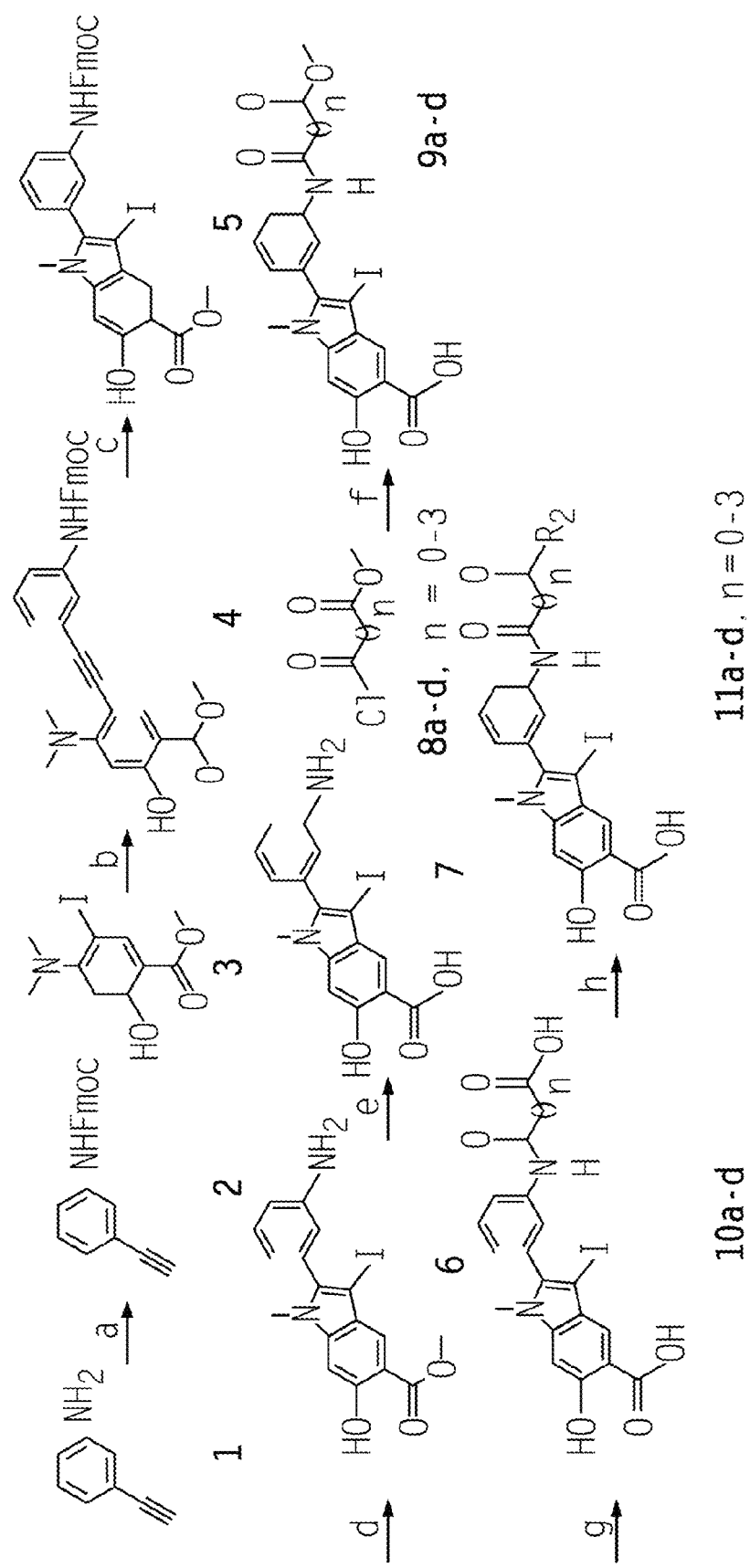
FIG. 2 is a schematic illustrating the strategy and design of the hydroxyindole carboxylic acid based SHP2 inhibitor libraries 11a-d used in the present disclosure and described in Example 1. Conditions: (a) FmocOSu, THF, Reflux, 20 h, 81.4%; (b) Pd(PPh$_3$)$_2$Cl$_2$, CuI, Na$_2$CO$_3$, DMF, 44%; (c) I$_2$, NaHCO$_3$, CH$_2$Cl$_2$ or AcCN, rt, 86%; (d) 50% diethylamine in DCM, 3 h, 85%; (e) 5% LiOH/THF=1:2, 80 deg., 2 h, 97.2%; (f) corresponding acyl chloride, Et$_3$N, DMF, 0° C., 80-90%; (g) 5% LiOH/THF=1:2, rt, 2 h, 80-90%; (h) 192 amines, HOBT, HBTU, DIPEA, DMF, rt, overnight. 60-80%.

To construct the bidentate libraries 11a-d (FIG. 2), amine 1 was protected with FmocOSu to produce alkyne 2. Alkyne 2 was coupled with iodide 3 by Sonogashira reaction to afford compound 4 with 44% yield. Electrophilic cyclization of 4 by $I_2$ furnished compound 5 in 86% yields. Deprotection of 5 under 50% diethylamine in DCM afforded amine 6. Compound 7 was obtained by hydrolysis of 6 in 5% LiOH under 80° C. for 2 hours. Compound 7, upon treatment with acetyl chlorides 8a-d, yielded compounds 9a-d, which were hydrolyzed in 5% LiOH at room temperature for 2 hours to produce compounds 10a-d. To assemble libraries 11a-d, 192 structurally diverse amines (FIGS. 3A and 3B) were introduced, in equal quantities, into individual wells of two 96-well plates, in the presence of hydroxybenzotriazole (HOBt), O-benzotriazole-N,N,N',N'-tetramethyl-uronium-hexafluoro-phosphate (HBTU) and diisopropylethylamine (DIPEA) in dimethylformamide (DMF) to condense with the carboxylic acid in compounds 10a-d overnight. The quality of the reactions in the wells was randomly monitored by LC-MS, indicating that 60-80% of compounds 10a-d was converted to the desired products (compounds 11a-d).

Libraries 11a-d were screened at ~5 μM for SHP2 inhibitors without further purification. The ability of the library components to inhibit the SHP2-catalyzed hydrolysis of p-nitrophenyl phosphate (pNPP) was evaluated at pH 7.0 and 25° C. More particularly, the phosphatase activity of SHP2 was assayed using p-nitrophenyl phosphate (pNPP) as a substrate at 25° C. in 50 mM 3,3-dimethylglutarate buffer, pH 7.0, containing 1 mM EDTA with an ionic strength of 0.15 μM adjusted by NaCl. The libraries were screened in a 96-well format at 5 μM compound concentration. The reaction was initiated by the addition of 5 μl of the enzyme to 195 μl of the reaction mixture containing 5 μM library compound and 2.9 mM (the $K_m$ value) pNPP, and quenched after 5 minutes by the addition of 50 μl of 5 N NaOH. The nonenzymatic hydrolysis of pNPP was corrected by measuring the control without the addition of enzyme. The amount of product p-nitrophenol was determined from the absorbance at 405 nm detected by a Spectra MAX340 microplate spectrophotometer (Molecular Devices, Sunnyvale, Calif.) using a molar extinction coefficient of 18,000 $M^{-1} cm^{-1}$. Inhibitor concentrations used for $IC_{50}$ measurements cover the range of from 0.2 to 5× of the $IC_{50}$ value. $IC_{50}$ values for selected resynthesized and purified hits were calculated by fitting the absorbance at 405 nm versus inhibitor concentration to the following equation:

$$A_I/A_0 = IC_{50}/(IC_{50}+[I])$$

where $A_I$ is the absorbance at 405 nm of the sample in the presence of the inhibitor; $A_0$ is the absorbance at 405 nm in the absence of inhibitor; and [I] is the concentration of the inhibitor.

It became immediately evident from the initial screening results that the linker length is of critical importance. In fact, all of the top hits were from library 11a, which has the shortest oxalic linker.

The top 22 hits from library 11a were resynthesized, purified by high performance liquid chromatography (HPLC), and their $IC_{50}$ values determined. As can be seen from Table 2, the $IC_{50}$ values matched well with the percent inhibition data measured at ~5 μM compound concentration. The best hit compound, 11a-1, identified from the screen also exhibited the lowest $IC_{50}$ value of 0.20±0.02 μM against SHP2. Similar to 11a-1, other compounds bearing a biaryl substituent (e.g., 11a-2 and 11a-5) also strongly inhibited SHP2. Interestingly, compounds with the benzyloxyphenyl amino scaffold (e.g., 11a-3 and 11a-6) also inhibited SHP2 at submicromolar concentration.

To further establish biaryl substituents as privileged structures for SHP2 binding, six additional biaryl substituted derivatives of 11a-1 (Table 3) were synthesized. The $IC_{50}$ values of compounds 11a-21 to 11a-26 were comparable to that of 11a-1. To confirm the effectiveness of oxalic linker, 11 top hits from library 11c (with a succinic linker) were resynthesized and characterized. In agreement with the results from screening, the hits selected from library 11c were less potent than their library 11a counterparts (Table 2 and Table 4). For example, 11c-1, the top hit from library 11c, had an $IC_{50}$ of 2.3 μM, which is more than 10 times higher than that of 11a-1 ($IC_{50}$=0.20 μM).

Collectively, the structure and activity data indicated that the aromatic oxalic linker and biaryl substituents are preferred for enhanced inhibitor binding toward SHP2.

Selectivity profiling revealed that 11a-1 exhibited over 5-fold selectivity for SHP2 over a panel of 20 mammalian PTPs, including receptor-like PTPs, PTPμ, PTPε, PTPα, PTPσ and PTPγ, cytosolic PTPs, protein tyrosine phosphatase 1B (PTP1B), lymphoid protein tyrosine phosphatase (Lyp), SHP1, protein tyrosine phosphatase H1 (PTPH1), hematopoietic tyrosine phosphatase (HePTP), Striatal-enriched protein tyrosine phosphatase (STEP), and protein tyrosine phosphatase PEZ, the dual specificity phosphatase, vaccinia H1-related phosphatase (VHR), VH1-like phosphatase Z (VHZ), MAP kinase phosphatase 5 (MKP5), protein phosphatase CDC14A, ubiquitin-like domain-containing CTD phosphatase 1 (UBLCP1) and laforin, low molecular weight PTP (LMWPTP) and protein phosphatase SSu72 (Table 5). The PTPs were expressed and purified from E. coli. The $IC_{50}$ determination for these PTPs was performed under the same conditions as for SHP2 except the pNPP concentrations used corresponded to the $K_m$ values of the PTPs studied.

Of particular note, compound 11a-1 displayed a 7- and 11-fold preference for SHP2 over its most related relatives SHP1 and PTP1B.

Example 2

In this Example, the structural basis of SHP2 inhibition by compound 11a-1 and 11c-9 was analyzed.

Particularly, to elucidate the structural basis of SHP2 inhibition by 11a-1 or 11c-9, the crystal structure of the SHP2 PTP domain (residues 240-528) in complex with 11a-1 or 11c-9 was determined.

For co-crystallization, 100 μl of SHP2 stock (7.0 mg/ml) in 20 mM MES (pH 6.0), 50 mM NaCl, 0.1 mM EDTA, and 4 mM DTT was mixed with 1 μl of compound 11a-1 or 11c-9 stock solution (50 mM in DMSO). No diffraction crystals, however, were obtained for the SHP2•11a-1 complex.

Crystals of the SHP2•11c-9 complex were obtained at room temperature by vapor diffusion in sitting drops. Protein drops were equilibrated against a reservoir solution containing 20% w/v polyethylene glycol 3350, 200 mM magnesium acetate tetrahydrate, and 100 mM HEPES buffer (pH 7.7) and were allowed to soak for 30 minutes. The crystals were then flash-cooled by liquid nitrogen. X-ray data were collected at 19 BM beamline at APS (Argonne, Ill.). Data were processed using the program HKL3000 (Minor et al., 2006, HKL-3000: the integration of data reduction and structure solution—from diffraction images to an initial model in minutes. Acta. Crystallogr. Sect. D. 62, pp. 859-866). The space group of the crystallized in space group P1 with one molecule in the asymmetric unit.

Figure 4A:
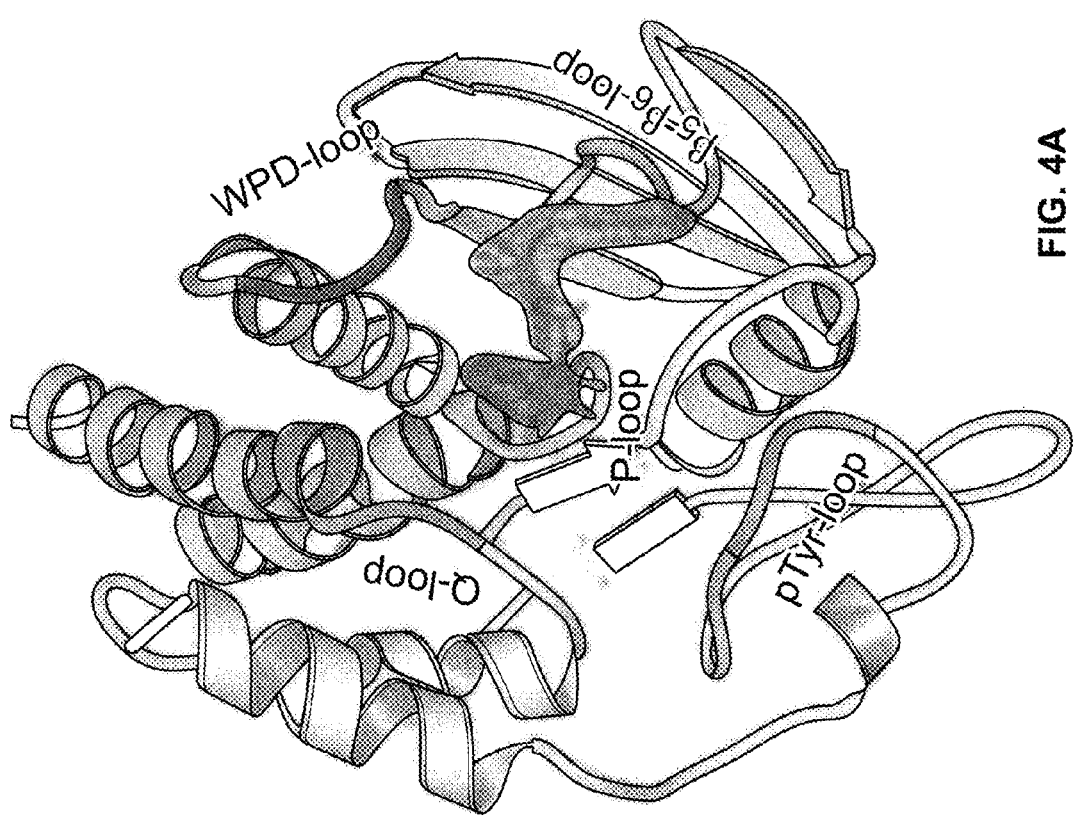
FIGS. 4A & 4B depict the crystal structure of SHP2 in complex with compound 11c-9 as analyzed in Example 2.
Figure 4B:
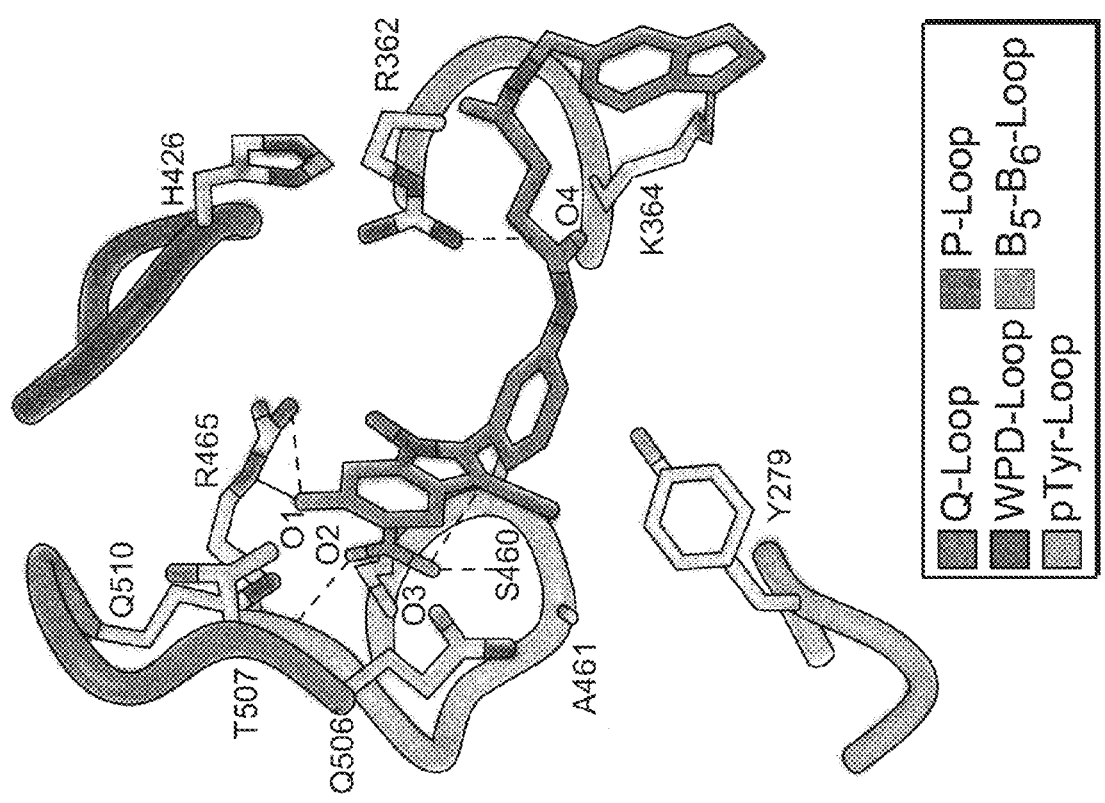
Figure 4B:
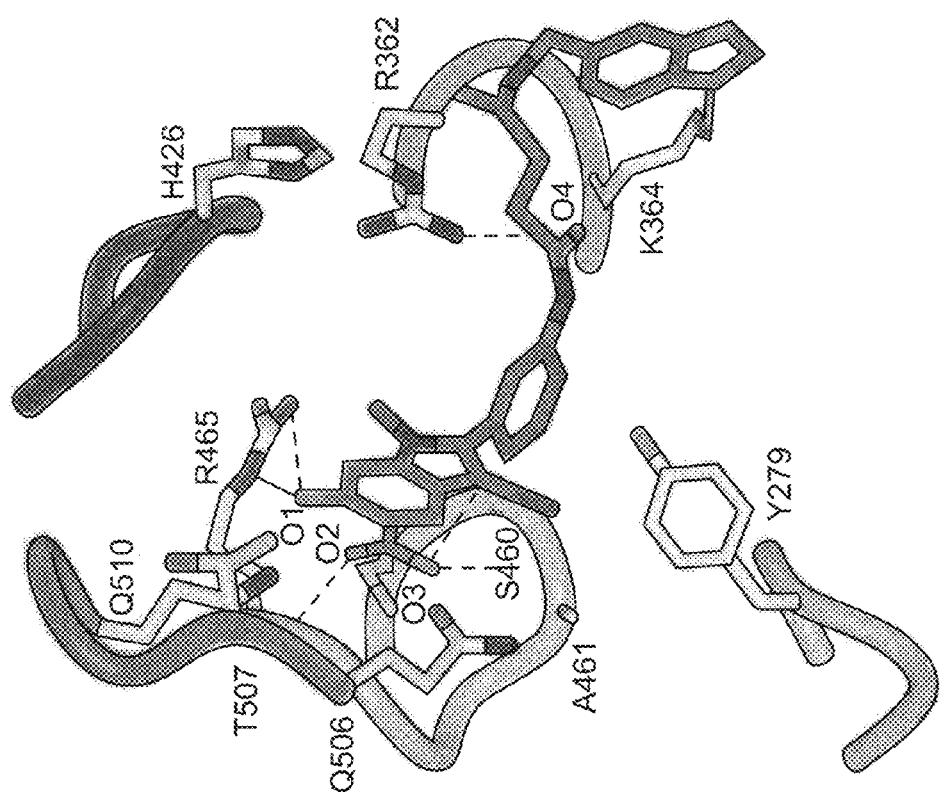

The crystals of the SHP2•11c-9 complex diffracted to 2.1 Å resolution, and the structure was solved by molecular replacement using the program MolRep (Vagin & Teplyakov, 1997, MOLREP: an automated program for molecular replacement, J. Appl. Cryst. 30, pp. 1022-1025). The apo-form of SHP2 catalytic domain (PDB accession 3B70) (Barr et al., 2009, Large-scale structural analysis of the classical human protein tyrosine phosphatome, Cell 136, pp. 352-363) was used as the search model. The resulting difference Fourier map indicated that the first 16 N-terminal residues have different conformation. The map also revealed the density for the compound 11c-9 in the active site of SHP2. The N-terminal peptide 246-261 was firstly rebuilt according to the Fo-Fc density map. The three-dimensional structure of SHP2•11c-9 was refined to a crystallographic R-factor of 20.3% ($R_{free}$=26.4%) (2.4 resolution) with the program CNS1.1 (Brunger et al., 1998, Crystallography & NMR system: a new software suite for macro-molecular structure determination, Acta Crystallogr. Sect. D. 54, pp. 905-921) using simulated annealing at 2,500 K and then alternating positional and individual temperature factor refinement cycles. The statistics for data collection and refinement are shown in Table 6. The atomic model includes SHP2 residues 246-314 and 323-526, and all atoms of the compound 11c-9 (FIGS. 4A & 4B).

TABLE 6

Data collection and refinement statistics

| | SHP2•11c-9 |
|---|---|
| Crystal parameters | |
| Space group | P1 |
| Cell Dimensions | |
| a (Å) | 40.0 |
| b (Å) | 40.9 |
| c (Å) | 48.9 |
| α (°) | 94.6 |
| β (°) | 109.2 |
| γ (°) | 110.0 |
| Data Collection | |
| resolution range (Å) | 50.0-2.1 |
| no. of unique reflections | 12808 |
| completeness (%) | 82.3 |
| redundancy | 2.5 |
| $R_{merge}^{a}$ | 0.071 |
| Refinement | |
| resolution range (Å) | 50.0-2.4 |
| no. of reflections used (F ≥ 1.58 (F)) | 9357 |
| completeness (%) | 88.9 |
| no. of protein atoms | 2219 |
| no. of inhibitors | 1 |
| $R_{work}^{b}/R_{free}^{c}$ | 23.6/28.6 |
| rms Deviations from Ideal Geometry | |
| bond length (Å) | 0.0106 |
| bond angle (°) | 1.52 |

$^{a}R_{merge} = \Sigma_{h}\Sigma_{i}|I(h)_{i} - \langle I(h) \rangle|/\Sigma_{h}\Sigma_{i}I(h)_{i}$.
$^{b}R_{work} = \Sigma_{h}|F(h)_{calcd} - F(h)_{obsd}|/\Sigma_{h}F(h)_{obsd}$ where $F(h)_{calcd}$ and $F(h)_{obsd}$ were the refined calculated and observed structure factors, respectively.
$^{c}R_{free}$ was calculated for a randomly selected 3.7% of the reflections that were omitted from refinement.

The overall structure of SHP2•11c-9 is similar to the ligand free SHP2 structure used for molecular replacement, with the root-mean-square-derivation (rmsd) for all α-carbon positions between the two being 0.53 Å. The major differences between the two structures are electron density in the SHP2 active site corresponding to 11c-9, which was confirmed by the $|F_{o}|-|F_{c}|$ difference map contoured at 2.5σ (FIG. 4A), and the N-terminal peptide 246-261, which was rebuilt according to the $|F_{o}|-|F_{c}|$ density map. The hydroxyindole carboxylic acid moiety in 11c-9 occupies the SHP2 active-site pocket and forms extensive interactions with residues in the P-loop (residues 458-465), the pTyr recognition loop (residues 277-284), and the Q loop (residues 501-507) (FIG. 4B). Specifically, the phenolic oxygen $O_1$ within the hydroxyindole carboxylic acid core makes two hydrogen bonds with the side chain of R465 in the P-loop; the carboxylate $O_2$ is hydrogen bonded to the main chain amide of R465, and $O_3$ contributes one H-bond with the main chain amide of A461 and one polar interaction with the side chain of S460. The indole ring interacts favorably with the side chains of S460, A461, and R465 in the P-loop as well as the side chains of Q506, T507, and Q510 in the Q-loop, and the iodine atom at the 3-position of the indole ring has van der Waals contacts with the side chain of Y279. Interestingly, the distal benzodioxol ring in 11c-9 is also involved in polar and non-polar interactions with the side chain of K364 in the $\beta_5$-$\beta_6$ loop (residues 362-365). Finally, the succinic linker makes van der Waals contacts with both the side chain of R362 in the $\beta_5$-$\beta_6$ loop and the side chain of H426 in the WPD loop (residues 421-431), whereas the carbonyl oxygen $O_4$ in the linker forms a polar interaction with the side chain of R362.

Example 3

In this Example, the molecular basis of compound 11a-1 mediated SHP2 inhibition was analyzed.

Guided by the previous SHP2•II-B08 structure (Zhang et al., 2010, Salicylic acid-based small molecule inhibitor for the oncogenic Src homology-2 domain containing protein tryosine phosphatase-2 (SHP2), J. Med. Chem. 53, pp. 2482-2493) and the current SHP2•11c-9 structure, the molecular basis of compound 11a-1-mediated SHP2 inhibition was analyzed by carrying out docking studies within the area that covers both II-B08 and 11c-9 around the SHP2 active site.

Docking studies. The 3D-structure of compound 11a-1 was built and energy-minimized using Chem3D program, and three SHP2 catalytic domain structures, 3B7O.pdb (Barr et al., 2009, Large-scale structural analysis of the classical human protein tyrosine phosphatome, Cell 136, pp. 352-363) (apo form SHP2 catalytic domain), 3O5X.pdg (Zhang et al., 2010, Salicylic acid-based small molecule inhibitor for the oncogenic Src homology-2 domain containing protein tyrosine phosphatase-2 (SHP2), J. Med. Chem. 53, pp. 2482-2493) (SHP2•II-B08 complex structure), and 4 PVG.pdb (SHP2•11c-9 complex structure), were used for ensemble docking in the AutoDock4.2.5 software suite (Morris et al., 2009, AutoDock 4 and AutoDock Tools4: Automated Docking with Selective Receptor Flexibility, Journal of Computational Chemistry 30, pp. 2785-2791). The ligand and receptor were pre-docking processed following the AutoDock Tools.4.6 program (Sanner, 1999, Python: A programming language for software integration and development. Journal of Molecular Graphics & Modelling 17, pp. 57-61) (e.g., merge non-polar hydrogens, add Gasteiger charges, set rotatable bond for ligand, and add solvation parameter for receptor).

To define the common docking area, the above two SHP2 complex structures were superimposed onto the apo form of SHP2, a rectangle docking area was visually set to adequately cover both II-B08 and 11c-9 around the active site, the energy grid size was set to 54×54×36 points with 0.375 Å spacing on each axis, and the energy grid maps for each atom type (i.e., A, C, I, OA, N, SA and HD), as well as the electrostatics and de-solvation maps were calculated using the AutoGrid4. The molecular docking were carried out using AutoDock4.2.5, the optimal binding conformation was determined by Lamarckian Genetic Algorithm with Local Search (LGALS) with the following parameters during each docking run: energy evaluations of 2500000, population size of 100, mutation rate of 0.02, crossover rate of 0.8, Solis and Wets local search iterations of 300 with probability of 0.06.

For each SHP2 structure, 200 docking runs were performed and the resulted binding modes were conformation-clustered and energy-ranked. The final binding mode was determined by visual inspections, cluster analyses and energy comparisons.

Figure 5A:
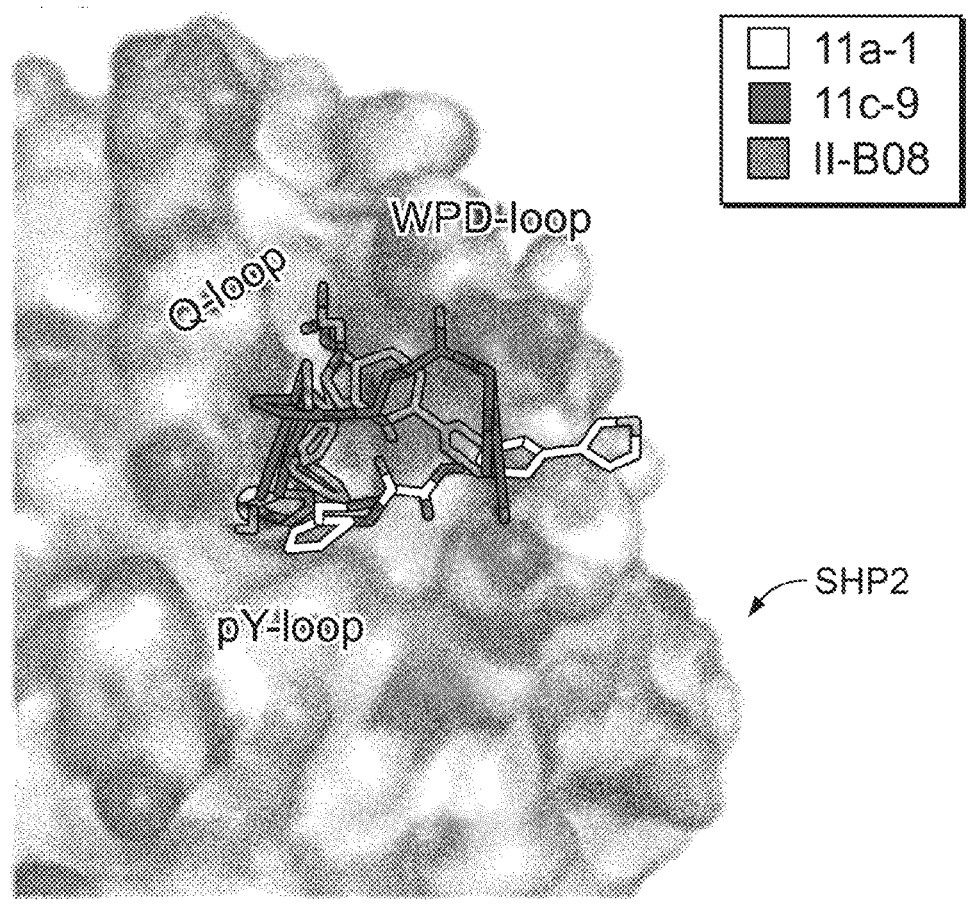
FIGS. 5A-5E depict the likely SHP2 binding mode for 11a-1 revealed by molecular docking as analyzed in Example 3.
Figure 5B:
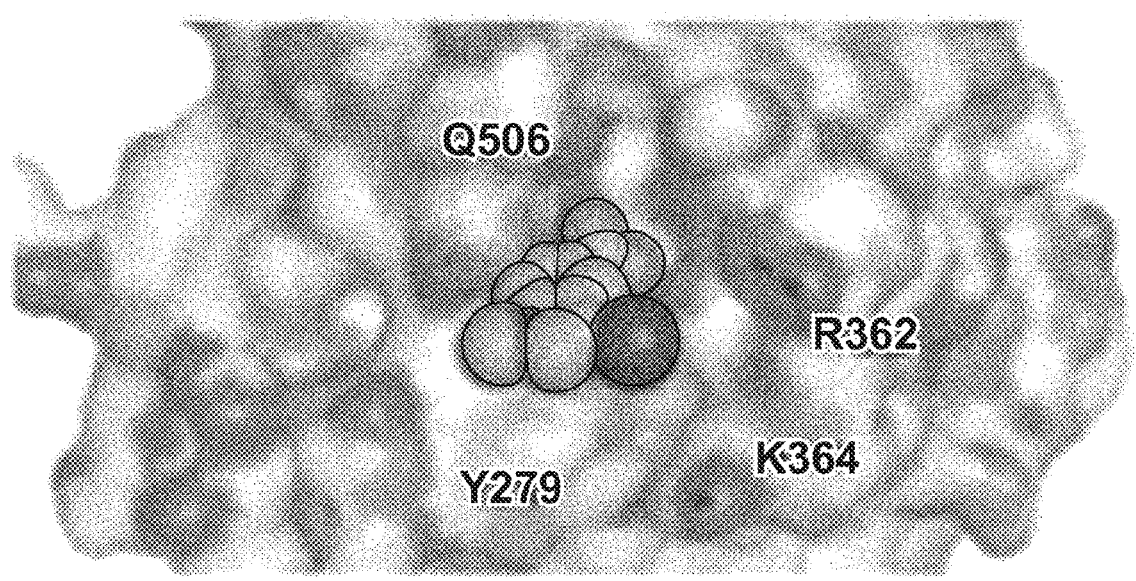
Figure 5C:
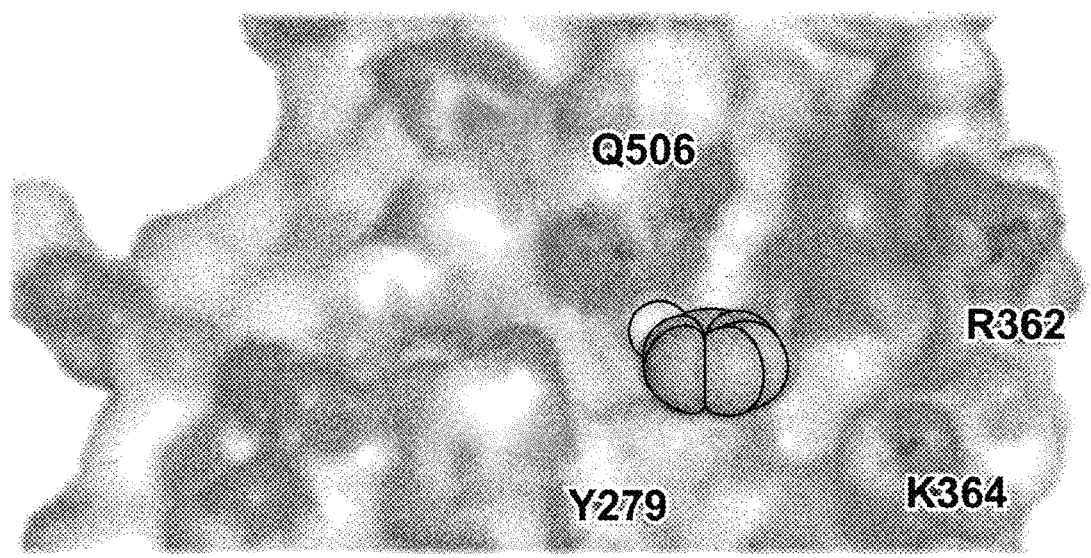

As shown in FIG. 5A, the overall SHP2 binding mode of 11a-1 is similar to those of II-B08 and 11c-9. In all three cases, the hydroxyindole carboxylic acid motif penetrates into the active site, and the distal heterocycle tail interacts with a groove formed by residues in the $\beta_5$-$\beta_6$ loop. However, unlike II-B08 or 11c-9, which extend their heterocycle tail to the groove via their flexible linkers primarily along the Q-loop and WPD-loop, compound 11a-1 spreads its tail through the rigid oxalic linker along the pY recognition loop. Consequently, the hydroxyindole carboxylic acid in 11a-1 binds more deeply into the active site along the pY recognition cleft, occupies most of the active site pocket (FIG. 5B), and the adjacent β-phenyl ring forms strong π-π stacking interaction with Y279 in the pY recognition loop (FIG. 5C), which is not observed in SHP2•II-B08 and SHP2•11c-9 structures.

Figure 5D:
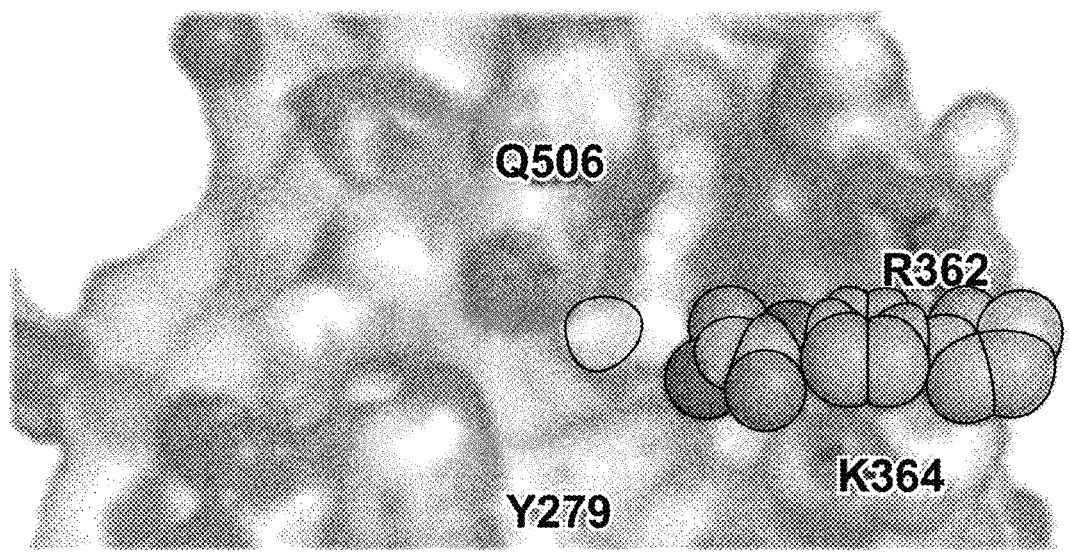
Figure 5E:
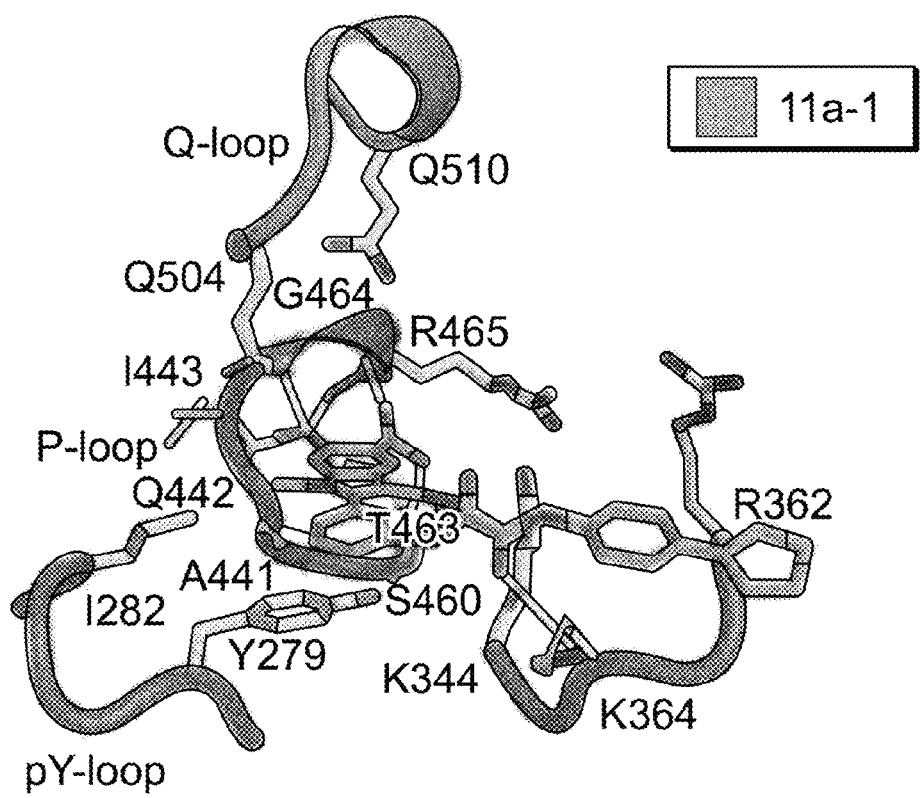

In addition, the oxalamide linker properly places the phenylthiophene tail to be well sandwiched by R362 and K364 in the $\beta_5$-$\beta_6$ loop (FIG. 5D). In more detail (FIG. 5E), the hydroxyindole carboxylic acid forms four H-bonds with the backbone amides of S460, I463, G464 and R465 in the P-loop, which anchors the indole core in the active site to be in Van der Waals contacts with several P-loop residues; the 1-methyl group makes hydrophobic interactions with A461, Y279 and I282 and the β-phenyl ring π-π stacks with Y279; and one of the carbonyls within the oxalamide linker forms H-bond with the side chain of K364, which thus orients the phenylthiophene tail between R362 and K364 in the $\beta_5$-$\beta_6$ loop. Collectively, the increased and more favorable interactions between 11a-1 and SHP2 likely contribute to 11a-1's enhanced inhibition potency and selectivity toward SHP2. In support of the docking analysis, the $IC_{50}$ values of 11a-1 for SHP2/R362A and SHP2/K364S are 2.2 and 1.3-fold higher than that of the wild-type enzyme, indicating that R362 and K364 likely participate in binding 11a-1.

Example 4

In this Example, the ability of compound 11a-1 to inhibit SHP-2 dependent signaling and proliferation in cancer cell lines was analyzed.

Given the excellent potency and selectivity of compound 11a-1 toward SHP2, the ability to inhibit SHP2-dependent signaling and proliferation in a number of cancer cell lines was evaluated. It has previously been demonstrated that SHP2 is required for growth of H1975 (Xu et al., 2013, Targeting SHP2 for EGFR inhibitor resistant non-small cell lung carcinoma. Biochem. Biophys. Res. Commun., 439, pp. 586-590), a non-small cell lung cancer (NSCLC) patient derived cell line with secondary gatekeeper mutations in EGF receptor and showing resistance to EGF receptor inhibitors gefitinib and erlotinib.

Particularly, human non-small cell lung carcinoma cell line H1975 was obtained from the American Tissue Culture Collection and cultured at 37° C. and 5% $CO_2$ in RPMI-1640 (Corning, Corning, N.Y.) supplemented with 10% fetal bovine serum. $3 \times 10^3$ cells were seeded in each well of 96-well plates. After treatment with compound 11a-1 for 2 days, cells were incubated with 50 μg/ml MTT (3-(4,5-Dimethylthiazol-2-yl)-2,5-diphenyltetrazolium bromide (Sigma, St. Louis, Mo.) for 3-4 hours. Then, the culture medium was removed, DMSO was added to dissolve the formazan crystals. Wells containing only media were used for background correction. The optical density was measured spectrophotometrically at 540 nm.

For biochemical studies, H1975 cells were serum-starved overnight followed by treatment with vehicle or compound 11a-1 for 3 hours, and then either left unstimulated or stimulated with 5 ng/ml EGF (Sigma, St. Louis, Mo.) for 60 minutes. Lysates were then resolved by SDS-PAGE and the protein phosphorylation levels were detected by immunoblot analysis. Specifically, cells were lysed in lysis buffer (1.0% Nonidet P-40, 50 mM Tris-HCl (pH 7.4), 150 mM NaCl, 5 mM EDTA, 2 mM NaVO3, 10 mM NaF) plus a protease inhibitor mixture available from Roche (Basel, Switzerland) and centrifuged at 10,000 rpm for 5 minutes at 4° C. Supernatants were collected and protein concentration was determined using the BCA protein assay (ThermoFisher Scientific, Rockford, Ill.). Equal amount of protein extracts were mixed with gel loading buffer and separated on SDS-PAGE. After electrophoresis, the proteins were transferred onto nitrocellulose membranes and nonspecific binding was blocked with 5% nonfat dry milk in Tris-buffered saline containing 0.1% Tween-20 (TBS-T). Membranes were then probed with various antibodies overnight at 4° C. on a rocker. After incubation, membranes were washed with TBS-T and incubated with appropriate horseradish peroxidase (HRP)-conjugated secondary antibodies for 1 hour at room temperature. Finally, the proteins on the membranes were detected using SuperSignal West Dura Luminol/Enhancer solution (ThermoFisher Scientific, Rockford, Ill.) and membranes were analyzed using Bio-Rad ChemiDoc XRS Imaging System.

Figure 6A:
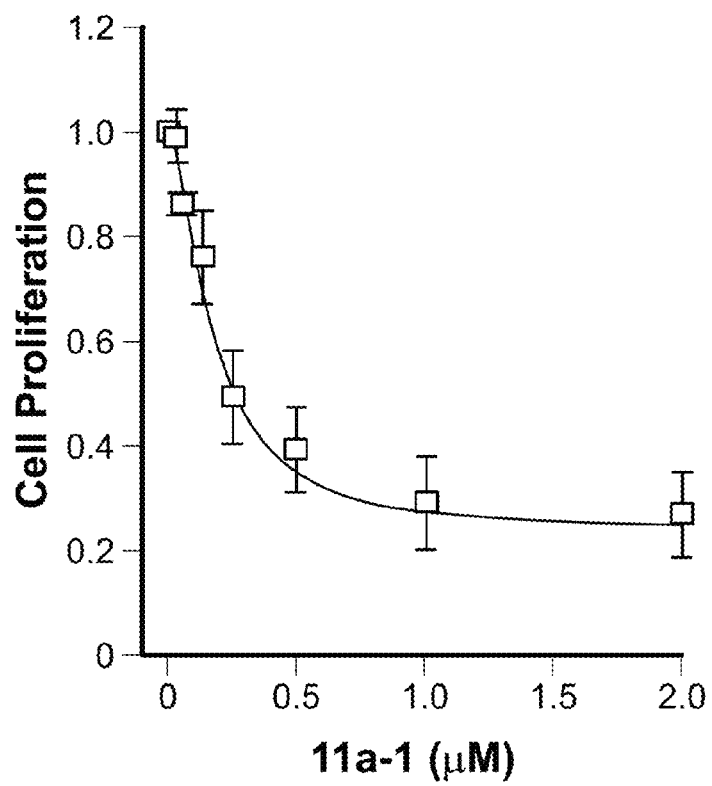
FIGS. 6A-6E show that the SHP2 inhibitor 11a-1 reduced lung cancer cell proliferation and specifically blocked SHP2-dependent signaling as analyzed in Example 4.

After treatment of H1975 cells with compound 11a-1 for 2 days, as shown in FIG. 6A, compound 11a-1 inhibited H1975 cell proliferation (measured by the MTT assay) in a dose-dependent manner with an $IC_{50}$ of 0.17±0.02 μM.

Figure 6B:
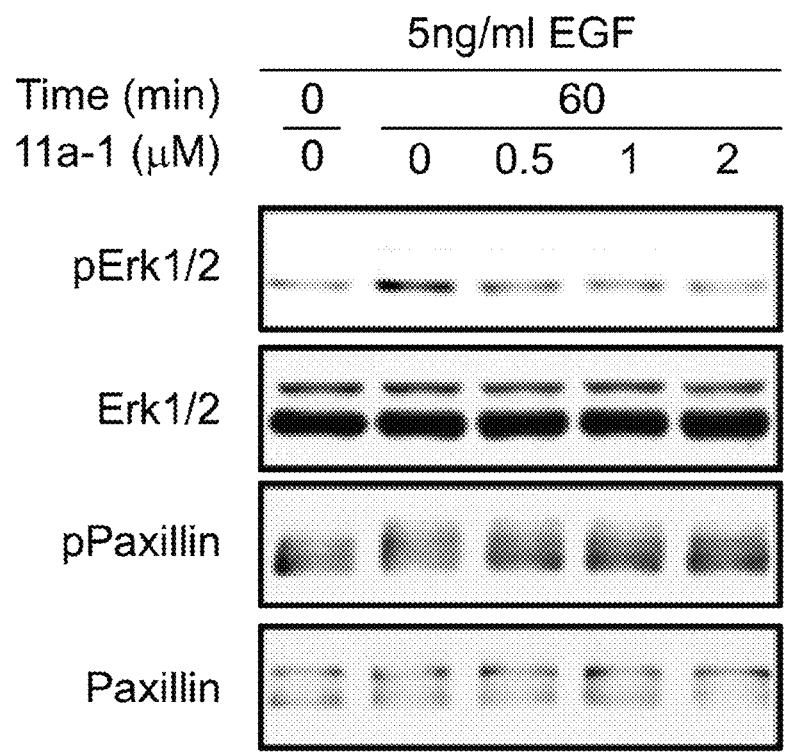

Since SHP2 phosphatase activity is required for the full activation of the Ras-Erk1/2 pathway, the cellular effect of compound 11a-1 on EGF-induced Erk1/2 activation in H1975 cells was further evaluated. Compound 11a-1 effectively reduced the EGF-induced Erk1/2 phosphorylation in a dose-dependent manner (FIG. 6B). To further provide direct evidence that compound 11a-1 can block the phosphatase activity of SHP2 inside the cell, the phosphorylation level of Paxillin (pY118), a physiological substrate of SHP2 whose dephosphorylation by SHP2 enhances EGF-stimulated Erk1/2 activation, was measured. As shown in FIG. 6B, treatment of H1975 cells with compound 11a-1 dose-dependently increased Paxillin phosphorylation on Y118, which is consistent with the decreased EGF-induced Erk1/2 activation in the presence of compound 11a-1.

Figure 6C:
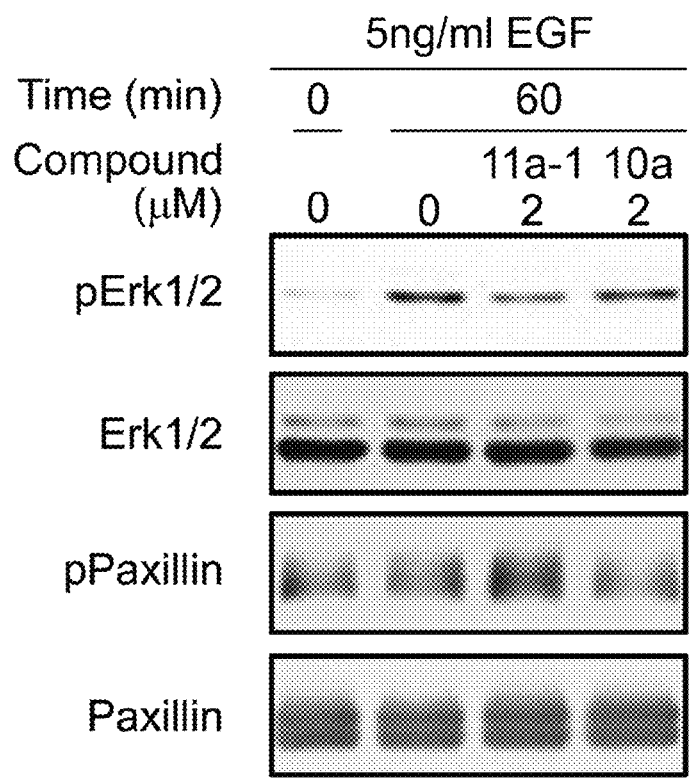
Figure 6D:
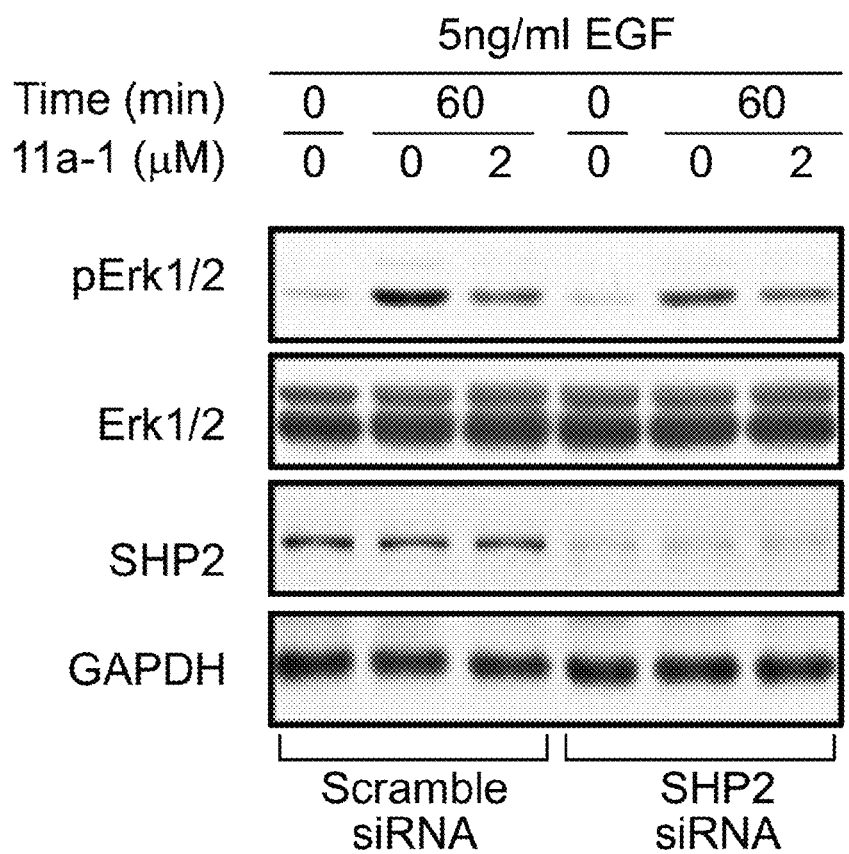
Figure 6E:
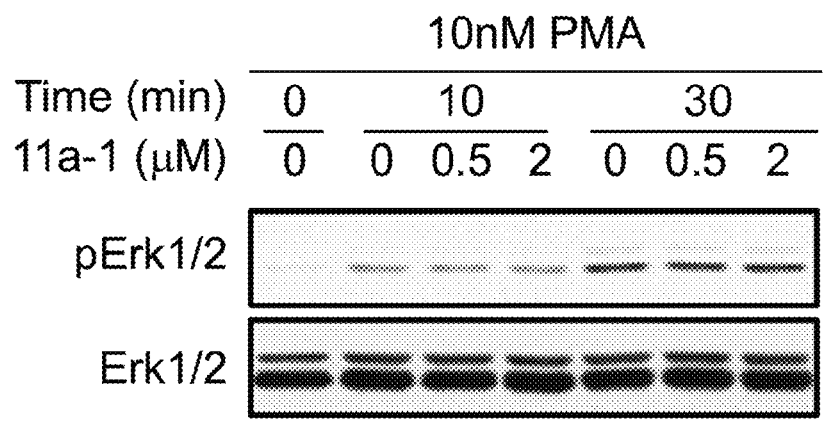

Additionally, to ensure that the cellular activity of compound 11a-1 is manifested through SHP2 inhibition and not due to nonspecific effects, a structurally related but significantly less inhibitory compound 10a ($IC_{50}$ of 14.4 μM for SHP2, Table 2) was also evaluated. At 2 μM, compound 10a exerted no effect on Paxillin and Erk1/2 phosphorylation, while, at the same concentration, compound 11a-1 reduced Erk1/2 phosphorylation by 40% and augmented Paxillin phosphorylation by 30% (FIG. 6C). Moreover, the ability of compound 11a-1 to attenuate EGF-mediated Erk1/2 activation was blunted when the level of SHP2 was knocked down with siRNA (FIG. 6E).

To provide further evidence that the observed cellular effect of compound 11a-1 is SHP2 dependent, the effect of compound 11a-1 on PMA (phorbol 12-myristate 13-acetate)-induced Erk1/2 activation, which is SHP2 independent and instead depends on the activation of protein kinase C and Raf in a Ras-independent manner, was evaluated. Thus, SHP2 inhibitors would not be expected to affect PMA-induced Erk1/2 phosphorylation. Indeed, compound 11a-1 had no effect on PMA-induced Erk1/2 phosphorylation (FIG. 6D). Taken together, these results indicate that compound 11a-1 specifically inhibits SHP2-mediated cellular signaling events.

Example 5

In this Example, the ability of compound 11a-1 to block growth of breast cancer cells was evaluated.

The promising activity of 11a-1 in inhibiting H1975 lung cancer cell proliferation spurred an investigation into its effectiveness on inhibiting the growth of the ErbB2 positive SKBR3 breast cancer cell line. These cells, through upregulation of ErbB2, strongly activate Ras, which then promotes either Akt signaling when grown on plastic or Erk1/2 signaling when growth in Matrigel. Given the multitude of studies that show that cancer cells grow in Matrigel as a mass that much more closely models the formation and signaling properties of real human tumors, the effectiveness of compound 11a-1 in blocking the growth of these cells in Matrigel was determined.

Approximately 300,000 SKBR3 cells were seeded into 150 µl of growth factor reduced Matrigel (Corning, Corning, N.Y.) in 35 mm dishes. To 3 dishes for each condition, 2 mL of media containing either 10 µl vehicle (DMSO) or compound 11a-1 at the indicated concentration was then added. Every 24 hours, the cells were imaged with a NIKON SMZ1500 stereomicroscoppe. The cross-sectional area of individual colonies from each image were measured using Adobe Photoshop software. After 4 days, the cells were recovered from the Matrigel and lysed in PLC buffer containing protease inhibitor cocktail (Cat. No. P8340; Sigma-Aldrich, St. Louis, Mo.). Lysates were then resolved by SDS-PAGE and relative levels of the indicated proteins were detected by immunoblot analysis.

Figure 7A:
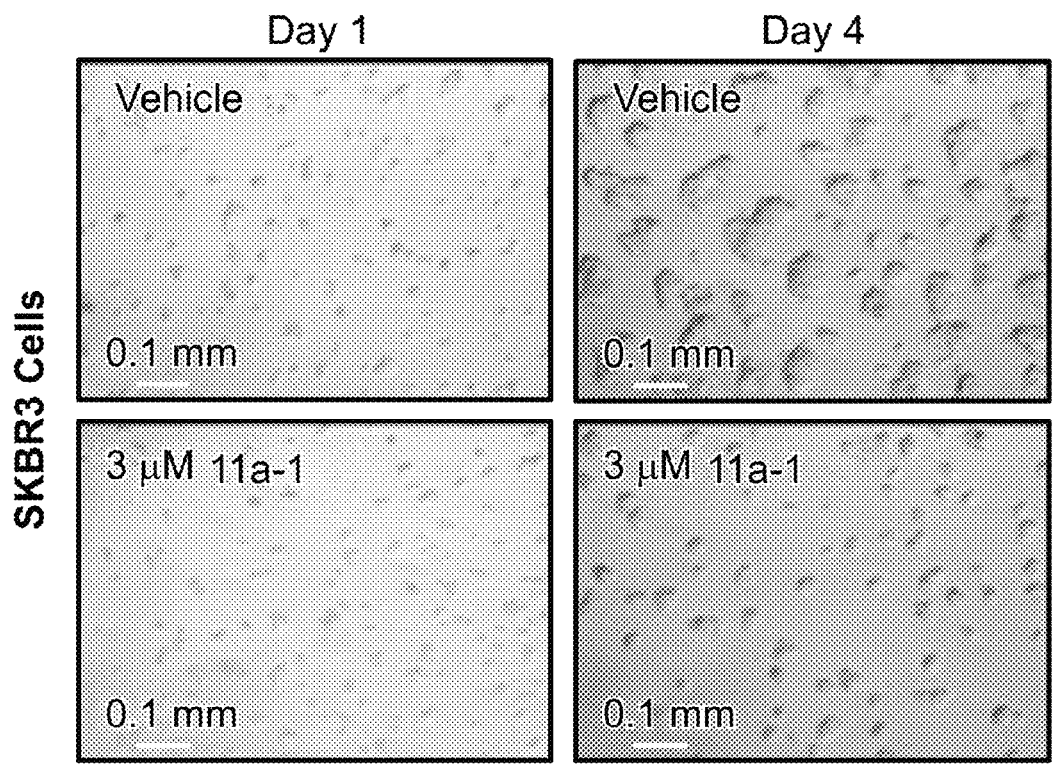
FIGS. 7A & 7B show that compound 11a-1 inhibited Erk1/2 and Akt activity and ErbB2+ breast cancer cell growth in a 3D Matrigel environment as analyzed in Example 5.

Consistently, SKBR3 cells formed tumor like growths in Matrigel treated with vehicle, but their growth within 24 hours was potently inhibited by 3 µM of compound 11a-1 (FIG. 7A).

Figure 7B:
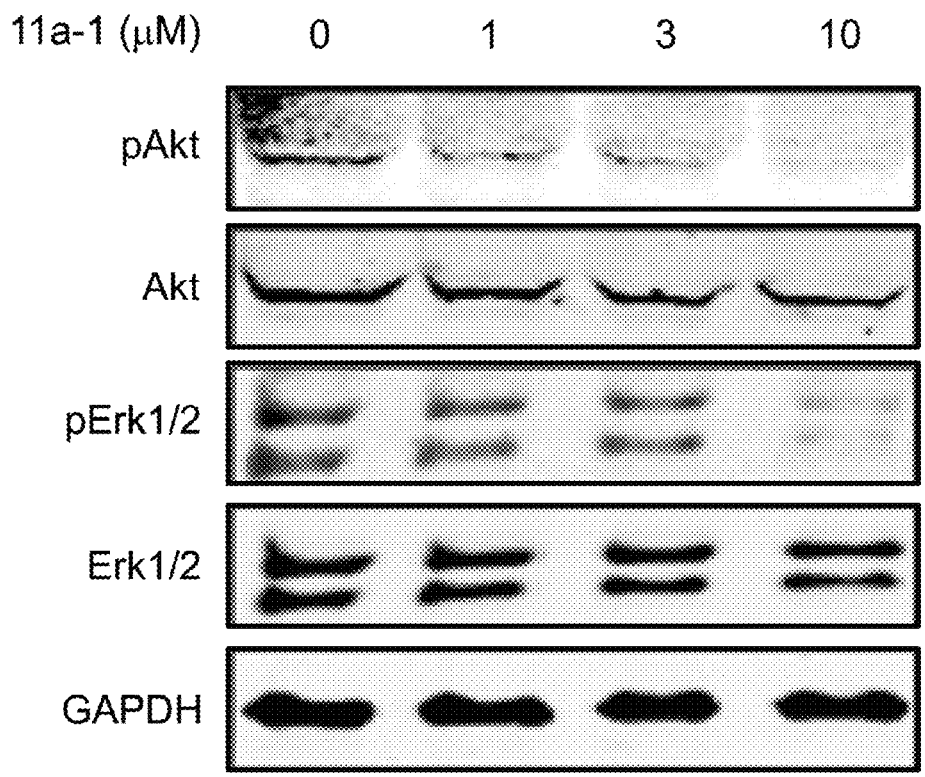

Further, while both control- and compound 11a-1-treated cells showed equivalent levels of total Erk1/2 and Akt over 4 days, their levels of phosphorylation was concordantly inhibited by increasing concentrations of compound 11a-1 from 1 µM to 10 µM (FIG. 7B). Taken together, this data showed that compound 11a-1 potently inhibited the growth of the ErbB2 positive SKBR3 cell line most likely through its ability to block SHP2 dependent Erk1/2 and Akt activation.

Example 6

In this Example, the growth of oncogenic KITD814V bearing 32D myeloid cells in the presence of II-B08 or compound 11a-1 were analyzed and compared.

Gain-of-function mutations in KIT receptor (KITD814V) in humans are associated with gastrointestinal stromal tumors, systemic mastocytosis, and acute myelogenous leukemia. It has been previously shown that first generation SHP2 inhibitor II-B08 suppressed the growth of oncogenic KITD814V induced ligand independent growth (Mali et al., 2012, Role of SHP2 phosphatase in KIT-induced transformation: identification of SHP2 as a druggable target in diseases involving oncogenic KIT, Blood 120, pp. 269-2678).

To further determine the efficacy of compound 11a-1, the growth of oncogenic KITD814V bearing 32D myeloid cells in the presence of II-B08 and 11a-1 were compared. Specifically, the wild-type (WT) KIT and KITD814V were inserted into the bicistronic retroviral vector, MIEG3, upstream of the internal ribosome entry site (IRES) and the enhanced green fluorescent protein (EGFP) gene as previously described in Mali et al., 2012. Retroviral supernatants for transduction of 32D myeloid cells and primary hematopoietic stem and progenitor cells were generated using Phoenix ecotropic packaging cell line transfected with retroviral vector plasmids using a calcium phosphate transfection kit (Invitrogen, Carlsbad, Calif.). Supernatants were collected 48 hours after transfection and filtered through 0.45 µm membranes. 32D myeloid cells were infected twice at 24-hour intervals with 2 mL high/titer virus supernatant in the presence of 10 ng/mL IL-3 and 8 µg/mL polybrene. Forty-eight hours after infection, 32D cells expressing WT KIT or KITD814V receptors were sorted to homogeneity based on EGFP expression and utilized to perform all of the experiments.

Figure 8A:
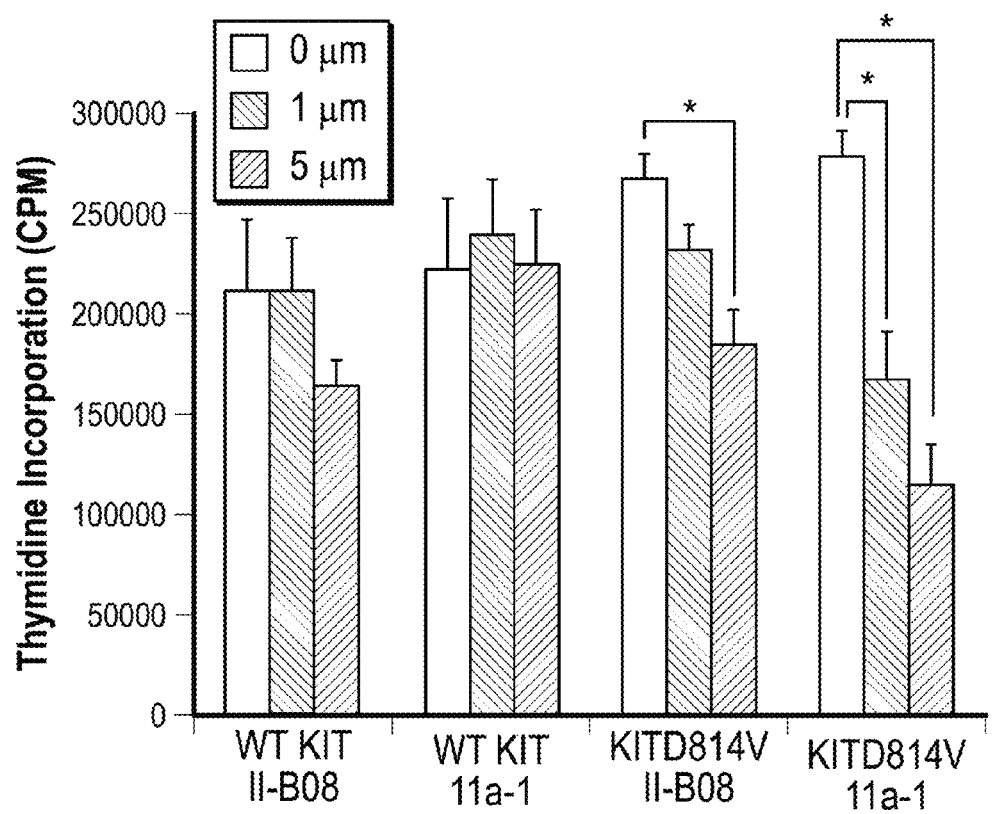
FIG. 8A is a graph depicting 32D myeloid cells bearing wild-type (WT) KIT or KITD814V that were starved of serum and growth factors for 6 hours and subjected to proliferation assay in the presence or absence of the indicated concentration of II-B08 or 11a-1 as analyzed in Example 6. Assay was performed in the presence of IL-3 (10 ng/mL) for cells bearing WT KIT and in the absence of growth factors for cells bearing oncogenic KITD814V. Bars denote the mean thymidine incorporation (CPM±SEM) consolidated from four independent experiments performed in triplicate. *p<0.05.

As seen in FIG. 8A, no significant suppression in the growth of WT KIT bearing cells in the presence of II-B08 or compound 11a-1 were seen at the tested concentrations. However, treatment with II-B08 at 5 µM showed significant suppression in ligand independent growth of KITD814V bearing cells, but not at 1 µM concentration. Furthermore, treatment with compound 11a-1 showed significant inhibition of ligand independent growth of KITD814V bearing cells at both 1 µM and 5 µM concentrations.

To further determine the effect of II-B08 and compound 11a-1 on primary bone marrow cells bearing oncogenic KITD814V, primary low density bone marrow cells from C57BL/6 mice were transduced with KITD814V and sorted cells were subjected to a proliferation assay in the presence or absence of the SHP2 inhibitors, II-B08 and compound 11a-1. To express WT KIT and KITD814V receptors in bone marrow cells, low density bone marrow cells were collected from WT mice, and pre-stimulated in IMDM supplemented with 20% FBS, 2% penicillin/streptomycin, and cytokines (100 ng/mL SCF, 100 ng/mL TPO, 50 ng/mL FLT3-L and 4 ng/mL IL-6) for 48 hours prior to retroviral infection on fibronectin fragments (Retronectin) in non-tissues culture plates. On the third day, cells were infected with 2 mL of high-titer retroviral supernatants for WT KIT or KITD814V prepared as described above. A second shot of viral infection was given 24 hours later. Forty-eight hours after the second infection, cells expressing EGFP were sorted and utilized to perform all experiments.

Figure 8B:
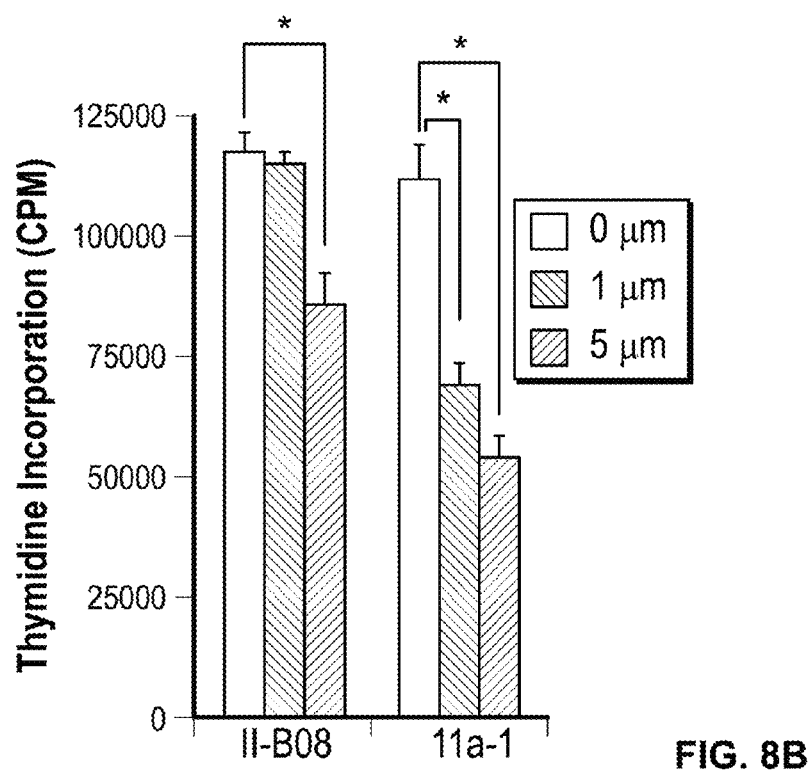
FIG. 8B is a graph depicting WT hematopoietic stem and progenitor cells bearing KITD814V that were starved of serum and growth factors for 6 hours and subjected to proliferation assay in the presence or absence of indicated concentration of II-B08 or 11a-1 as analyzed in Example 6. Bars denote the mean thymidine incorporation (CPM±SD) performed in triplicate from one experiment. *p<0.05.

Similar to 32D myeloid cells, primary bone marrow cells bearing KITD814V showed significant reduced growth in the presence of compound 11a-1 compared to II-B08 at both 1 µM and 5 µM concentrations (FIG. 8B). These results suggest that compound 11a-1 is more potent in inhibiting oncogenic KITD814V induced constitutive growth compared to II-B08.

Figure 8C:
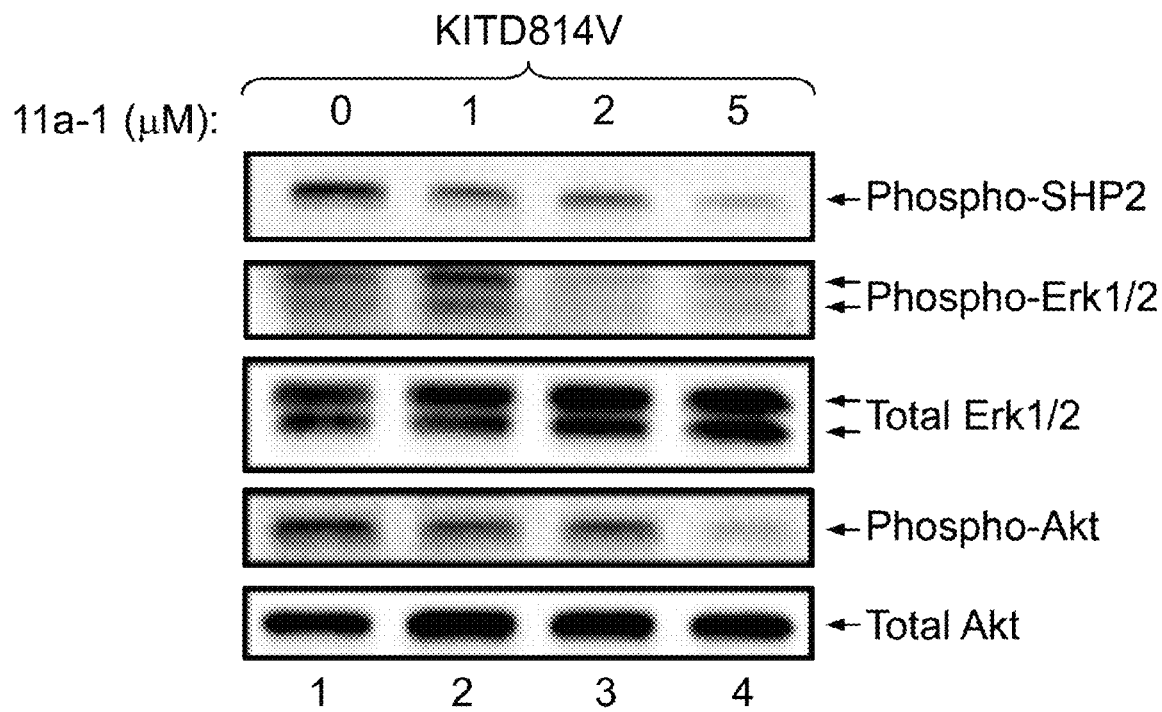
FIG. 8C depicts 32D myeloid cells bearing KITD814V that were starved of serum and growth factors for 6 hours and incubated with the indicated concentration of 11a-1 for 2 hours as analyzed in Example 6. After treatment, cells were lysed and equal amount of protein lysates were subjected to western blot analysis using indicated antibodies.
Figure 9:
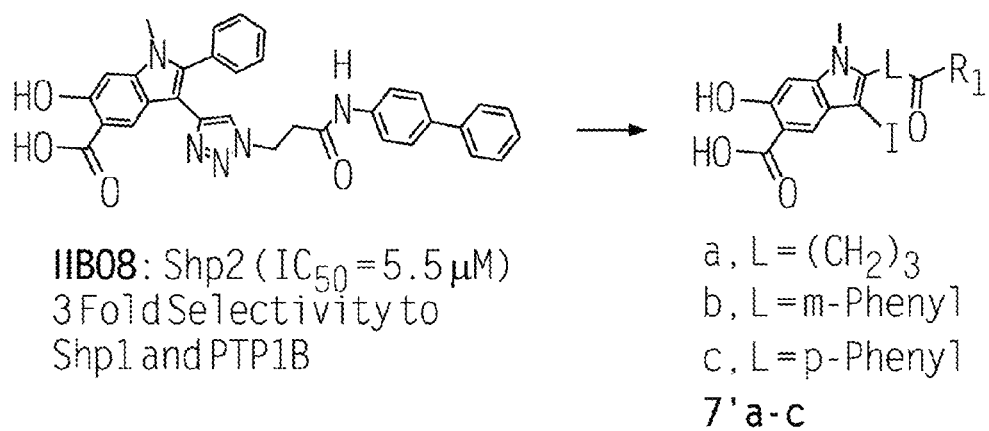
FIG. 9 is a schematic illustrating the strategy and design of hydroxyindole carboxylic acid based SHP2 inhibitor libraries 7'a-c as described in Example 7.
Figure 10:
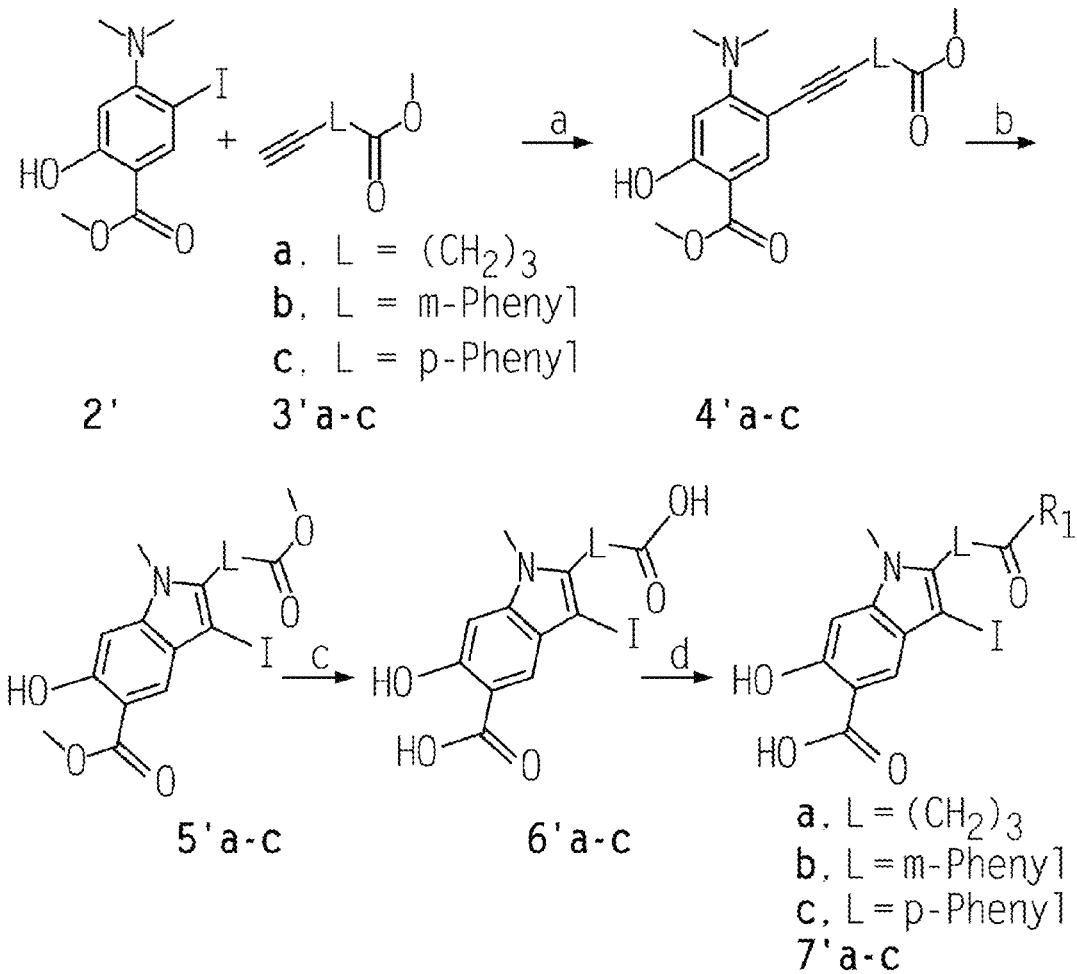
FIG. 10 is a schematic illustrating the design and synthesis of the hydroxyindole carboxylic acid based library 7'a-c (L89, 94, 95).

To determine whether compound 11a-1 also suppressed the ligand independent activation of Akt and Erk1/2 signaling, the 32D myeloid cells bearing WT KIT or KITD814V were starved and treated with compound 11a-1. Consistent with the above results, cells bearing wild-type KIT did not show any constitutive activation of Akt or Erk1/2 in the presence or absence of compound 11a-1 (data not shown). Likewise, constitutive phosphorylation of SHP2, Akt and Erk1/2 was observed in oncogenic KITD814V bearing cells (FIG. 8C, Lane 1). There was dose dependent inhibition of phosphorylation of SHP2, Akt and Erk1/2 in the presence of compound 11a-1 (FIG. 8C, Lanes 2-4). These results suggest that compound 11a-1 inhibited the activation of Akt and Erk1/2 signaling, leading to reduced growth of oncogenic KITD814V bearing cells.

Collectively, the results described above indicate that compound 11a-1 is highly efficacious in blocking SHP2 activity and cell proliferation in H1975 lung cancer cells, ErbB2 positive SKBR3 breast cancer cells, and oncogenic KITD814V bearing 32D myeloid cells and primary low density bone marrow cells.

The above Examples show that the hydroxyindole carboxylic acid-based inhibitors of the present disclosure display highly efficacious cellular activity and can specifically block the SHP2-dependent signaling inside the cell. Thus, these inhibitor compounds not only serve as promising candidates for the development of agents for a wide range of neoplastic disorders, but also as useful tools to interrogate the function of SHP2 in normal physiology and to elucidate the events underlying SHP2-evoked transformation. Obtaining this knowledge is vital for understanding SHP2-mediated oncogenic mechanisms, and for the development of anti-cancer and anti-leukemia therapies targeted to SHP2.

The below methods and compounds were used for Examples 7-8.

Materials and General Procedures. p-Nitrophenyl phosphate (pNPP) was purchased from ThermoFisher Scientific (Rockford, Ill.). For organic synthesis, reagents were used as purchased (Aldrich, Acros, Alfa Aesar, TCI), except where noted. $^1$H and $^{13}$C NMR spectra were obtained on Brucker 500 spectrometers with TMS or residual solvent as standard. All column chromatography was performed using Dynamic Adsorbents 230-400 mesh silica gel ($SiO_2$) with the indicated solvent system unless otherwise noted. TLC analysis was performed using 254 nm glass-backed plates and visualized using UV light (254 nm), low-resolution mass spectra and purity data were obtained using an Agilent Technologies 6130 Quadrupole LC/MS. High resolution Mass spectrum data were collected on Agilent 6520 Accurate-Mass Q-TOF LC/MS. HPLC purification was carried out on a Waters Delta 600 equipped with a Sunfire Prep C18 OBD column (30 mm*150 mm, 5 μm) with methanol-water (both containing 0.1% TFA) as mobile phase. The purity of all final tested compounds was established to be >95% by Agilent Technologies 6130 Quadrupole LC/MS (UV, λ=254 nm).

General method for the synthesis of 4'a-c. A mixture of Methyl 4-(dimethylamino)-2-hydroxy-5-iodobenzoate 2' (321 mg, 1 mmol), compound 3'a-c (2 mmol), TEA (228 μL, 2 mmol), bis(triphenylphosphine)palladium(II) chloride (70.2 mg, 0.1 mmol) and CuI (38 mg, 0.2 mmol) were loaded in a flask, which was degassed and back-filled with nitrogen. DMF (5 mL) was added. The resulting mixture was stirred under a nitrogen atmosphere at room temperature for 4 hours. The reaction was monitored by TLC to establish completion. The solution was partitioned between EtOAc (40 mL) and brine (40 mL). The organic layers were washed with brine (3×40 mL), dried over sodium sulfate, and concentrated in vacuum. The residue was purified by flash silica chromatography (Hex/EtOAc=8:1) to afford compound 4'a-c.

Methyl 4-(dimethylamino)-2-hydroxy-5-(6-methoxy-6-oxohex-1-yn-1-yl)benzoate (4'a)

Colorless oil (200 mg, 62%); $^1$H NMR (500 MHz, $CDCl_3$): δ 10.87 (s, 1H), 7.83 (s, 1H), 6.31 (s, 1H), 3.91 (s, 3H), 3.70 (s, 3H), 3.05 (s, 6H), 2.51 (m, 4H), 1.96 (m, 2H); HRMS (ESI): (M−H)$^-$ calcd for $C_{17}H_{20}NO_5$: 318.1347, found: 318.1343; LC-MS (ESI): 320.2 (M+H)$^+$; Purity: >95% (UV, λ=254 nm).

Methyl 4-(dimethylamino)-2-hydroxy-5-((3-(methoxycarbonyl)phenyl)ethynyl)benzoate (4'b)

White solid (257 mg, 73%); $^1$H NMR (500 MHz, $CDCl_3$): δ 10.96 (s, 1H), 8.17 (s, 1H), 7.99 (m, 2H), 7.67 (m, 1H), 7.44 (m, 1H), 6.35 (s, 1H), 3.96 (s, 3H), 3.94 (s, 3H), 3.17 (s, 6H); LC-MS (ESI): 354.0 (M+H)$^+$, 351.8 (M−H)$^-$; Purity: >95% (UV, λ=254 nm).

Methyl 4-(dimethylamino)-2-hydroxy-5-((4-(methoxycarbonyl)phenyl)ethynyl)benzoate (4'c)

White solid (265 mg, 75%); $^1$H NMR (500 MHz, $CDCl_3$): δ 10.97 (s, 1H), 8.01 (d, J=8.3 Hz, 2H), 7.97 (s, 1H), 7.54 (d, J=8.3 Hz, 2H), 6.33 (s, 1H), 3.94 (s, 3H), 3.93 (s, 3H), 3.15 (s, 6H); $^{13}$C NMR (125 MHz, $CDCl_3$): δ 169.7, 166.5, 162.9, 159.2, 137.6, 130.6, 129.5, 128.9, 128.6, 104.0, 103.5, 102.8, 92.1, 91.9, 52.2, 51.9, 42.6. LC-MS (ESI): 354.0 (M+H)$^+$; Purity: >95% (UV, λ=254 nm).

General method for the synthesis of 5'a-c. To a solution of 4'a-c (1 mmol), $NaHCO_3$ (0.084 g, 1 mmol) in $CH_2Cl_2$ or $CH_3CN$ (100 mL) was added iodine (0.304 g, 1.2 mmol). The resulting mixture was stirred at room temperature for 4 hours, then added 100 mL $CH_2Cl_2$ and washed with saturated aqueous $Na_2SO_3$ solution (2×100 mL), brine (100 mL), dried over $Na_2SO_4$ and concentrated in vacuum. The residue was purified by flash chromatography (Hexane/EtOAc=4:1) to afford 5'a-c.

Methyl 6-hydroxy-3-iodo-2-(4-methoxy-4-oxobutyl)-1-methyl-1H-indole-5-carboxylate (5'a)

Use $CH_3CN$ as solvent, white solid (182 mg, 42%); $^1$H NMR (500 MHz, $CDCl_3$): δ 10.84 (s, 1H), 7.90 (s, 1H), 6.79 (s, 1H), 4.01 (s, 3H), 3.72 (s, 3H), 3.67 (s, 3H), 2.89 (t, J=7.7 Hz, 2H), 2.46 (t, J=7.1 Hz, 2H), 1.96 (m, 2H); $^{13}$C NMR (125 MHz, $CDCl_3$): δ 173.5, 171.2, 157.9, 142.3, 141.5, 123.5, 123.2, 107.0, 95.8, 59.3, 52.1, 51.6, 32.8, 30.8, 26.4, 24.0. LC-MS (ESI): 431.2 (M+H)$^+$; Purity: >95% (UV, λ=254 nm).

Methyl 6-hydroxy-3-iodo-2-(4-(methoxycarbonyl)phenyl)-1-methyl-1H-indole-5-carboxylate (5'c)

Use $CH_2Cl_2$ as solvent, white solid (388 mg, 83%); $^1$H NMR (500 MHz, $CDCl_3$): δ 10.90 (s, 1H), 8.18 (d, J=8.3 Hz, 2H), 7.98 (s, 1H), 7.56 (d, J=8.3 Hz, 2H), 6.80 (s, 1H), 4.01 (s, 3H), 3.98 (s, 3H), 3.58 (s, 3H); $^{13}$C NMR (125 MHz, $CDCl_3$): δ 171.1, 166.5, 158.4, 142.6, 141.5, 135.5, 130.7, 130.4, 129.7, 124.5, 124.1, 107.8, 96.2, 60.6, 52.3, 52.2, 32.3.

General method for the synthesis of 6'a-c. Compound 5'a-c (1 mmol) was dissolved in 4 mL of THF. Then 5%

LiOH (4 mL) solution was added. The mixture was heated to 80° C. for 2 hours, cooled to room temperature, diluted by brine (100 mL), acidified by 2 N HCl to pH 5 and extracted with EtOAc (2×100 mL). The organic layers were combined washed with brine, dried over sodium sulfate, concentrated in vacuum and purified by HPLC to give 6'a-c.

2-(3-carboxypropyl)-6-hydroxy-3-iodo-1-methyl-1H-indole-5-carboxylic acid (6'a, Core 89). White solid (333 mg, 82%); $^1$H NMR (500 MHz, DMSO): δ 13.68 (brs, 1H), 12.15 (brs, 1H), 11.26 (s, 1H), 7.70 (s, 1H), 6.95 (s, 1H), 3.71 (s, 3H), 2.82 (t, J=7.5 Hz, 2H), 2.32 (t, J=7.1 Hz, 2H), 1.76 (m, 2H); LC-MS (ESI): 404.0 (M+H)$^+$, 401.8 (M–H)$^-$; Purity: >95% (UV, λ=254 nm).

2-(3-carboxyphenyl)-6-hydroxy-3-iodo-1-methyl-1H-indole-5-carboxylic acid (6'b, Core 94). Yellow solid (223 mg, 51%); $^1$H NMR (500 MHz, DMSO): δ 8.08 (m, 2H), 7.78 (s, 1H), 7.71 (m, 1H), 7.55 (m, 1H), 7.05 (s, 1H), 3.61 (s, 3H); LC-MS (ESI): 435.6 (M–H)$^-$; Purity: >95% (UV, λ=254 nm).

2-(4-carboxyphenyl)-6-hydroxy-3-iodo-1-methyl-1H-indole-5-carboxylic acid (6'c, Core 95). Yellow solid (288 mg, 65%); $^1$H NMR (500 MHz, DMSO): δ 13.20 (brs, 1H), 11.40 (brs, 1H), 8.10 (d, J=8.3 Hz, 2H), 7.87 (s, 1H), 7.67 (d, J=8.3 Hz, 2H), 7.07 (s, 1H), 3.61 (s, 3H); $^{13}$C NMR (125 MHz, DMSO): δ 173.0, 167.3, 158.5, 142.6, 141.6, 135.4, 131.3, 131.2, 129.8, 124.2, 123.8, 108.6, 96.9, 61.5, 32.6. LC-MS (ESI): 435.6 (M–H)$^-$; Purity: >95% (UV, λ=254 nm).

General method for the synthesis of (7'a-1 to 7'a-3 and 7'c-1 to 7'c-3). Compound 7'a or 7'c (0.02 mmol) dissolved in 0.5 mL of DMF was added to a solution of corresponding amines (0.04 mmol), HOBT (3.06 mg, 0.02 mmol), HBTU (7.58 mg, 0.02 mmol), and DIPEA (5.16 µL, 0.04 mmol) in 1 mL of DMF. The mixture was stirred under room temperature for 4 hours. This crude product was purified by Pre-HPLC to give 7'a-1 to 7'a-3 and 7'c-1 to 7'c-3.

2-(4-((3-(benzyloxy)phenyl)amino)-4-oxobutyl)-6-hydroxy-3-iodo-1-methyl-1H-indole-5-carboxylic acid (7'a-1, L89M52). White solid (5.4 mg, 46%); $^1$H NMR (500 MHz, DMSO): δ 13.68 (s, 1H), 11.27 (s, 1H), 9.91 (s, 1H), 7.70 (s, 1H), 7.45-7.31 (m, 6H), 7.18 (m, 1H), 7.10 (m, 1H), 6.96 (s, 1H), 6.69 (m, 1H), 5.05 (s, 2H), 3.73 (s, 3H), 2.85 (m, 2H), 2.39 (m, 2H), 1.87 (m, 2H); LC-MS (ESI): 607.0 (M+Na)$^+$, 582.8 (M–H)$^-$; Purity: >95% (UV, λ=254 nm).

2-(4-((benzo[d][1,3]dioxol-5-ylmethyl)amino)-4-oxobutyl)-6-hydroxy-3-iodo-1-methyl-1H-indole-5-carboxylic acid (7'a-2, L89N79). White solid (5.5 mg, 51%); $^1$H NMR (500 MHz, DMSO): δ 13.68 (s, 1H), 11.26 (s, 1H), 8.30 (s, 1H), 7.70 (s, 1H), 6.95 (s, 1H), 6.83 (m, 2H), 6.72 (m, 1H), 5.97 (m, 2H), 4.17 (m, 2H), 3.69 (s, 3H), 2.79 (m, 2H), 2.23 (m, 2H), 1.78 (m, 2H); LC-MS (ESI): 559.0 (M+Na)$^+$, 534.8 (M–H)$^-$; Purity: >95% (UV, λ=254 nm).

2-(4-((4-(benzyloxy)-3-chlorophenyl)amino)-4-oxobutyl)-6-hydroxy-3-iodo-1-methyl-1H-indole-5-carboxylic acid (7'a-3, L89M50). White solid (5.8 mg, 46%); $^1$H NMR (500 MHz, DMSO): δ 9.92 (s, 1H), 7.75 (m, 1H), 7.69 (m, 1H), 7.46-7.32 (m, 7H), 7.16 (m, 1H), 6.94 (s, 1H), 5.15 (s, 2H), 3.72 (s, 3H), 2.85 (m, 2H), 2.37 (m, 2H), 1.87 (m, 2H); LC-MS (ESI): 641.0 (M+Na)$^+$, 616.8 (M–H)$^-$; Purity: >95% (UV, λ=254 nm).

2-(4-((3-(benzyloxy)phenyl)carbamoyl)phenyl)-6-hydroxy-3-iodo-1-methyl-1H-indole-5-carboxylic acid (7'c-1, L95M52). White solid (8.0 mg, 64%); $^1$H NMR (500 MHz, DMSO): δ 10.41 (s, 1H), 8.10 (m, 2H), 7.88 (s, 1H), 7.70 (m, 2H), 7.61 (s, 1H), 7.48-7.26 (m, 7H), 7.07 (s, 1H), 6.80 (m, 1H), 5.12 (s, 2H), 3.63 (s, 3H); LC-MS (ESI): 619.0 (M+H)$^+$, 616.8 (M–H)$^-$; Purity: >95% (UV, λ=254 nm).

2-(4-((4-(benzyloxy)-3-chlorophenyl)carbamoyl)phenyl)-6-hydroxy-3-iodo-1-methyl-1H-indole-5-carboxylic acid (7'c-3, L95M50). White solid (9.3 mg, 71%); $^1$H NMR (500 MHz, DMSO): δ 10.44 (s, 1H), 8.10 (m, 2H), 8.00 (s, 1H), 7.88 (s, 1H), 7.69 (m, 3H), 7.50-7.26 (m, 6H), 7.07 (s, 1H), 5.22 (s, 2H), 3.63 (s, 3H); LC-MS (ESI): 653.0 (M+H)$^+$, 650.8 (M–H)$^-$; Purity: >95% (UV, λ=254 nm).

Example 7

In this Example, the hydroxyindole carboxylic acids of library 7'a-c were constructed and analyzed for both potency and specificity to SHP2.

To construct amide library 7'a-c, as shown in FIG. 11, compound 2' methyl 4-(dimethylamino)-2-hydroxy-5-iodobenzoate coupled with the corresponding aliphatic or aromatic alkynes 3'a-c by Sonogashira coupling to afford compound 4'a-c with 80-90% yield. Electrophilic cyclizations of 4'a-c by I$_2$ provide iodides 5'a-c in 80-90% yield. Core 6'a-c was provided by the hydrolysis of ester 5'a-c in 5% LiOH under 80° C. for 2 hours. Core 6'a-c reacted with 192 acids (FIGS. 3A and 3B) respectively in the presence of HOBT, HBTU and DIPEA in DMF overnight to assemble the combinatorial amide library 7'a-c in 96-well plates. The reactions were selected randomly and monitored by LC-MS. About 60-80% of Core 6'a-c was converted to target molecules, indicating the good quality of library 7'a-c.

These three libraries were further screened at 10 µM for SHP2. The aromatic linker library 7'b and 7'c had a higher hit rate than the aliphatic linker library 7'a. Three pairs of hits bearing the same amine scaffold from library 7'a and 7'c were resynthesized and purified by HPLC. Their IC$_{50}$ were tested by the inhibition of SHP2 catalyzed hydrolysis of p-nitrophenyl phosphate (pNPP) at pH 7 and 25° C. (Table 1). Consistent with the screening result, all three hits from 7'c were more potent than the hits from 7'a. For example, compound 7'c-3 (IC$_{50}$=1.6 µM) was 12-fold more potent than the closely related compound 7'a-3 (IC$_{50}$>20 µM). Both the profile of IC$_{50}$ data and screening data demonstrated that the aromatic linker was superior to the aliphatic linker.

Example 8

In this Example, SHP2 (D2C) was used to transform into *E. coli* BL21/DE3 and grown in LB medium containing 50 µg/ml kanamycin at 37° C. to an OD$_{600}$ of 0.4. Following the addition of IPTG to a final concentration of 20 µM, the culture was incubated at 20° C. with shaking for an additional 16 hours. The cells were harvested by centrifugation at 5000 rpm for 5 minutes at 4° C. The bacterial cell pellets were resuspended in 20 mM Tris, pH 7.9, 500 mM NaCl, 5 mM imidazole, and were lysed by passage through a French press cell at 1,200 psi twice. Cellular debris was removed by centrifugation at 16,000 rpm for 30 minutes at 4° C. The protein was purified from the supernatant using standard procedures of Ni-nitrilotriacetic acid-agarose (Qiagen) affinity purification. The protein eluted from Ni-NTA column was concentrated with an Amicon Ultra centrifugal filter device (Millipore) and the buffer was changed to 20 mM Tris, pH 7.5, 150 mM NaCl, 1 mM EDTA and 1 mM DTT. Protein concentration was determined using the Bradford dye binding assay (Bio-Rad) diluted according to the manufacturer's recommendations with bovine serum albumin as standard. The purified SHP 2 (D2C) were made to 30% glycerol and stored at −20° C.

Inhibition Study: The inhibition assays were performed at 25° C. in 50 mM 3,3-dimethylglutarate buffer, pH 7.0, containing 1 mM EDTA with an ionic strength of 0.15M adjusted by NaCl. The salicylic acid based library was screened in a 96-well format at 10 μM compound concentration. The reaction was started by the addition of 50 μl of the enzyme to 150 μl of reaction mixture containing the final Km value of pNPP and various concentrations of the inhibitor in 96-well plate. The reaction was quenched after 10 minutes by the addition of 50 μl of 5N NaOH, and then this reaction mixture was detected for absorbance at 405 nm by a Spectra MAX340 microplate spectrophotometer (Molecular Devices). IC50 values were calculated by fitting the absorbance at 405 nm versus inhibitor concentration to the following equation:

$$AI/A0=IC50/(IC50+[I])$$

where AI is the absorbance at 405 nm of the sample in the presence of inhibitor; A0 is the absorbance at 405 nm in the absence of inhibitor; and [I] is the concentration of the inhibitor.

The inhibition constants (Ki) for the inhibitor for SHP2 (D2C) were determined at pH 7.0 and 25° C. The mode of inhibition and Ki value were determined in the following manner. At various fixed concentrations of inhibitor, the initial rate at a series of pNPP concentrations was measured by following the production of p-nitrophenol as describe above, ranging from 0.4- to 3-fold the apparent Km values. The data were fitted to appropriate equations using Sigma-Plot-Enzyme Kinetics to obtain the inhibition constant and to assess the mode of inhibition.

For selectivity studies, the PTPs, including LYP, mPTPA, SHP1-D1C, PTP1B, LMPTP, VHR, Laforin and PTPα-D1D2 were expressed and purified from *E. coli*. The inhibition assay for these PTPs were performed under the same conditions as SHP2 (D2C) except using a different pNPP concentration corresponding to the Km of the PTP studied.

In view of the above, it will be seen that the several advantages of the disclosure are achieved and other advantageous results attained. As various changes could be made in the above inhibitors without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A hydroxyindole carboxylic acid for inhibiting a protein tyrosine phosphatase, the hydroxyindole carboxylic acid comprising formula (I):

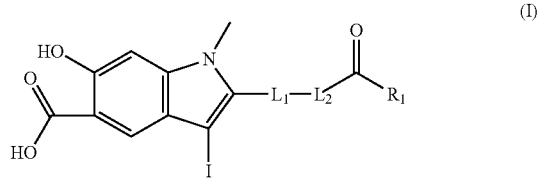

wherein $L_1$ is selected from the group consisting of a single bond, —($C_{1-6}$ alkyl)-, —($C_{2-6}$ alkenyl)-, —($C_{0-6}$ alkyl)-($C_{3-6}$ cycloalkyl)-($C_{0-6}$ alkyl)-, o-phenyl, m-phenyl, p-phenyl, a 3-7 member single aromatic or aliphatic ring, an unsubstituted fused 5-12 member aromatic or aliphatic ring system;

$L_2$ is selected from the group consisting of bond,

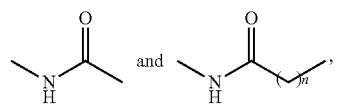

wherein n is 0-3; and $R_1$=NRaRb, wherein Ra or Rb are each independently selected from the group consisting of hydrogen, unsubstituted or substituted alkyl, unsubstituted or substituted cycloalkyl, unsubstituted or substituted heterocyclyl, unsubstituted or substituted aryl, unsubstituted or substituted heteroaryl, and fused 5-12 member aromatic or aliphatic ring system.

2. The hydroxyindole carboxylic acid of claim 1 having an $IC_{50}$ value for a protein tyrosine phosphatase of less than 1 μM.

3. The hydroxyindole carboxylic acid of claim 1, wherein the protein tyrosine phosphatase is selected from the group consisting of Src homology-2 domain containing protein tyrosine phosphatase 2 (SHP2), protein tyrosine phosphatase μ (PTPμ), protein tyrosine phosphatase ε (PTPε), protein tyrosine phosphatase α (PTPα), protein tyrosine phosphatase σ (PTPσ), protein tyrosine phosphatase γ (PTP γ), cytosolic protein tyrosine phosphatases, protein tyrosine phosphatase 1 B (PTP1B), lymphoid protein tyrosine phosphatase (Lyp) Src homology-2 domain containing protein tyrosine phosphatase 1 (SHP 1), protein tyrosine phosphatase H1 (PTP H1), hematopoietic tyrosine phosphatase (HePTP), Striatal-enriched protein tyrosine phosphatase (STEP), protein tyrosine phosphatase PEZ, dual specificity phosphatase, vaccinia H1-related phosphatase (VHR), VH1-like phosphatase Z (VHZ), MAP kinase phosphatase 5 (MKP5), protein phosphatase CDC14A, ubiquitin-like domain-containing CTD phosphatase 1 (UBLCP1), laforin, low molecular weight PTP (LMWPTP), and protein phosphatase SSu72.

4. A hydroxyindole carboxylic acid for inhibiting a protein tyrosine phosphatase, the hydroxyindole carboxylic acid comprising formula (II):

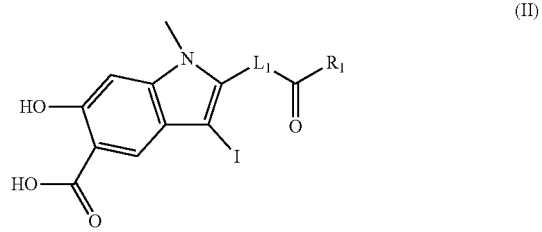

wherein $L_1$ is selected from the group consisting of a single bond, —($C_{1-6}$ alkyl)-, —($C_{2-6}$ alkenyl)-, —($C_{0-6}$ alkyl)-($C_{3-6}$ cycloalkyl)-($C_{0-6}$ alkyl)-, o-phenyl, m-phenyl, p-phenyl, a 3-7 member single aromatic or aliphatic ring, an unsubstituted fused 5-12 member aromatic or aliphatic ring system,; and $R_1$=NRaRb, wherein Ra or Rb are each independently selected from the group consisting of hydrogen, unsubstituted or substituted alkyl, unsubstituted or substituted cycloalkyl, unsubstituted or substituted heterocyclyl, unsubstituted or substituted aryl, unsubstituted or substituted heteroaryl, and fused 5-12 member aromatic or aliphatic ring system.

5. The hydroxyindole carboxylic acid of claim 4 comprising a formula selected from the group consisting of

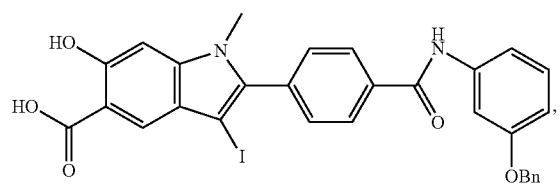

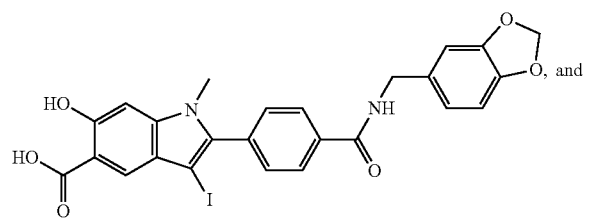

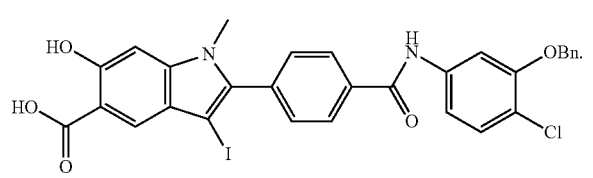

6. The hydroxyindole carboxylic acid of claim 4 having an IC$_{50}$ value for a protein tyrosine phosphatase of less than 1 μM.

7. The hydroxyindole carboxylic acid of claim 4, wherein the protein tyrosine phosphatase is selected from the group consisting of Src homology-2 domain containing protein tyrosine phosphatase 2 (SHP2), protein tyrosine phosphatase μ (PTPμ), protein tyrosine phosphatase ε (PTPε), protein tyrosine phosphatase α (PTPα), protein tyrosine phosphatase σ (PTPσ), protein tyrosine phosphatase γ (PTP γ), cytosolic protein tyrosine phosphatases, protein tyrosine phosphatase 1B (PTP1B), lymphoid protein tyrosine phosphatase (Lyp) Src homology-2 domain containing protein tyrosine phosphatase 1 (SHP 1), protein tyrosine phosphatase H1 (PTP H1), hematopoietic tyrosine phosphatase (HePTP), Striatal-enriched protein tyrosine phosphatase (STEP), protein tyrosine phosphatase PEZ, dual specificity phosphatase, vaccinia H 1 -related phosphatase (VHR), VH1-like phosphatase Z (VHZ), MAP kinase phosphatase 5 (MKP5), protein phosphatase CDC14A, ubiquitin-like domain-containing CTD phosphatase 1 (UBLCP1), laforin, low molecular weight PTP (LMWPTP), and protein phosphatase SSu72.

8. A hydroxyindole carboxylic acid for inhibiting a protein tyrosine phosphatase, the hydroxyindole carboxylic acid comprising formula (III):

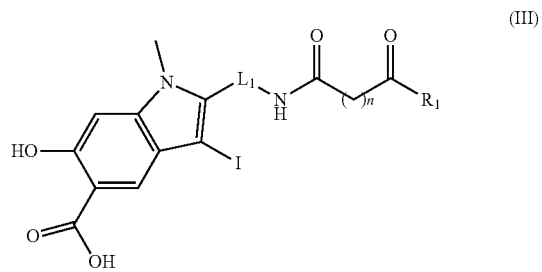

wherein L$_1$ is selected from the group consisting of a single bond, —(C$_{1-6}$ alkyl)-, —(C$_{2-6}$ alkenyl)-, —(C$_{0-6}$ alkyl)-(C$_{3-6}$ cycloalkyl)-(C$_{0-6}$ alkyl)-, o-phenyl, m-phenyl, p-phenyl, a 3-7 member single aromatic or aliphatic ring, an unsubstituted fused 5-12 member aromatic or aliphatic ring system;

n is 0-3; and

R$_1$=NRaRb, wherein Ra or Rb are each independently selected from the group consisting of hydrogen, unsubstituted or substituted alkyl, unsubstituted or substituted cycloalkyl, unsubstituted or substituted heterocyclyl, unsubstituted or substituted aryl, unsubstituted or substituted heteroaryl, and fused 5-12 member aromatic or aliphatic ring system.

9. A hydroxyindole carboxylic acid for inhibiting a protein tyrosine phosphatase, the hydroxyindole carboxylic acid comprising formula (IV):

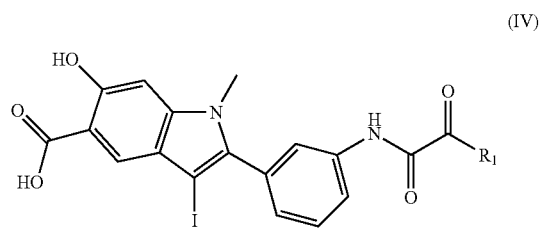

wherein R$_1$=NRaRb, wherein Ra or Rb are each independently selected from the group consisting of hydrogen, unsubstituted or substituted alkyl, unsubstituted or substituted cycloalkyl, unsubstituted or substituted heterocyclyl, unsubstituted or substituted aryl, unsubstituted or substituted heteroaryl, and fused 5-12 member aromatic or aliphatic ring system.

10. The hydroxyindole carboxylic acid of claim 9 having a formula selected from the group consisting of

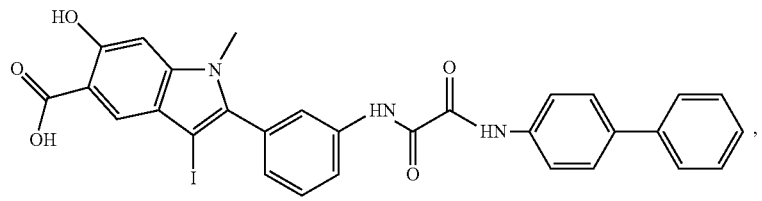

-continued
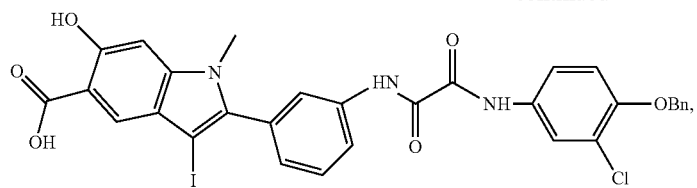
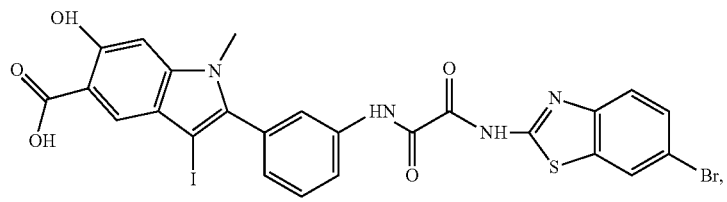
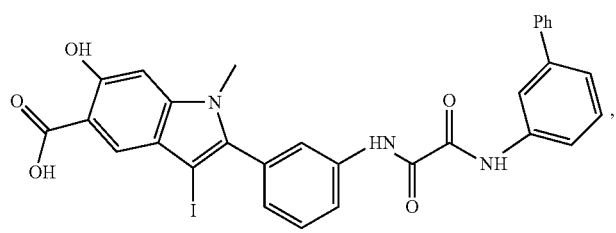
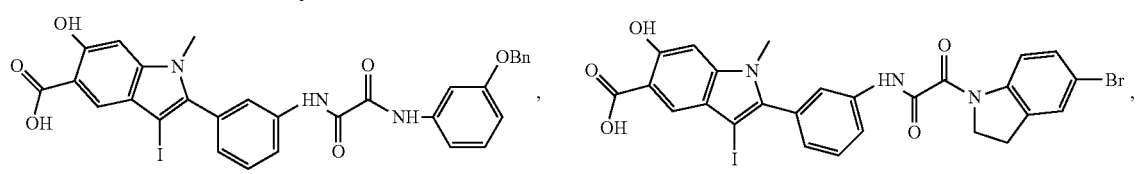
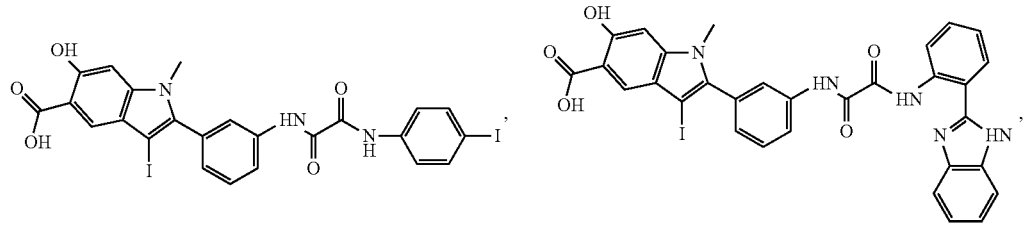
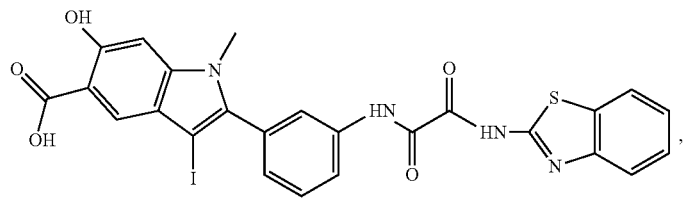
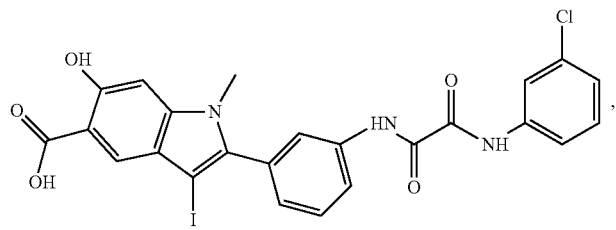
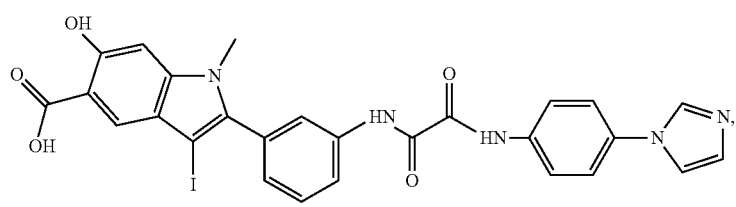

-continued
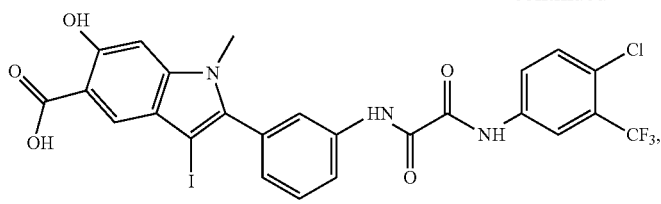
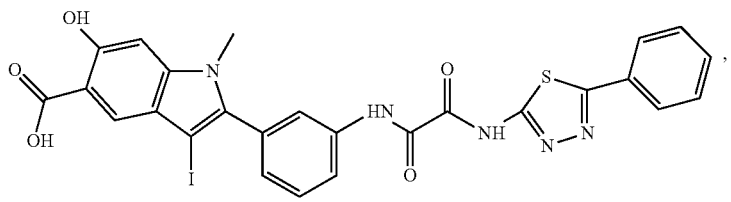
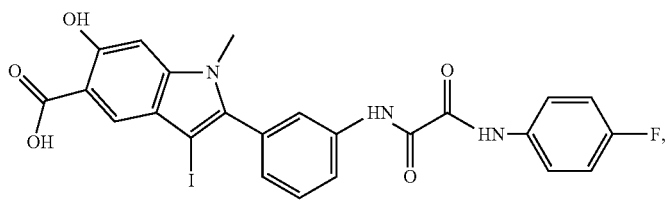
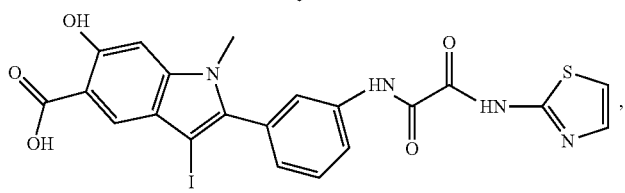
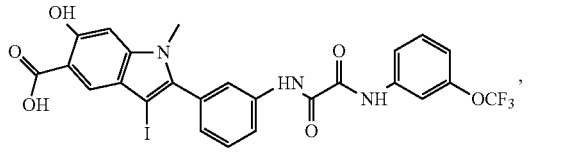
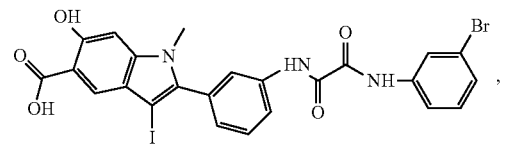
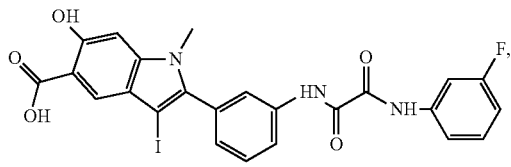
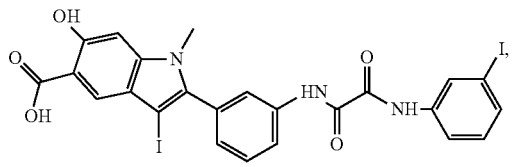
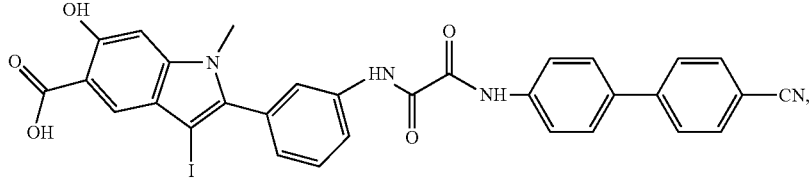
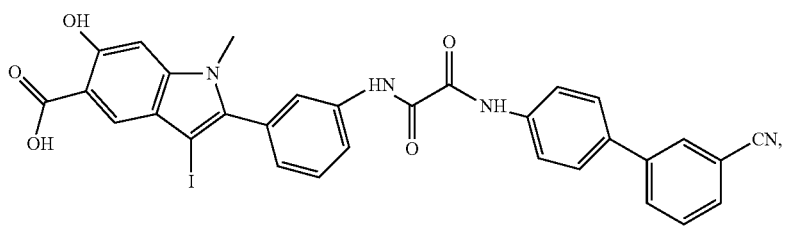
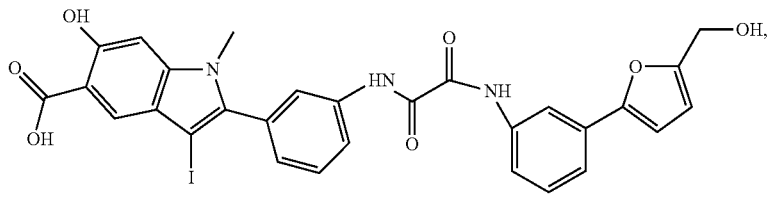

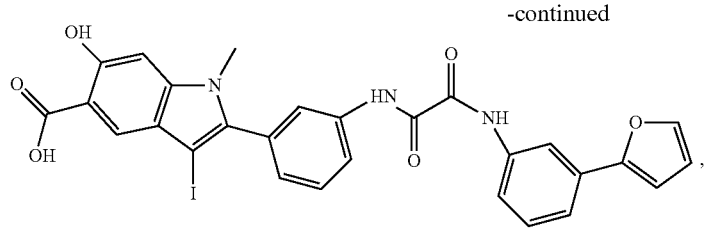

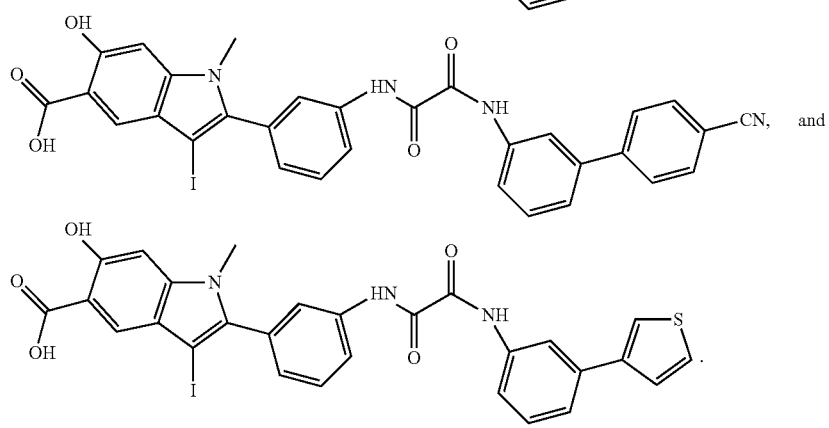

11. The hydroxyindole carboxylic acid of claim 9 having an IC$_{50}$ value for a protein tyrosine phosphatase of less 1 μM.

12. The hydroxyindole carboxylic acid of claim 9 having an IC$_{50}$ value for Src homology-2 domain containing protein tyrosine phosphatase (SHP2) of from about 0.2 μM to less than 1 μM.

13. The hydroxyindole carboxylic acid of claim 9, wherein the protein tyrosine phosphatase is selected from the group consisting of Src homology-2 domain containing protein tyrosine phosphatase 2 (SHP2), protein tyrosine phosphatase μ (PTPμ), protein tyrosine phosphatase ε (PTPε), protein tyrosine phosphatase α (PTPα), protein tyrosine phosphatase σ (PTPσ), protein tyrosine phosphatase γ (PTP γ), cytosolic protein tyrosine phosphatases, protein tyrosine phosphatase 1B (PTP1B), lymphoid protein tyrosine phosphatase (Lyp) Src homology-2 domain containing protein tyrosine phosphatase 1 (SHP 1), protein tyrosine phosphatase H1 (PTP H1), hematopoietic tyrosine phosphatase (HePTP), Striatal-enriched protein tyrosine phosphatase (STEP), protein tyrosine phosphatase PEZ, dual specificity phosphatase, vaccinia H 1 -related phosphatase (VHR), VH1-like phosphatase Z (VHZ), MAP kinase phosphatase 5 (MKP5), protein phosphatase CDC14A, ubiquitin-like domain-containing CTD phosphatase 1 (UBLCP1), laforin, low molecular weight PTP (LMWPTP), and protein phosphatase SSu72.

14. A hydroxyindole carboxylic acid for inhibiting a protein tyrosine phosphatase, the hydroxyindole carboxylic acid comprising formula (V):

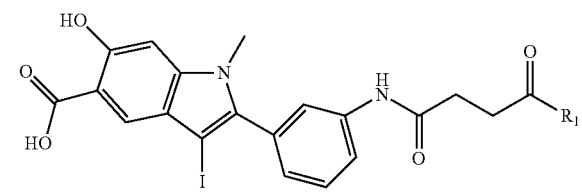

(V)

wherein R$_1$=NRaRb, wherein Ra or Rb are each independently selected from the group consisting of hydrogen, unsubstituted or substituted alkyl, unsubstituted or substituted cycloalkyl, unsubstituted or substituted heterocyclyl, unsubstituted or substituted aryl, unsubstituted or substituted heteroaryl, and fused 5-12 member aromatic or aliphatic ring system.

15. The hydroxyindole carboxylic acid of claim 14 comprising a formula selected from the group consisting of

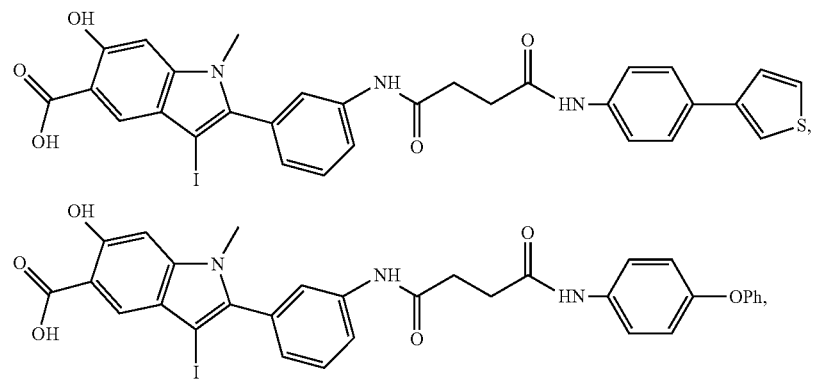

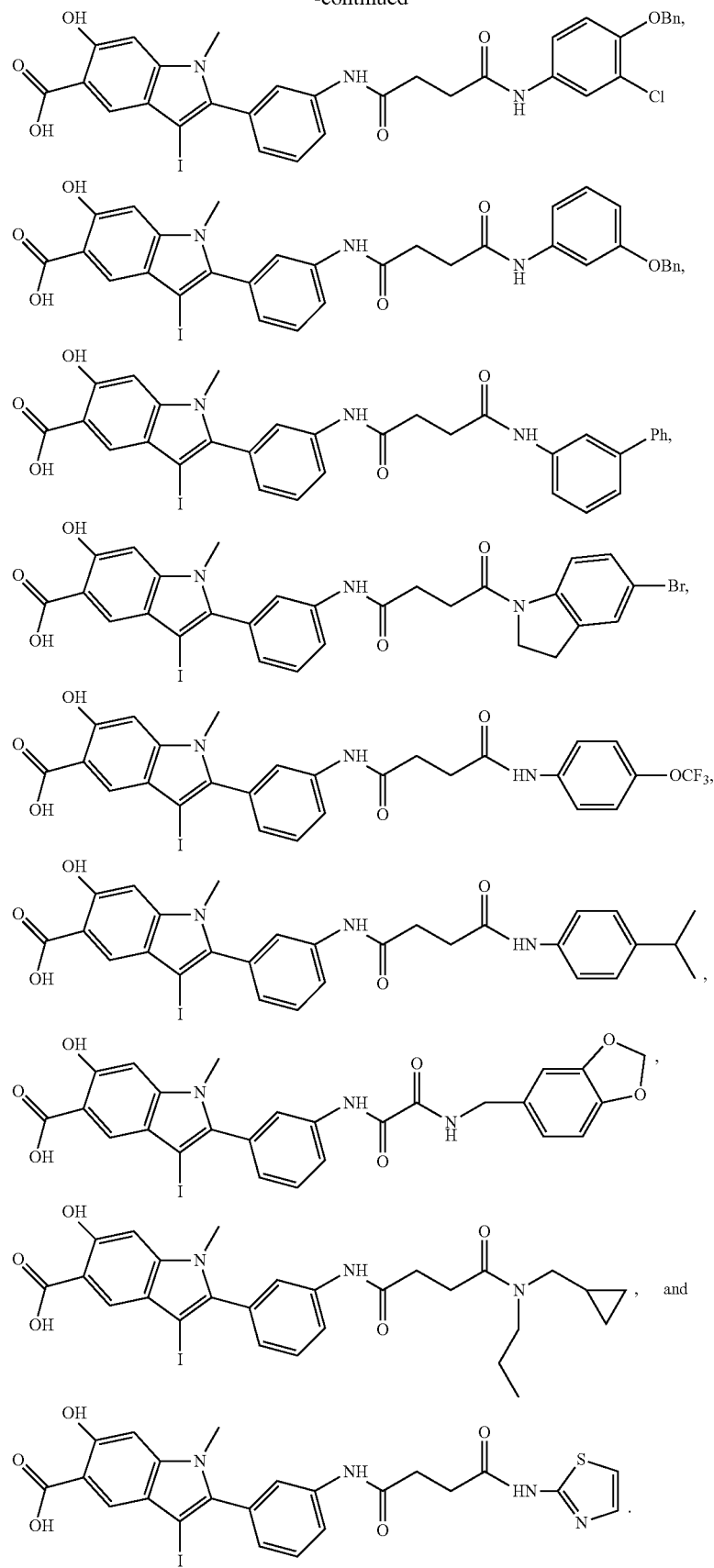

16. The hydroxyindole carboxylic acid of claim 14, wherein the protein tyrosine phosphatase is selected from the group consisting of Src homology-2 domain containing protein tyrosine phosphatase 2 (SHP2), protein tyrosine phosphatase μ (PTPμ), protein tyrosine phosphatase ε (PTPε), protein tyrosine phosphatase α (PTPα), protein tyrosine phosphatase σ (PTPσ), protein tyrosine phosphatase γ (PTP γ), cytosolic protein tyrosine phosphatases, protein tyrosine phosphatase 1B (PTP1B), lymphoid protein tyrosine phosphatase (Lyp) Src homology-2 domain containing protein tyrosine phosphatase 1 (SHP 1), protein tyrosine phosphatase H1 (PTP H1), hematopoietic tyrosine phosphatase (HePTP), Striatal-enriched protein tyrosine phosphatase (STEP), protein tyrosine phosphatase PEZ, dual specificity phosphatase, vaccinia H 1 -related phosphatase (VHR), VH1-like phosphatase Z (VHZ), MAP kinase phosphatase 5 (MKP5), protein phosphatase CDC14A, ubiquitin-like domain-containing CTD phosphatase 1 (UBLCP1), laforin, low molecular weight PTP (LMWPTP), and protein phosphatase SSu72.

17. A hydroxyindole carboxylic acid for inhibiting a protein tyrosine phosphatase, the hydroxyindole carboxylic acid comprising formula (VI):

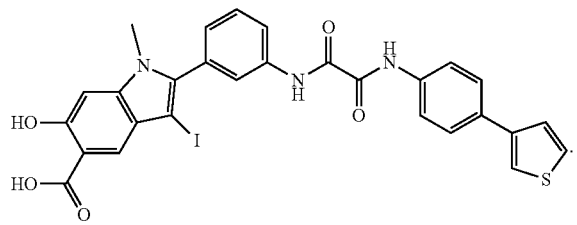

(VI)

18. A method of inhibiting a protein tyrosine phosphatase, the method comprising contacting the protein tyrosine phosphatase with the hydroxyindole carboxylic acid of claim 17.

19. The method of claim 18, wherein the protein tyrosine phosphatase is selected from the group consisting of Src homology-2 domain containing protein tyrosine phosphatase 2 (SHP2), protein tyrosine phosphatase μ (PTPμ), protein tyrosine phosphatase ε (PTPε), protein tyrosine phosphatase α (PTPα), protein tyrosine phosphatase σ (PTPσ), protein tyrosine phosphatase γ (PTPγ), cytosolic protein tyrosine phosphatases, protein tyrosine phosphatase 1B (PTP1B), lymphoid protein tyrosine phosphatase (Lyp), Src homology-2 domain containing protein tyrosine phosphatase 1 (SHP1), protein tyrosine phosphatase H1 (PTPH1), hernatopoietic tyrosine phosphatase (HePTP), Striatal-enriched protein tyrosine phosphatase (STEP), protein tyrosine phosphatase PEZ, dual specificity phosphatase, vaccinia H1-related phosphatase (VHR), VH1-like phosphatase Z (VHZ), MAP kinase phosphatase 5 (MKP5), protein phosphatase CDC14A, ubiquitin-like domain-containing CTD phosphatase 1 (UBLCP1), laforin, low molecular weight PTP (LMWPTP), and protein phosphatase SSu72.

20. The method of claim 18, wherein the hydroxyindole carboxylic acid comprises an $IC_{50}$ value for the protein tyrosine phosphatase of from about 0.2 μM to about 0.7 μM.

* * * * *